United States Patent
Mijts et al.

(10) Patent No.: US 10,870,841 B1
(45) Date of Patent: Dec. 22, 2020

(54) NUCLEIC ACID-GUIDED NUCLEASES

(71) Applicant: Inscripta, Inc., Boulder, CO (US)

(72) Inventors: Benjamin Mijts, Boulder, CO (US); Aamir Mir, Boulder, CO (US); Andrew Garst, Boulder, CO (US); Juhan Kim, Boulder, CO (US); Kyle Seamon, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 16/988,690

(22) Filed: Aug. 9, 2020

Related U.S. Application Data

(63) Continuation of application No. 16/928,742, filed on Jul. 14, 2020, now Pat. No. 10,767,169, which is a continuation of application No. 16/868,472, filed on May 6, 2020, now Pat. No. 10,724,021, which is a continuation of application No. 16/714,320, filed on Dec. 13, 2019, now Pat. No. 10,704,033.

(51) Int. Cl.
| | | |
|---|---|---|
| *C12N 9/22* | (2006.01) | |
| *C12N 15/81* | (2006.01) | |
| *C12N 15/74* | (2006.01) | |
| *C12N 15/10* | (2006.01) | |
| *C12N 15/90* | (2006.01) | |
| *C12N 15/85* | (2006.01) | |

(52) U.S. Cl.
CPC .............. *C12N 9/22* (2013.01); *C12N 15/102* (2013.01); *C12N 15/74* (2013.01); *C12N 15/81* (2013.01); *C12N 15/85* (2013.01); *C12N 15/905* (2013.01); *C12N 15/907* (2013.01); *C12N 2310/531* (2013.01)

(58) Field of Classification Search
CPC ........ C12N 9/22; C12N 15/74; C12N 15/907; C12N 15/905; C12N 15/81; C12N 15/102; C12N 15/85; C12N 2310/531
See application file for complete search history.

(56) References Cited

U.S. PATENT DOCUMENTS

| | | | | |
|---|---|---|---|---|
| 10,017,760 B2* | 7/2018 | Gill | ................ | C12N 15/1065 |
| 2020/0102386 A1* | 4/2020 | Regev | ............... | C07K 14/7051 |

* cited by examiner

*Primary Examiner* — Ganapathirama Raghu
(74) *Attorney, Agent, or Firm* — Sarah Brashears; Dianna L. DeVore

(57) ABSTRACT

The present disclosure provides novel RNA-guided enzymes for making rational and direct edits to the genome of live cells.

10 Claims, 6 Drawing Sheets

Specification includes a Sequence Listing.

NUCLEIC ACID-GUIDED NUCLEASES

RELATED CASES

The present application is a continuation of U.S. Ser. No. 16/982,742, filed 14 Jul. 2020, now U.S. Pat. No. 10,767, 169; which is a continuation of U.S. Ser. No. 16/868,472, entitled "Nucleic Acid-Guided Nucleases," filed 6 May 2020, now U.S. Pat. No. 10,724,021; which is a continuation of U.S. Ser. No. 16/714,320, entitled "Nucleic Acid-Guided Nucleases," filed 13 Dec. 2019, now U.S. Pat. No. 10,704, 033.

FIELD OF THE INVENTION

This invention relates to novel enzymes for making rational and direct edits to the genome of live cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence, hence gene function. These nucleases include nucleic acid-guided nucleases. The range of target sequences that nucleic acid-guided nucleases can recognize, however, is constrained by the need for a specific PAM to be located near the desired target sequence. PAMs are short nucleotide sequences recognized by a gRNA/nuclease complex where this complex directs editing of the target sequence. The precise PAM sequence and pam length requirements for different nucleic acid-guided nucleases vary; however, PAMs typically are 2-7 base-pair sequences adjacent or in proximity to the target sequence and, depending on the nuclease, can be 5' or 3' to the target sequence. Screening the natural diversity of nucleic acid-guided nucleases that exist across species may allow for the discovery of enzymes with enhanced nuclease activity or increased cleavage fidelity when used in a given organism; both changes that may increase the versatility of a nucleic acid-guided nuclease for certain editing tasks.

There is thus a need in the art of nucleic acid-guided nuclease gene editing for improved nucleases with varied activity in cells from different organisms and/or altered enzyme fidelity. The novel MAD-series nucleases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides novel MAD-series nucleases with varied activity in cells from different organisms.

Thus, there is provided a novel MAD-series nuclease having a codon-optimized nucleic acid sequence comprising at least 65% homology to any of SEQ ID Nos. 3-7, 11, 13, 15-22 and 24. In some aspects, the novel MAD-series nuclease having a codon-optimized nucleic acid sequence comprises at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% homology to any of SEQ ID Nos. 3-7, 11, 13, 15-22 and 24

In some aspects, the novel MAD-series nucleases are in a system comprising a gRNA having an optimal crRNA variable loop comprising UGUU, UCUU OR UAUU.

Also provided is a novel MAD-series nuclease for editing in bacteria comprising at least 80% homology to any of SEQ ID Nos. 4, 11, 15, 16, 17, 19, 21, 22 or 24; and a novel MAD-series nuclease for editing in yeast comprising at least 80% homology to any of SEQ ID Nos. 3-6, 13, 15-22 or 24.

These aspects and other features and advantages of the invention are described below in more detail.

DETAILED DESCRIPTION

Figure 1:
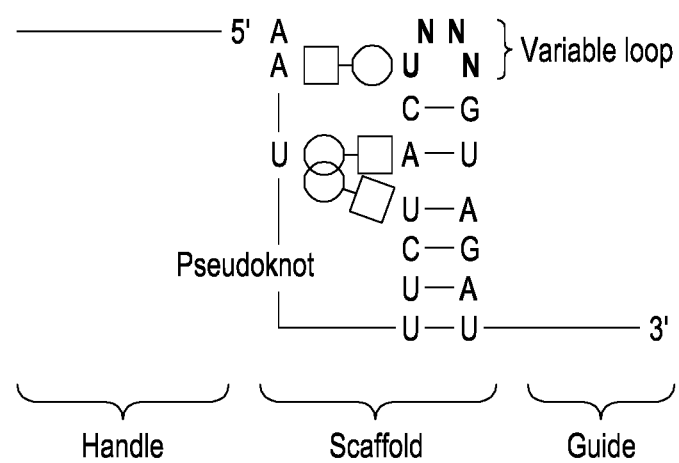
FIG. 1 depicts the minimal structure of a crRNA sequence delineating the scaffold (variable loop sequence), the location of the nuclease-targeting guide sequence and extended handle structures.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), Genetic Variation: *A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, *"Oligonucleotide Synthesis: A Practical Approach"* 1984, IRL Press, London; Nelson and Cox (2000), Lehninger, *Principles of Biochemistry* $3^{rd}$ Ed., W. H. Freeman Pub., New York, N.Y.; Berg et al. (2002) *Biochemistry, $5^{th}$* Ed., W.H. Freeman Pub., New York, N.Y.; *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011), all of which are herein incorporated in their entirety by reference for all purposes. Nuclease-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes. Basic methods for enzyme engineering may be found in, *Enzyme Engineering Methods and Protocols*, Samuelson, ed., 2013; *Protein Engineering*, Kaumaya, ed., (2012); and Kaur and Sharma, *"Directed Evolution: An Approach to Engineer Enzymes"*, Crit. Rev. Biotechnology, 26:165-69 (2006).

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "guide nucleic acid" or "guide RNA" or "gRNA" or "crRNA" refer to a polynucleotide comprising 1) a guide sequence capable of hybridizing to a genomic target locus, and 2) a scaffold sequence capable of interacting or complexing with a nucleic acid-guided nuclease (see, e.g., FIG. 1).

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible and, in some embodiments—particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, the contents of the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems

Nucleic acid-guided nucleases have been used to engineer the genomes of diverse organisms; however, differences in intrinsic DNA cutting activity, protein expression levels, cellular toxicity and activity in different organisms remain significant challenges that necessitates the screening of many candidate enzymes for editing in each organism. Nucleic acid-guided nucleases with demonstrated activity in vitro and/or in vivo in bacteria, fungi, or mammalian cells are therefore of great utility. The present disclosure provides novel gene editing MAD-series nucleases with varied PAM preferences, altered RNA-guided enzyme fidelity, and/or altered cellular toxicity or activity in different types of cells. That is, the novel MAD-series nucleases may be used to edit different cell types including, archaeal, prokaryotic, and eukaryotic (e.g., yeast, fungal, plant and animal) cells.

The novel MAD-series nucleases described herein improve RNA-guided enzyme editing systems in which nucleic acid-guided nucleases (e.g., RNA-guided nucleases) are used to edit specific target regions in an organism's genome. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby.

The novel MAD-series nucleases may be delivered to cells to be edited as a polypeptide; alternatively, a polynucleotide sequence encoding the novel MAD-series nuclease(s) is transformed or transfected into the cells to be edited. The polynucleotide sequence encoding the novel MAD-series nuclease may be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the novel MAD-series nuclease to be employed depends on many factors, such as what type of edit is to be made in the target sequence and whether an appropriate PAM is located close to the desired target sequence. The novel MAD-series nuclease may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

In general, a guide nucleic acid (e.g., gRNA), also called a CRISPR RNA (e.g., crRNA), complexes with a compatible nucleic acid-guided nuclease and can then hybridize with a target sequence, thereby directing the nuclease to the target sequence. The gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below. FIG. 1 depicts the minimal structure of the crRNA sequence delineating the scaffold (variable loop sequence), as well as the location of the nuclease-targeting guide sequence, pseudoknot and extended handle structures.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid is provided as a sequence to be expressed from a plasmid or vector and comprises both the guide sequence and the scaffold sequence as a single transcript under the control of a promoter, and in some embodiments, an inducible promoter. The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a proto spacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve fidelity, or decrease fidelity. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments—such as embodiments where cell selection is employed—the promoter driving transcription of the gRNA and the donor nucleic acid (or driving more than one gRNA/donor nucleic acid pair) is an inducible promoter. Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Ser. No. 16/399,988, filed 30 Apr. 2019; U.S. Ser. No. 16/454,865, filed 26 Jun. 2019; and U.S. Ser. No. 16/540,606, filed 14 Aug. 2019. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes a novel MAD-series nuclease comprising one or more nuclear localization sequences (NLSs), such as about or more than about 1, 2, 3, 4, 5, 6, 7, 8, 9, 10, or more NLSs. In some embodiments, the novel nuclease comprises NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the novel MAD-series nuclease editing system may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8): 3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

Typically, performing genome editing in live cells entails transforming cells with the components necessary to perform nucleic acid-guided nuclease editing. For example, the cells may be transformed simultaneously with separate engine and editing vectors; the cells may already be expressing the novel MAD-series nuclease (e.g., the cells may have already been transformed with an engine vector or the coding sequence for the novel MAD-series nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Ser. Nos. 16/024,831; 62/566,375; 62/566,688; and 62/567,697.

After the cells are transformed with the components necessary to perform nucleic acid-guided nuclease editing, the cells are cultured under conditions that promote editing. For example, if constitutive promoters are used to drive transcription of the novel MAD-series nucleases and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, nuclease, or, in the case of bacteria, a recombineering system—the cells are subjected to inducing conditions.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

Figure 2:
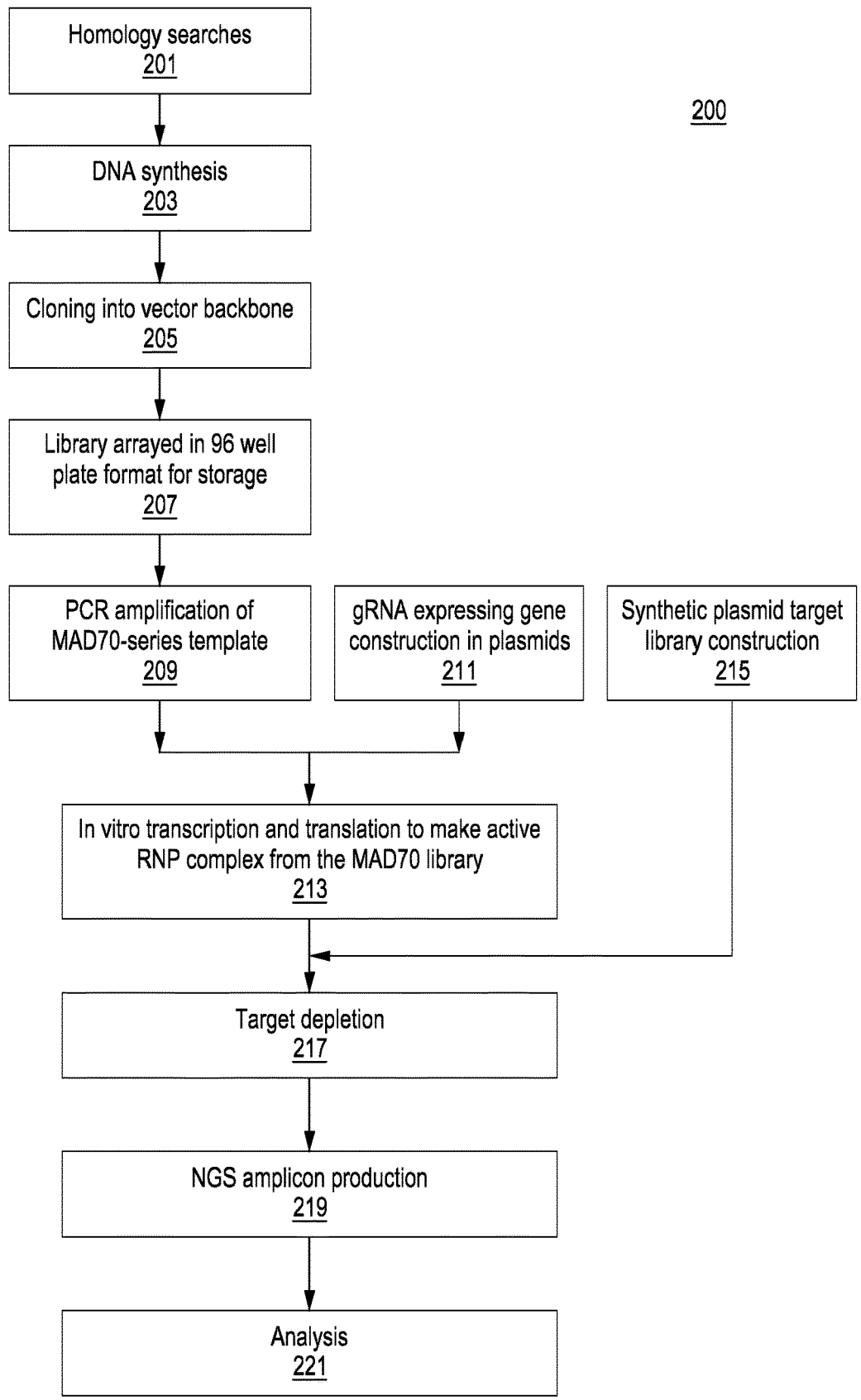
FIG. 2 is an exemplary workflow for identifying, producing, and screening the targeted nuclease activity of novel MAD-series enzymes

FIG. 2 shows an exemplary workflow 200 for creating and for in vitro screening novel MAD-series enzymes. In the first step 201, computational sequence homology searches using MAD7 as the query sequence were performed and a set of putative RNA-guided nucleases selected. In step 203, sequences with different levels of homology to MAD7 were selected for DNA synthesis with E. coli optimized codon bias. Selected sequences included four very close orthologs of MAD7 designated MAD7v1, MADv2, MAD7v3 and MAD7v4. Sequences with greater divergence from MAD7 were designated MAD2 through MAD110. In step 205, these synthetic genes were cloned into a vector backbone and single colonies yielding correct sequences confirmed by Sanger DNA sequencing.

The cells transformed with the novel MAD-series enzymes were arrayed in 96-well plates 207 for storage. At step 209, an aliquot of the cells from each well was taken, and the MAD-series sequences were amplified from each aliquot. At another step 211, a plasmid expressing a gRNA was constructed and combined with the amplified MAD-series nucleases to perform in vitro transcription and translation to make active ribonuclease protein complexes 213. A synthetic target library was constructed 215 in which to test target depletion 217 for each of the MAD-series variants. After target depletion, amplicons were produced for analysis using next-gen sequencing 219 and sequencing data analysis was performed 221 to determine target depletion.

Example 2: Vector Cloning and Novel MAD-Series Enzyme PCR for Template Generation The novel MAD-series enzyme coding sequences were cloned into a pUC57 vector with T7-promoter sequence attached to the 5'-end of the coding sequence and a T7-terminator sequence attached to the 3'-end of the coding sequence.

First, Q5 Hot Start 2× master mix reagent (NEB, Ipswich, Mass.) was used to amplify the novel MAD-series sequences using the pUC57 plasmid as a source of MAD-series templates. The forward primer 5'-TTGGGTAACGCCAGGGTTTT [SEQ ID No. 27] and reverse primer 5'-TGTGTGGAATTGTGAGCGGA [SEQ ID No. 28] amplified the sequences flanking the novel MAD-series variant in the pUC57 vector including the T7-promoter and T7-terminator components attached to the MAD7 variant sequence at the 5'- and 3'-end of the novel MAD-series variants, respectively. 1 µM primers and 5 ng/uL pUC57 template were used in PCR reactions to generate linear dsDNA product encoding the novel MAD-series variant. The PCR conditions shown in Table 1 were used:

TABLE 1

| STEP | TEMPERATURE | TIME |
| --- | --- | --- |
| DENATURATION | 98° C. | 30 SEC |
| 30 CYCLES | 98° C. | 10 SEC |
|  | 66° C. | 30 SEC |
|  | 72° C. | 2.5 MIN |
| FINAL EXTENSION | 72° C. | 2 MIN |
| HOLD | 12° C. |  |

Example 3: In Vitro Transcription and Translation for Production of MAD-Series Nucleases and gRNAs in a Single Well A PURExpress® In Vitro Protein Synthesis Kit (NEB, Ipswich, Mass.) was used to produce novel MAD-series variant proteins from the PCR-amplified linear dsDNA template and also to produce gRNAs. In each well in a 96-well plate, the reagents listed in Table 2 were mixed to start the production of MAD7 variants and gRNA:

TABLE 2

| | REAGENTS | VOLUME (μl) |
|---|---|---|
| 1 | SolA (NEB kit) | 3.3 |
| 2 | SolB (NEB kit) | 2.5 |
| 3 | gRNA mix (4 ng/ul stock) | 0.8 |
| 4 | Murine RNase inhibitor (NEB) | 0.2 |
| 5 | Water | 0.5 |
| 6 | PCR amplified T7 MAD-series variants | 1.0 |

A master mix with all reagents except the PCR-amplified T7-MAD-series variants was prepared and kept on ice. After 7.3 μL of the master mix was distributed in each well in 96 well plates, 1 μL of the PCR amplified MAD-series variants under the control of T7 promoter was added. The 96-well plates were sealed and incubated for 4 hrs at 37° C. in a thermal cycler. The plates were kept at room temperature until the target pool was added to perform the target depletion reaction.

Example 4: Performing Target Depletion, PCR and NGS

After 4 hours incubation to allow production of the novel MAD-series variants and gRNAs, 4 μL of the target library pool (10 ng/μL) was added to the in vitro transcription/translation reaction mixture. After the target library was added, reaction mixtures were incubated overnight at 37° C. The target depletion reaction mixtures were diluted into PCR-grade water that contains RNAse A and then boiled for 5 min at 95° C. The mixtures were then amplified and sequenced. The PCR conditions are shown in Table 3:

TABLE 3

| STEP | TEMPERATURE | TIME |
|---|---|---|
| DENATURATION | 98° C. | 30 SEC |
| 6 CYCLES | 98° C. | 10 SEC |
| | 61° C. | 30 SEC |
| | 72° C. | 10 SEC |
| 22 CYCLES | 98° C. | 10 SEC |
| | 72° C. | 10 SEC |
| FINAL EXTENSION | 72° C. | 2 MINUTES |
| HOLD | 12° C. | |

Table 4 shows the results of the in vitro assay.

TABLE 4

| Nuclease | Native crRNA loop | Active in vitro | Optimal crRNA loop (variable loop - see FIG. 1) | SEQ ID NO. |
|---|---|---|---|---|
| MAD7 | UGUU | Active | UGUU | SEQ ID No. 1 |
| MAD7v1 | UGUU | Active | UGUU | SEQ ID No. 3 |
| MAD7v2 | UGUU | Active | UGUU | SEQ ID No. 4 |
| MAD7v3 | UGUU | Active | UGUU | SEQ ID No. 5 |
| MAD7v4 | UGUU | Active | UGUU | SEQ ID No. 6 |
| MAD2 | Unknown | Active | UGUU, UCUU | SEQ ID No. 7 |
| MAD3 | UCUUU | Active | UCUUU | SEQ ID No. 8 |
| MAD4 | UGUU | Active | UGUU, UCUU | SEQ ID No. 9 |
| MAD5 | UAGU | Inactive | UAGU | SEQ ID No. 10 |
| MAD6 | UAUU | Active | UAUU | SEQ ID No. 11 |
| MAD12 | UCUU | Active | UCUU, UAUU | SEQ ID No. 12 |
| MAD31 | unknown | Active | UCUU, UAUU | SEQ ID No. 13 |
| MAD35 | unknown | Active | UGUU, UAUU | SEQ ID No. 14 |
| MAD41 | UGUGU | Active | UAUU, UCUU | SEQ ID No. 15 |
| MAD44 | UAUU | Active | UCUU, UAUU | SEQ ID No. 16 |
| MAD50 | UGUU | Active | UCUU, UGUU | SEQ ID No. 17 |
| MAD53 | unknown | Active | UAUU | SEQ ID No. 18 |
| MAD54 | unknown | Active | UGUU | SEQ ID No. 19 |
| MAD57 | UAGU | Active | UAUU | SEQ ID No. 20 |
| MAD82 | UGUU | Active | UCUU, UGUU | SEQ ID No. 21 |
| MAD89 | UAUU | Active | UGUU, UAUU | SEQ ID No. 22 |
| MAD90 | unknown | Active | UAUU, UGUU | SEQ ID No. 23 |
| MAD92 | UAUU | Weakly Active | UAUU | SEQ ID No. 24 |
| MAD8 | UAUU | Inactive | | |
| MAD10 | UUUU | Inactive | | |
| MAD28 | UUUU | Inactive | | |
| MAD29 | Unknown | Inactive | | |
| MAD30 | UUUU | Inactive | | |
| MAD32 | UUUU | Inactive | | |
| MAD33 | UUUU | Inactive | | |
| MAD37 | Unknown | Inactive | | |
| MAD38 | uACUAu | Inactive | | |
| MAD40 | UUUU | Inactive | | |
| MAD43 | UUUU | Inactive | | |
| MAD45 | unknown | Inactive | | |
| MAD49 | UUUU | Inactive | | |
| MAD52 | UUCG | Inactive | | |
| MAD71 | unknown | Inactive | | |
| MAD95 | unknown | Inactive | | |
| MAD107 | unknown | Inactive | | |
| MAD108 | UGUU | Inactive | | |
| MAD110 | unknown | Inactive | | |

Example 5: *E. coli* Genome Editing

Library Amplification:

50 μL reactions were run with 5 μL of the diluted synthetic oligonucleotide editing cassettes from a chip. The PCR conditions were 95° C. for 1 minute, then 18 rounds of 95° C. for 30 seconds/60° C. for 30 seconds/72° C. for 2 minutes 30 seconds with a final hold at 72° C. for 5 minutes. The product was run on an agarose gel to check for homogeneity. For amplifying the backbone, ten-fold serial dilutions were performed of the pL backbone—a backbone with the pL inducible promoter positioned to drive transcription of the galK editing cassette. The PCR conditions were 95° C. for 1 minute, then 30 rounds of 95° C. for 1 minute/60° C. for 1 minute 30 seconds/72° C. for 2 minutes 30 seconds with a final hold at 72° C. for 5 minutes. Again, the product was run on an agarose gel to check for homogeneity. Amplicons were pooled, miniprepped, and 6 μL of CutSmart® (NEB, Ipswich, Mass.) enzyme was added and the digestion was allowed to proceed at 37° C. for 1 hour. The linearized backbone was quantified before isothermal assembly with the purified cassette library.

A Gibson reaction was performed with 150 ng backbone, 100 ng insert, and Gibson® (NEB, Ipswich Mass.) MASTER MIX. The reaction was incubated for 45 minutes at 50° C. The reaction was dialyzed for 30 minutes. 5 μL of the dialyzed Gibson reaction was transformed into E. cloni competent cells. The E.cloni® SUPREME electrocompetent cells (Lucigen, Middleton Wis.) were outgrown in 25 ML SOB+100 μg/mL Carb and a midiprep was performed. 100 ng of the cloned library was transformed into 50 μL competent cells at 2400V in a 2 mm cuvette. The cells were allowed to recover in SOB and 10-fold dilutions were spot-plated. To induce editing, 50 μL of outgrowth was transferred into SOB/chlor/carb/1% arabinose in a well plate. The cells were allowed to reach mid log phase and then were incubated at 42° C. for 2-2.5 hours. Serial dilutions were performed and the cells were plated to determine editing efficiency.

Figure 3:
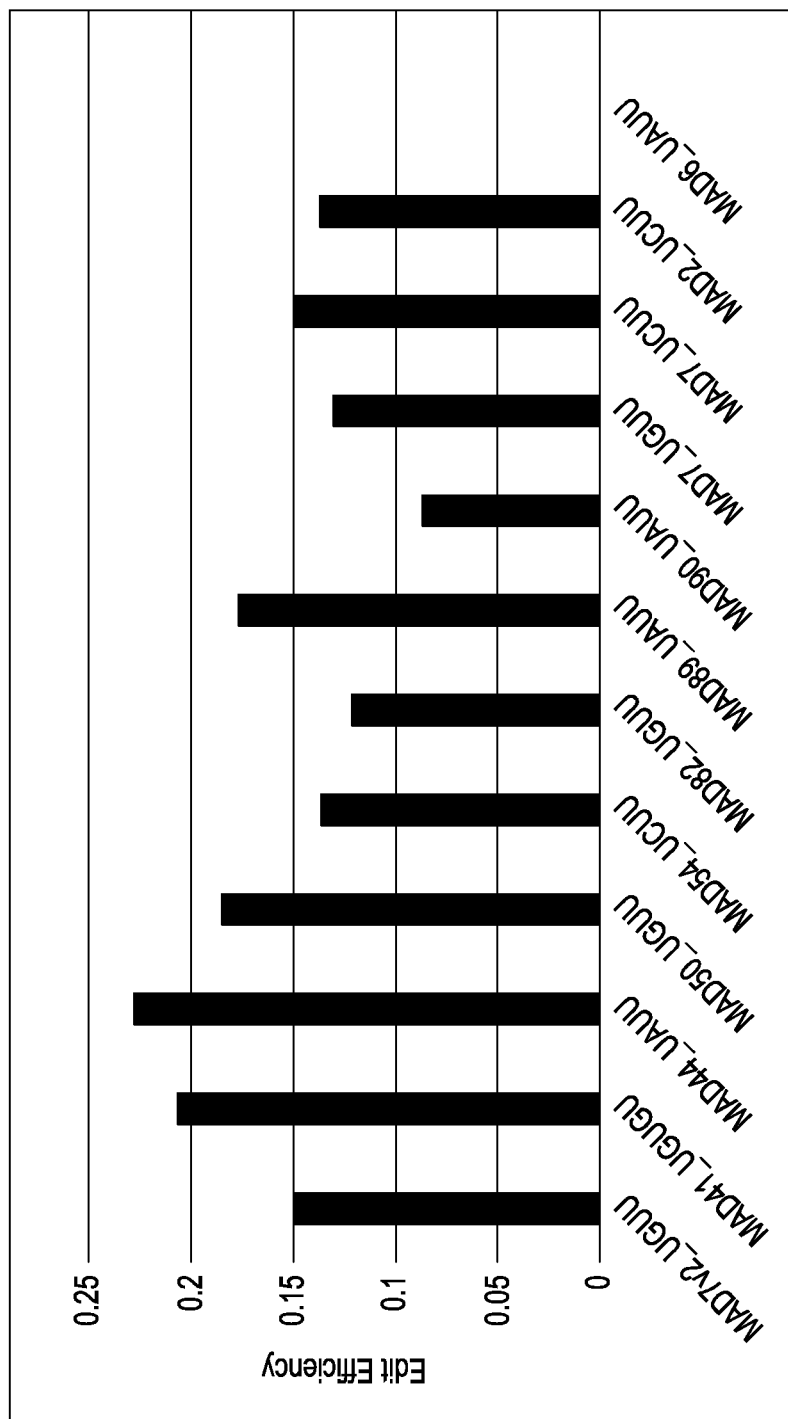
FIG. 3 shows the results of editing in *E. coli* as assessed by colorimetric screening of precise edits in the galK locus by the indicated MAD-series nuclease with the indicated variable loop sequence.

FIG. 3 shows the results of in vivo editing of E. coli assessed by colorimetric screening of precise edits in the galK locus by the indicated protein with the indicated variable loop sequence. Table 5 shows the results of in vivo E. coli editing:

TABLE 5

| Nuclease | Active in E. coli | crRNA loop | SEQ ID No. |
| --- | --- | --- | --- |
| MAD7 | Active | UGUU, UCUU | SEQ ID No. 1 |
| MAD7v2 | Active | UGUU | SEQ ID No. 4 |
| MAD2 | Active | UCUU | SEQ ID No. 7 |
| MAD3 | Inactive | | SEQ ID No. 8 |
| MAD4 | Inactive | | SEQ ID No. 9 |
| MAD6 | Weakly Active | UAUU | SEQ ID No. 11 |
| MAD41 | Active | UGUGU | SEQ ID No. 15 |
| MAD44 | Active | UAUU | SEQ ID No. 16 |
| MAD50 | Active | UGUU | SEQ ID No. 17 |
| MAD54 | Active | UCUU | SEQ ID No. 19 |
| MAD82 | Active | UGUU | SEQ ID No. 21 |
| MAD89 | Active | UAUU | SEQ ID No. 22 |
| MAD92 | Active | UAUU | SEQ ID No. 24 |

Example 6: S. cerevisiae Genome Editing

For the enzymes that showed activity in vitro, the genome editing activity was tested in vivo in S. cerevisiae. A two-micron plasmid with the KanMX resistance gene was constructed for the sequential introduction of DNA containing an editing cassette with SNR52 promoter-driven crRNA and a CYC1 promoter-driven nuclease protein. The editing cassette consisted of the crRNA to guide the nuclease to cut at a specific DNA sequence, a short pentaT linker, and a repair template containing the mutation of interest flanked by regions of homology to the genome. The screening plasmid was linearized by the StuI restriction endonuclease, and the editing cassette was introduced downstream of the SNR52p promoter by isothermal assembly. The editing cassettes (see Table 6 below) all targeted TTTV PAM sequences in the CAN1 locus and introduce a premature stop codon to knock out the functional Can1 protein.

TABLE 6

List of yeast editing cassette sequences tested

| Cassette name | PAM Targeted | crRNA scaffold | Yeast Editing Cassette Sequence | SEQ ID No. |
| --- | --- | --- | --- | --- |
| Can1_S30 stop | TTTA | UGUU | GGCCCCAAATTCTAATTTCTACTGTTGTAG ATACGACGTTGAAGCTTCACAATTTTTACG CCGACATAGAGGAGAAGCATATGTACAAT GAGCCGGTCACAACCCTCGAGACACGACG TTGAAGCTTAACAAACACACCACAGACGT GGGTCAATACCATTGAAAGATGAGAAAAG TAACAATATACGCGCTCCTGCCC | SEQ ID No. 29 |
| Can1_S30 stop | TTTA | UCUU | GGCCCCAAATTCTAATTTCTACTCTTGTAG ATACGACGTTGAAGCTTCACAATTTTTACG CCGACATAGAGGAGAAGCATATGTACAAT GAGCCGGTCACAACCCTCGAGACACGACG TTGAAGCTTAACAAACACACCACAGACGT GGGTCAATACCATTGAAAGATGAGAAAAG TAACAATATACGCGCTCCTGCCC | SEQ ID No. 30 |
| Can1_S30 stop | TTTA | UAUU | GGCCCCAAATTCTAATTTCTACTATTGTAG ATACGACGTTGAAGCTTCACAATTTTTACG CCGACATAGAGGAGAAGCATATGTACAAT GAGCCGGTCACAACCCTCGAGACACGACG TTGAAGCTTAACAAACACACCACAGACGT GGGTCAATACCATTGAAAGATGAGAAAAG TAACAATATACGCGCTCCTGCCC | SEQ ID No. 31 |
| Can1_S30 stop | TTTA | UGUGU | GGCCCCAAATTCTAATTTCTACTGTGTGT AGATACGACGTTGAAGCTTCACAATTTTTA CGCCGACATAGAGGAGAAGCATATGTACA ATGAGCCGGTCACAACCCTCGAGACACGA CGTTGAAGCTTAACAAACACACCACAGAC GTGGGTCAATACCATTGAAAGATGAGAAA AGTAACAATATACGCGCTCCTGCCC | SEQ ID No. 32 |
| Can1_K42 stop | TTTA | UGUU | GGCCCCAAATTCTAATTTCTACTGTTGTAG ATCTTTTCTCATCTTTCAATGGTTTTTGTAT CCTCGCCATTTACTCTCGTCGGGAAAGAG CGCAATGGATACAATTCCCCACTTTTCTCA TCTTACAATGGTATTGACCCACGTCTGTGG TGTGTTTGTGAAGCTTCAACGTCGTCAATA TACGCGCTCCTGCCC | SEQ ID No. 33 |
| Can1_K42 stop | TTTA | UCUU | GGCCCCAAATTCTAATTTCTACTCTTGTAG ATCTTTTCTCATCTTTCAATGGTTTTTGTAT CCTCGCCATTTACTCTCGTCGGGAAAGAG CGCAATGGATACAATTCCCCACTTTTCTCA TCTTACAATGGTATTGACCCACGTCTGTGG TGTGTTTGTGAAGCTTCAACGTCGTCAATA TACGCGCTCCTGCCC | SEQ ID No. 34 |

TABLE 6-continued

List of yeast editing cassette sequences tested

| Cassette name | PAM Targeted | crRNA scaffold | Yeast Editing Cassette Sequence | SEQ ID No. |
|---|---|---|---|---|
| Can1_K42 stop | TTTA | UAUU | GGCCCCAAATTCTAATTTCTACTATTGTAG<br>ATCTTTTCTCATCTTTCAATGGTTTTTGTAT<br>CCTCGCCATTTACTCTCGTCGGGAAAGAG<br>CGCAATGGATACAATTCCCCACTTTTCTCA<br>TCTTACAATGGTATTGACCCACGTCTGTGG<br>TGTGTTTGTGAAGCTTCAACGTCGTCAATA<br>TACGCGCTCCTGCCC | SEQ ID No. 35 |
| Can1_K42 stop | TTTA | UGUGU | GGCCCCAAATTCTAATTTCTACTGTGTGT<br>AGATCTTTTCTCATCTTTCAATGGTTTTTGT<br>ATCCTCGCCATTTACTCTCGTCGGGAAAGA<br>GCGCAATGGATACAATTCCCCACTTTTCTC<br>ATCTTACAATGGTATTGACCCACGTCTGTG<br>GTGTGTTTGTGAAGCTTCAACGTCGTCAAT<br>ATACGCGCTCCTGCCC | SEQ ID No. 36 |
| Can1_N60 stop | TTTC | UGUU | GGCCCCAAATTCTAATTTCTACTGTTGTAG<br>ATCCGACGAGAGTAAATGGCGATTTTTTC<br>AATACCATTGAAAGATGAGAAAAGTAAAG<br>AATTGTATCCATTGCGCTCGTTCCCGACGA<br>GAGTATAAGGCGAGGATACGTTCTCTATG<br>GAGGATGGCATAGGTGATGAAGATGAAG<br>GAGAAGCAATATACGCGCTCCTGCCC | SEQ ID No. 37 |
| Can1_N60 stop | TTTC | UCUU | GGCCCCAAATTCTAATTTCTACTCTTGTAG<br>ATCCGACGAGAGTAAATGGCGATTTTTTC<br>AATACCATTGAAAGATGAGAAAAGTAAAG<br>AATTGTATCCATTGCGCTCGTTCCCGACGA<br>GAGTATAAGGCGAGGATACGTTCTCTATG<br>GAGGATGGCATAGGTGATGAAGATGAAG<br>GAGAAGCAATATACGCGCTCCTGCCC | SEQ ID No. 38 |
| Can1_N60 stop | TTTC | UAUU | GGCCCCAAATTCTAATTTCTACTATTGTAG<br>ATCCGACGAGAGTAAATGGCGATTTTTTC<br>AATACCATTGAAAGATGAGAAAAGTAAAG<br>AATTGTATCCATTGCGCTCGTTCCCGACGA<br>GAGTATAAGGCGAGGATACGTTCTCTATG<br>GAGGATGGCATAGGTGATGAAGATGAAG<br>GAGAAGCAATATACGCGCTCCTGCCC | SEQ ID No. 39 |
| Can1_N60 stop | TTTC | UGUGU | GGCCCCAAATTCTAATTTCTACTGTGTGT<br>AGATCCGACGAGAGTAAATGGCGATTTTT<br>TCAATACCATTGAAAGATGAGAAAAGTAA<br>AGAATTGTATCCATTGCGCTCGTTCCCGAC<br>GAGAGTATAAGGCGAGGATACGTTCTCTA<br>TGGAGGATGGCATAGGTGATGAAGATGAA<br>GGAGAAGCAATATACGCGCTCCTGCCC | SEQ ID No. 40 |
| Can1_T115 stop | TTTA | UGUU | GGCCCCAAATTCTAATTTCTACTGTTGTAG<br>ATTCCACACCTCTGACCAACGCTTTTTATT<br>GGTATGATTGCCCTTGGTGGTACTATTGGT<br>ACAGGTCTTTTCATTGGATTATCCACACCT<br>CTGTAAAACGCCGGCCCAGTGGGCGCTCT<br>TATATCATATTTATTTATGGGTTCTTTGGC<br>ATCAATATACGCGCTCCTGCCC | SEQ ID No. 41 |
| Can1_T115 stop | TTTA | UCUU | GGCCCCAAATTCTAATTTCTACTCTTGTAG<br>ATTCCACACCTCTGACCAACGCTTTTTATT<br>GGTATGATTGCCCTTGGTGGTACTATTGGT<br>ACAGGTCTTTTCATTGGATTATCCACACCT<br>CTGTAAAACGCCGGCCCAGTGGGCGCTCT<br>TATATCATATTTATTTATGGGTTCTTTGGC<br>ATCAATATACGCGCTCCTGCCC | SEQ ID No. 42 |
| Can1_T115 stop | TTTA | UAUU | GGCCCCAAATTCTAATTTCTACTATTGTAG<br>ATTCCACACCTCTGACCAACGCTTTTTATT<br>GGTATGATTGCCCTTGGTGGTACTATTGGT<br>ACAGGTCTTTTCATTGGATTATCCACACCT<br>CTGTAAAACGCCGGCCCAGTGGGCGCTCT<br>TATATCATATTTATTTATGGGTTCTTTGGC<br>ATCAATATACGCGCTCCTGCCC | SEQ ID No. 43 |
| Can1_T115 stop | TTTA | UGUGU | GGCCCCAAATTCTAATTTCTACTGTGTGT<br>AGATTCCACACCTCTGACCAACGCTTTTTA | SEQ ID No. 44 |

TABLE 6-continued

List of yeast editing cassette sequences tested

| Cassette name | PAM Targeted | crRNA scaffold | Yeast Editing Cassette Sequence | SEQ ID No. |
|---|---|---|---|---|
| | | | TTGGTATGATTGCCCTTGGTGGTACTATTG<br>GTACAGGTCTTTTCATTGGATTATCCACAC<br>CTCTGTAAAACGCCGGCCCAGTGGGCGCT<br>CTTATATCATATTTATTTATGGGTTCTTTG<br>GCATCAATATACGCGCTCCTGCCC | |
| Can1_Q1 58stop | TTTC | UGUU | GGCCCCAAATTCTAATTTCTACTGTTGTAG<br>ATACAGTTTTCTCACAAAGATTTTTTTCT<br>GTCACGCAGTCCTTGGGTGAAATGGCTAC<br>ATTCATCCCTGTTACATCCTCGTTCACAGT<br>TTTCTCATAAAGATTCCTTTCTCCAGCATT<br>TGGTGCGGCCAATGGTTACATGTATTGGTT<br>TTCAATATACGCGCTCCTGCCC | SEQ ID No. 45 |
| Can1_Q1 58stop | TTTC | UCUU | GGCCCCAAATTCTAATTTCTACTCTTGTAG<br>ATACAGTTTTCTCACAAAGATTTTTTTCT<br>GTCACGCAGTCCTTGGGTGAAATGGCTAC<br>ATTCATCCCTGTTACATCCTCGTTCACAGT<br>TTTCTCATAAAGATTCCTTTCTCCAGCATT<br>TGGTGCGGCCAATGGTTACATGTATTGGTT<br>TTCAATATACGCGCTCCTGCCC | SEQ ID No. 46 |
| Can1_Q1 58stop | TTTC | UAUU | GGCCCCAAATTCTAATTTCTACTATTGTAG<br>ATACAGTTTTCTCACAAAGATTTTTTTCT<br>GTCACGCAGTCCTTGGGTGAAATGGCTAC<br>ATTCATCCCTGTTACATCCTCGTTCACAGT<br>TTTCTCATAAAGATTCCTTTCTCCAGCATT<br>TGGTGCGGCCAATGGTTACATGTATTGGTT<br>TTCAATATACGCGCTCCTGCCC | SEQ ID No. 47 |
| Can1_Q1 58stop | TTTC | UAUU | GGCCCCAAATTCTAATTTCTACTGTGTGT<br>AGATACAGTTTTCTCACAAAGATTTTTTTT<br>CTGTCACGCAGTCCTTGGGTGAAATGGCT<br>ACATTCATCCCTGTTACATCCTCGTTCACA<br>GTTTTCTCATAAAGATTCCTTTCTCCAGCA<br>TTTGGTGCGGCCAATGGTTACATGTATTGG<br>TTTTCAATATACGCGCTCCTGCCC | SEQ ID No. 48 |
| Can1_I214 stop | TTTG | UGUU | GGCCCCAAATTCTAATTTCTACTGTTGTAG<br>ATGGTAATTATCACAATAATGATTTTTCAT<br>TCAATTTTGGACGTACAAAGTTCCACTGGC<br>GGCATGGATTAGTATTTGGAAGGTAATTA<br>TCACATAAATGAACTTGTTCCCTGTCAAAT<br>ATTACGGTGAATTCGAGTTCTGGGTCGCC<br>AATATACGCGCTCCTGCCC | SEQ ID No. 49 |
| Can1_I214 stop | TTTG | UCUU | GGCCCCAAATTCTAATTTCTACTCTTGTAG<br>ATGGTAATTATCACAATAATGATTTTTCAT<br>TCAATTTTGGACGTACAAAGTTCCACTGGC<br>GGCATGGATTAGTATTTGGAAGGTAATTA<br>TCACATAAATGAACTTGTTCCCTGTCAAAT<br>ATTACGGTGAATTCGAGTTCTGGGTCGCC<br>AATATACGCGCTCCTGCCC | SEQ ID No. 50 |
| Can1_I214 stop | TTTG | UAUU | GGCCCCAAATTCTAATTTCTACTATTGTAG<br>ATGGTAATTATCACAATAATGATTTTTCAT<br>TCAATTTTGGACGTACAAAGTTCCACTGGC<br>GGCATGGATTAGTATTTGGAAGGTAATTA<br>TCACATAAATGAACTTGTTCCCTGTCAAAT<br>ATTACGGTGAATTCGAGTTCTGGGTCGCC<br>AATATACGCGCTCCTGCCC | SEQ ID No. 51 |
| Can1_I214 stop | TTTG | UGUGU | GGCCCCAAATTCTAATTTCTACTGTGTGT<br>AGATGGTAATTATCACAATAATGATTTTTC<br>ATTCAATTTTGGACGTACAAAGTTCCACTG<br>GCGGCATGGATTAGTATTTGGAAGGTAAT<br>TATCACATAAATGAACTTGTTCCCTGTCAA<br>ATATTACGGTGAATTCGAGTTCTGGGTCGC<br>CAATATACGCGCTCCTGCCC | SEQ ID No. 52 |

The nuclease proteins were amplified by polymerase chain reaction with oligonucleotide primers to introduce an SV40 nuclear localization sequence at the N-terminus consisting of the DNA sequence ATGGCACC-CAAGAAGAAGAGGAAGGTGTTA [SEQ ID No. 25] corresponding to a protein sequence of MAPKKKRKVL [SEQ ID NO. 26]. The resulting amplified DNA fragment (400 ng, purified) was then co-transformed along with a PsiI-linearized screening plasmid (250 ng) that already contained one of the above editing cassettes to assemble the complete editing plasmid by in vivo gap repair. Cells containing a repaired plasmid were selected for in yeast peptone-dextrose (YPD) containing 200 mg/L Geneticin for 3 days at 30° C. in a humidified shaking incubator. The resulting saturated culture was diluted 1:100 to 1:200 into synthetic complete yeast media lacking arginine and containing 50 mg/L of canavanine and grown overnight at 30° C. in a humidified shaking incubator. Because knockout of the Cant protein allows yeast to grow in the presence of the otherwise toxic analog canavanine, the relative OD600 of the overnight cultures is proportional to the rate of genome mutation induced by the transformed nuclease protein. Table 7 shows the results of in vivo S. cerevisiae editing:

TABLE 7

| Nuclease | Active in S. cerevisiae | crRNA loop | SEQ ID No. |
|---|---|---|---|
| MAD7 | Active | UGUU, UCUU | SEQ ID No. 1 |
| MAD7v1 | Active | UGUU | SEQ ID No. 3 |
| MAD7v2 | Active | UGUU | SEQ ID No. 4 |
| MAD7v3 | Active | UGUU | SEQ ID No. 5 |
| MAD7v4 | Active | UGUU | SEQ ID No. 6 |
| MAD2 | Weakly Active | UCUU | SEQ ID No. 7 |
| MAD4 | Weakly Active | UGUU | SEQ ID No. 9 |
| MAD6 | Inactive | | SEQ ID No. 11 |
| MAD31 | Active | UCUU | SEQ ID No. 13 |
| MAD41 | Active | UGUGU, UCUU | SEQ ID No. 15 |

TABLE 7-continued

| Nuclease | Active in S. cerevisiae | crRNA loop | SEQ ID No. |
|---|---|---|---|
| MAD44 | Active | UAUU, UCUU | SEQ ID No. 16 |
| MAD50 | Active | UCUU, UGUU | SEQ ID No. 17 |
| MAD53 | Active | UAUU | SEQ ID No. 18 |
| MAD54 | Active | UCUU | SEQ ID No. 19 |
| MAD57 | Active | UCUU | SEQ ID No. 20 |
| MAD82 | Active | UCUU, UGUU | SEQ ID No. 21 |
| MAD89 | Active | UCUU, UAUU | SEQ ID No. 22 |
| MAD92 | Weakly Active | UAUU | SEQ ID No. 24 |

Figure 4:
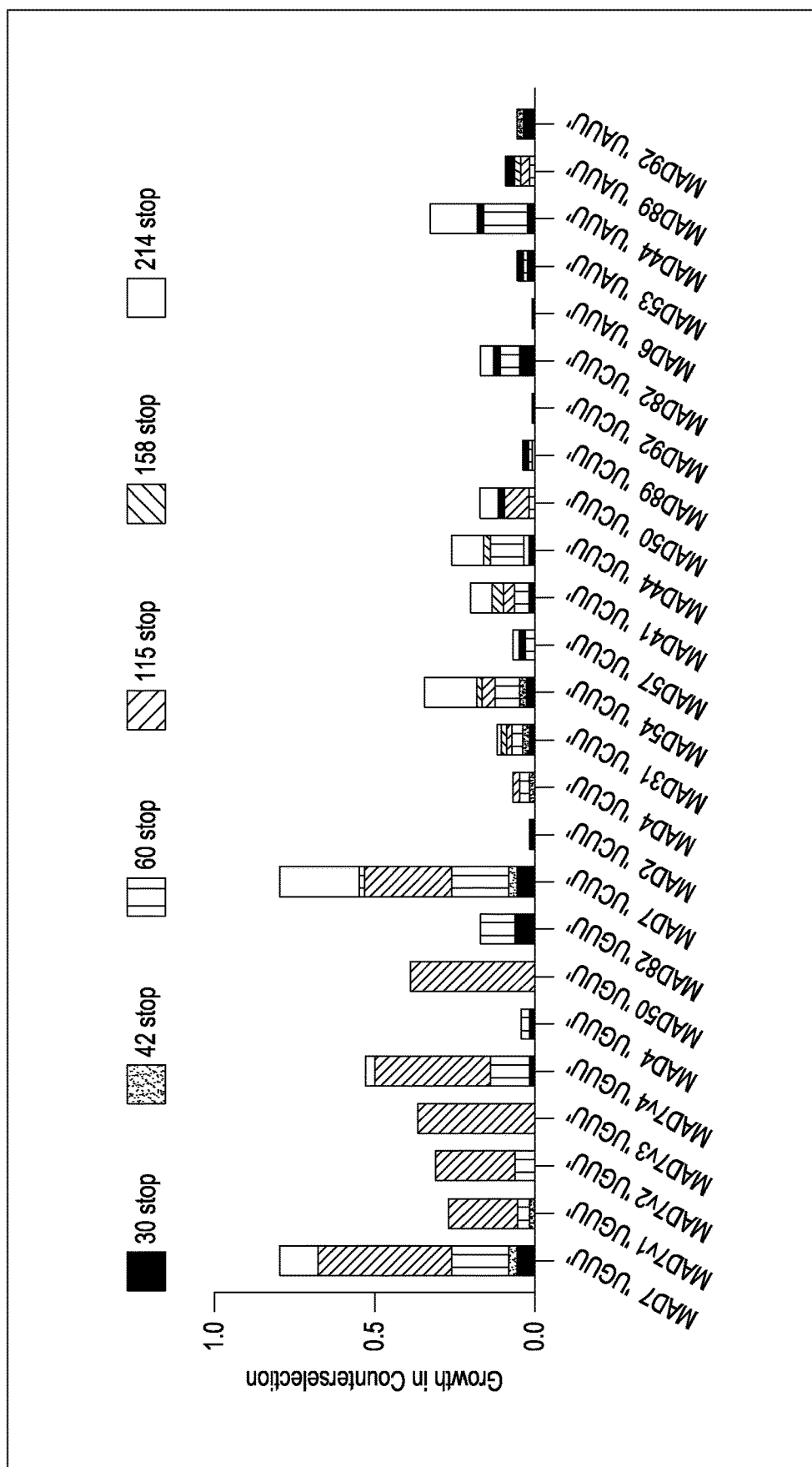
FIG. 4 shows the results of editing in *S. cerevisiae* as assessed by growth in canavanine-containing medium induced by precise edits in the Can1 locus using the indicated MAD-series nuclease with the indicated variable loop sequence.
Figure 5:
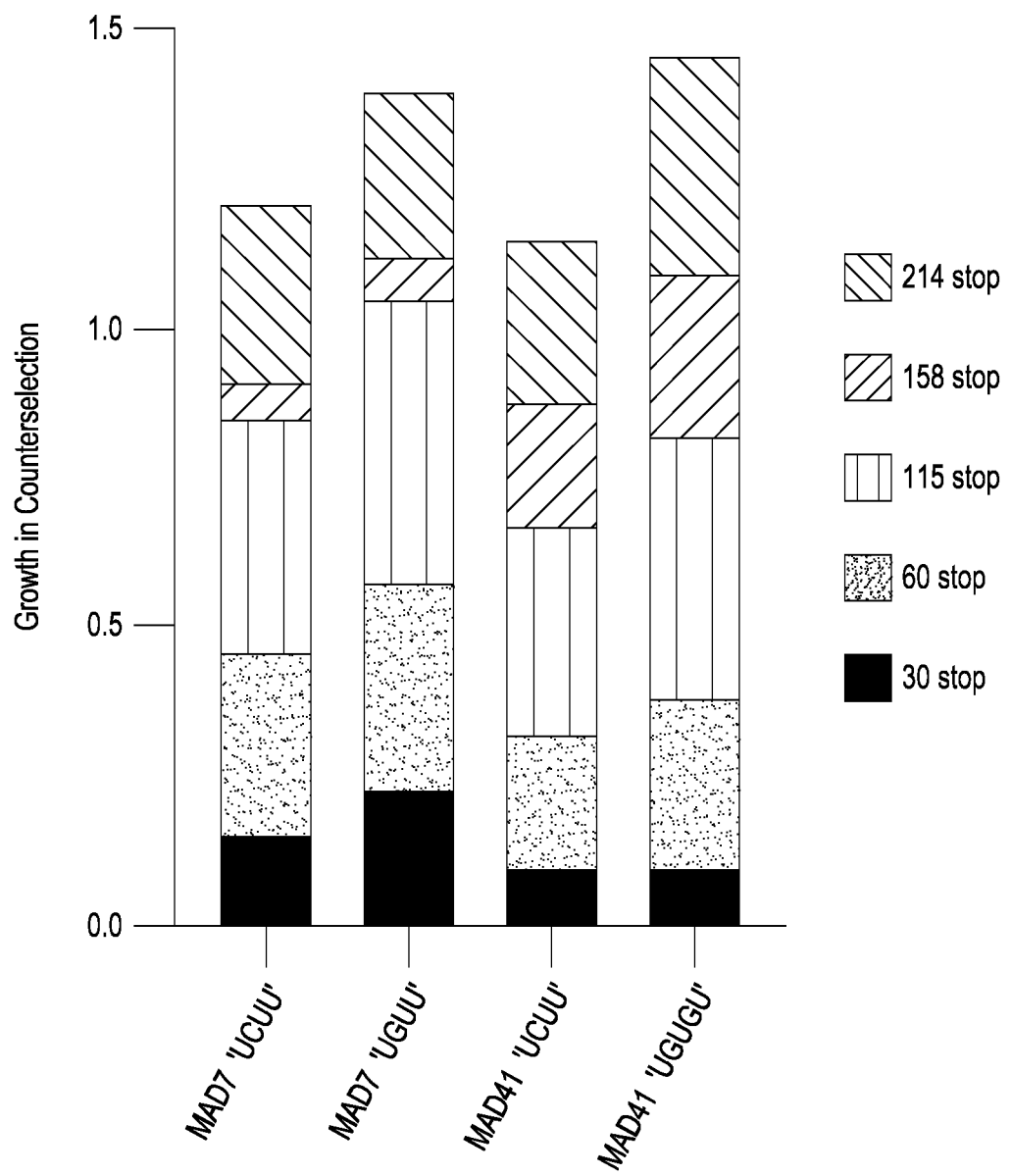
FIG. 5 shows the results of editing in *S. cerevisiae* by MAD7 and MAD41 using additional variable loop scaffolds.

FIG. 4 shows the results of in vivo editing of S. cerevisiae assessed by growth in canavanine-containing medium induced by precise edits in the Can1 locus using the indicated nuclease with the indicated variable loop sequence. FIG. 5 shows the results of in vivo editing of S. cerevisiae by MAD7 and MAD41 using additional variable loop scaffolds.

Example 7: Mammalian Cell Line Genome Editing

HEK293T cells were transfected in 96-well plates using 2 µL polyfect and 200 ng of each of the engine and editing plasmids. After 48 hours, the medium was aspirated and 100 µL of Taq lysis buffer with proteinase K (1 mg/mL final) was added (10× Taq lysis buffer: 100 mM Tris pH8, 500 mM NaCl, 15 mM $MgCL_2$, 1% Triton X-100). The cells were incubated at room temperature for 5 minutes and then transferred to a new 96-well plate. The cells were further incubated at 30 minutes at 56° C. and for 10 minutes at 98° C. 5 µL of lysate was used for PCR analysis.

Figure 6:
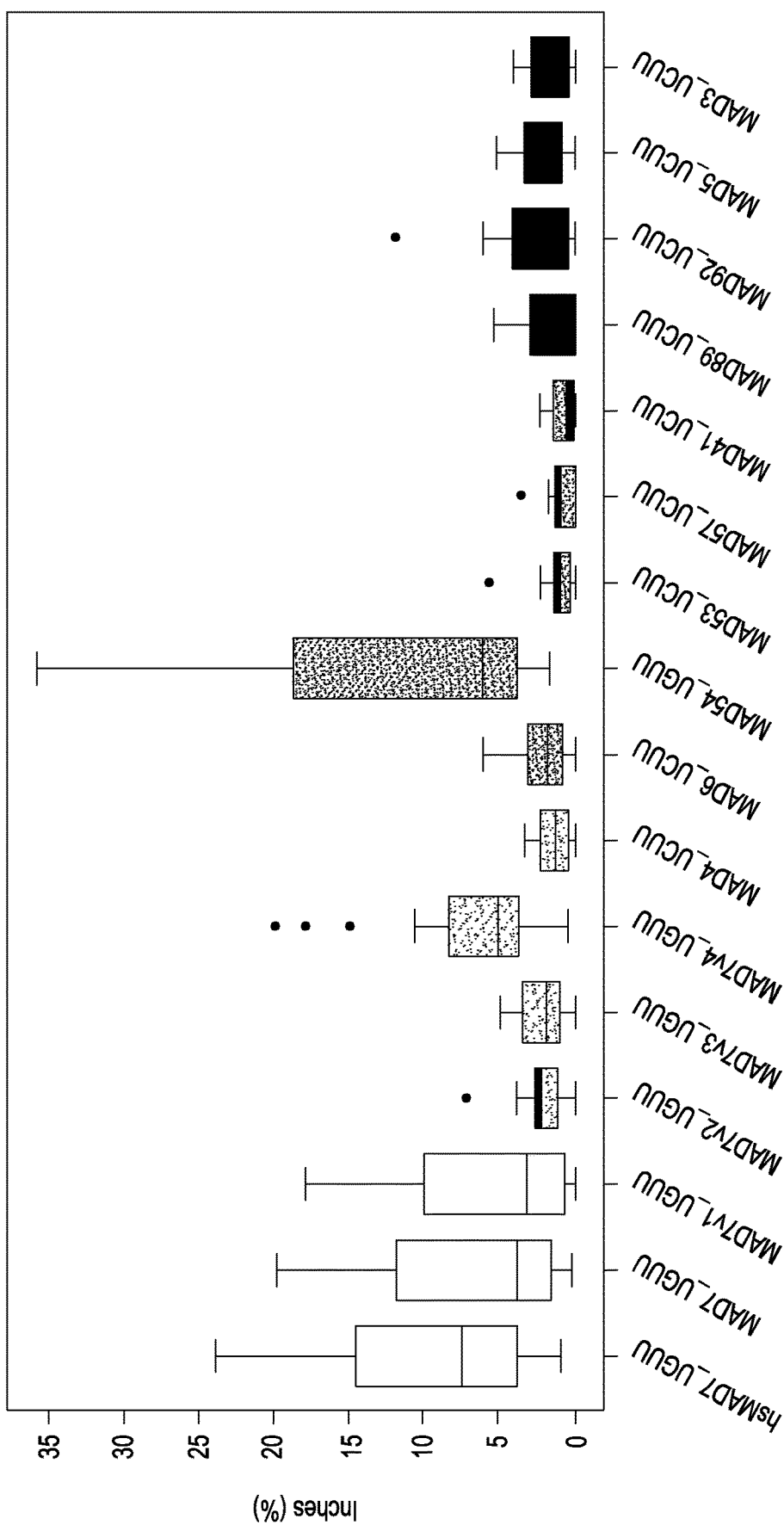
FIG. 6 shows the rate of indels induced by site-directed nuclease cleavage of HEK293T human cells induced by the indicated nuclease with the indicated variable loop.

FIG. 6 shows the rate of indels induced by site-directed nuclease cleavage in HEK293T human cells induced by the indicated nuclease with the indicated variable loop. hsMAD7 is the human codon-optimized nucleotide sequence [SEQ ID No. 53], while MAD7 indicates the broad-spectrum codon usage nucleotide sequence used in the E. coli and S. cerevisiae studies [SEQ ID No. 1].

TABLE 8

MAD7 Sequences

| Sequence and SEQ ID No. | Sequence | |
|---|---|---|
| MAD7 Native sequence Eubacterium rectale SEQ ID No. 1 | ATGAACAACG GCACAAATAA TTTTCAGAAC TTCATCGGGA TCTCAAGTTT GCAGAAAACG | 60 |
| | CTGCGCAATG CTCTGATCCC CACGGAAACC ACGCAACAGT TCATCGTCAA GAACGGAATA | 120 |
| | ATTAAAGAAG ATGAGTTACG TGGCGAGCAC CGCCAGATTC TGAAAGATAT CATGGATGAC | 180 |
| | TACTACCGCG GATTCATCTC TGAGACTCTG AGTTCTATTG ATGACATAGA TTGGACTAGC | 240 |
| | CTGTTCGAAA AAATGGAAAT TCAGCTGAAA AATGGTGATA ATAAAGATAC CTTAATTAAG | 300 |
| | GAACAGACAG AGTATCGGAA AGCAATCCAT AAAAAATTTG CGAACGACGA TCGGTTTAAG | 360 |
| | AACATGTTTA GCGCCAAACT GATTAGTGAC ATATTACCTG AATTTGTCAT CCACAACAAT | 420 |
| | AATTATTCGG CATCAGAGAA AGAGGAAAAA ACCCAGGTGA TAAAATTGTT TTCGCGCTTT | 480 |
| | GCGACTAGCT TTAAAGATTA CTTCAAGAAC CGTGCAAATT GCTTTTCAGC GGACGATATT | 540 |
| | TCATCAAGCA GCTGCCATCG CATCGTCAAC GACAATGCAG AGATATTCTT TTCAAATGCG | 600 |
| | CTGGTCTACC GCCGGATCGT AAAATCGCTG AGCAATGACG ATATCAACAA AATTTCGGGC | 660 |
| | GATATGAAAG ATTCATTAAA AGAAATGAGT CTGGAAGAAA TATATTCTTA CGAGAAGTAT | 720 |
| | GGGGAATTTA TTACCCAGGA AGGCATTAGC TTCTATAATG ATATCTGTGG GAAAGTGAAT | 780 |
| | TCTTTTATGA ACCTGTATTG TCAGAAAAAT AAAGAAAACA AAATTTATA CAAACTTCAG | 840 |
| | AAACTTCACA AACAGATTCT ATGCATTGCG GACACTAGCT ATGAGGTCCC GTATAAATTT | 900 |
| | GAAAGTGACG AGGAAGTGTA CCAATCAGTT AACGGCTTCC TTGATAACAT TAGCAGCAAA | 960 |
| | CATATAGTCG AAAGATTACG CAAAATCGGC GATAACTATA ACGGCTACAA CCTGGATAAA | 1020 |
| | ATTTATATCG TGTCCAAATT TTACGAGAGC GTTAGCCAAA AAACCTACCG CGACTGGGAA | 1080 |
| | ACAATTAATA CCGCCCTCGA AATTCATTAC AATAATATCT TGCCGGGTAA CGGTAAAAGT | 1140 |
| | AAAGCCGACA AAGTAAAAAA AGCGGTTAAG AATGATTTAC AGAAATCCAT CACCGAAATA | 1200 |
| | AATGAACTAG TGTCAAACTA TAAGCTGTGC AGTGACGACA ACATCAAAGC GGAGACTTAT | 1260 |
| | ATACATGAGA TTAGCCATAT CTTGAATAAC TTTGAAGCAC AGGAATTGAA ATACAATCCG | 1320 |
| | GAAATTCACC TAGTTGAATC CGAGCTCAAA GCGAGTGAGC TTAAAAACGT GCTGGACGTG | 1380 |
| | ATCATGAATG CGTTTCATTG GTGTTCGGTT TTTATGACTG AGGAACTTGT TGATAAAGAC | 1440 |
| | AACAATTTTT ATGCGGAACT GGAGGAGATT TACGATGAAA TTTATCCAGT AATTAGTCTG | 1500 |
| | TACAACCTGG TTCGTAACTA CGTTACCCAG AAACCGTACA GCACGAAAAA GATTAAATTG | 1560 |
| | AACTTTGGAA TACCGACGTT AGCAGACGGT TGGTCAAAGT CCAAAGAGTA TTCTAATAAC | 1620 |

TABLE 8-continued

MAD7 Sequences

| Sequence and SEQ ID No. | Sequence | |
|---|---|---|
| | GCTATCATAC TGATGCGCGA CAATCTGTAT TATCTGGGCA TCTTTAATGC GAAGAATAAA | 1680 |
| | CCGGACAAGA AGATTATCGA GGGTAATACG TCAGAAAATA AGGGTGACTA CAAAAAGATG | 1740 |
| | ATTTATAATT TGCTCCCGGG TCCCAACAAA ATGATCCCGA AAGTTTTCTT GAGCAGCAAG | 1800 |
| | ACGGGGGTGG AAACGTATAA ACCGAGCGCC TATATCCTAG AGGGGTATAA ACAGAATAAA | 1860 |
| | CATATCAAGT CTTCAAAAGA CTTTGATATC ACTTTCTGTC ATGATCGAT CGACTACTTC | 1920 |
| | AAAAACTGTA TTGCAATTCA TCCCGAGTGG AAAAACTTCG GTTTTGATTT TAGCGACACC | 1980 |
| | AGTACTTATG AAGACATTTC CGGGTTTTAT CGTGAGGTAG AGTTACAAGG TTACAAGATT | 2040 |
| | GATTGGACAT ACATTAGCGA AAAAGACATT GATCTGCTGC AGGAAAAAGG TCAACTGTAT | 2100 |
| | CTGTTCCAGA TATATAACAA AGATTTTTCG AAAAAATCAA CCGGGAATGA CAACCTTCAC | 2160 |
| | ACCATGTACC TGAAAAATCT TTTCTCAGAA GAAAATCTTA AGGATATCGT CCTGAAACTT | 2220 |
| | AACGGCGAAG CGGAAATCTT CTTCAGGAAG AGCAGCATAA AGAACCCAAT CATTCATAAA | 2280 |
| | AAAGGCTCGA TTTTAGTCAA CCGTACCTAC GAAGCAGAAG AAAAAGACCA GTTTGGCAAC | 2340 |
| | ATTCAAATTG TGCGTAAAAA TATTCCGGAA AACATTTATC AGGAGCTGTA CAAATACTTC | 2400 |
| | AACGATAAAA GCGACAAAGA GCTGTCTGAT GAAGCAGCCA AACTGAAGAA TGTAGTGGGA | 2460 |
| | CACCACGAGG CAGCGACGAA TATAGTCAAG GACTATCGCT ACACGTATGA TAAATACTTC | 2520 |
| | CTTCATATGC CTATTACGAT CAATTTCAAA GCCAATAAAA CGGGTTTTAT TAATGATAGG | 2580 |
| | ATCTTACAGT ATATCGCTAA AGAAAAAGAC TTACATGTGA TCGGCATTGA TCGGGGCGAG | 2640 |
| | CGTAACCTGA TCTACGTGTC CGTGATTGAT ACTTGTGGTA ATATAGTTGA ACAGAAAAGC | 2700 |
| | TTTAACATTG TAAACGGCTA CGACTATCAG ATAAAACTGA ACAACAGGA GGGCGCTAGA | 2760 |
| | CAGATTGCGC GGAAAGAATG GAAAGAAATT GGTAAAATTA AAGAGATCAA AGAGGGCTAC | 2820 |
| | CTGAGCTTAG TAATCCACGA GATCTCTAAA ATGGTAATCA AATACAATGC AATTATAGCG | 2880 |
| | ATGGAGGATT TGTCTTATGG TTTTAAAAAA GGGCGCTTTA AGGTCGAACG GCAAGTTTAC | 2940 |
| | CAGAAATTTG AAACCATGCT CATCAATAAA CTCAACTATC TGGTATTTAA AGATATTTCG | 3000 |
| | ATTACCGAGA ATGGCGGTCT CCTGAAAGGT TATCAGCTGA CATACATTCC TGATAAACTT | 3060 |
| | AAAAACGTGG GTCATCAGTG CGGCTGCATT TTTTATGTGC CTGCTGCATA CACGAGCAAA | 3120 |
| | ATTGATCCGA CCACCGGCTT TGTGAATATC TTTAAATTTA AAGACCTGAC AGTGGACGCA | 3180 |
| | AAACGTGAAT TCATTAAAAA ATTTGACTCA ATTCGTTATG ACAGTGAAAA AAATCTGTTC | 3240 |
| | TGCTTTACAT TTGACTACAA TAACTTTATT ACGCAAAACA CGGTCATGAG CAAATCATCG | 3300 |
| | TGGAGTGTGT ATACATACG CGTGCGCATC AAACGTCGCT TTGTGAACGG CCGCTTCTCA | 3360 |
| | AACGAAAGTG ATACCATTGA CATAACCAAA GATATGGAGA AAACGTTGGA ATGACGGAC | 3420 |
| | ATTAACTGGC GCGATGGCCA CGATCTTCGT CAAGACATTA TAGATTATGA AATTGTTCAG | 3480 |
| | CACATATTCG AAATTTTCCG TTTAACAGTG CAAATGCGTA ACTCCTTGTC TGAACTGGAG | 3540 |
| | GACCGTGATT ACGATCGTCT CATTTCACCT GTACTGAACG AAAATAACAT TTTTTATGAC | 3600 |
| | AGCGCGAAAG CGGGGGATGC ACTTCCTAAG GATGCCGATG CAAATGGTGC GTATTGTATT | 3660 |
| | GCATTAAAAG GGTTATATGA AATTAAACAA ATTACCGAAA ATTGGAAAGA AGATGGTAAA | 3720 |
| | TTTTCGCGCG ATAAACTCAA AATCAGCAAT AAAGATTGGT TCGACTTTAT CCAGAATAAG | 3780 |
| | CGCTATCTCT AA | |
| MAD7 human codon optimized sequence SEQ ID No. 2 | ATGAATAATG GCACTAACAA CTTTCAGAAT TTCATAGGCA TCAGTAGTCT CCAAAAGACG | 60 |
| | TTGCGCAACG CACTTATTCC AACCGAGACA ACTCAACAGT TCATCGTGAA GAATGGGATT | 120 |
| | ATTAAAGAGG ACGAACTCCG AGGAGAGACA CGGCAAATTC TTAAGGACAT CATGGACGAT | 180 |
| | TATTACAGAG GGTTTATTTC TGAGACATTA TCAAGTATTG ACGACATCGA CTGGACCTCA | 240 |
| | CTGTTCGAGA AGATGGAAAT TCAGTTGAAG AACGGAGACA CAAGGCACT TCTAATCAAG | 300 |
| | GAACAAACAG AGTACCGGAA AGCTATACAT AAGAAGTTTG CCAATGATGA CCGGTTTAAG | 360 |
| | AACATGTTCT CCGCGAAACT CATCAGCGAC ATTCTGCCAG AATTCGTGAT CCACAACAAT | 420 |
| | AACTATTCAG CCTCTGAGAA GGAGGAAAAG ACCCAGGTCA TCAAGCTTTT CTCTAGATTC | 480 |
| | GCCACTAGCT TCAAGGACTA TTTCAAGAAC CGCGCCAATT GTTTCTCTGC TGACGATATC | 540 |
| | TCCAGCAGCA GTTGCCATAG GATCGTGAAC GACAATGCTG AAATCTTCTT CTCTAATGCC | 600 |
| | CTTGTATACA GACGGATCGT GAAGTCACTG AGCAATGATG ACATTAACAA GATAAGCGGT | 660 |
| | GATATGAAAG ATAGTCTCAA GGAAATGTCA CTCGAAGAAA TTTATAGCTA CGAGAAATAC | 720 |
| | GGAGAGTTCA TCACCCAGGA GGGAATCAGT TTCTACAACG ATATTTGTGG CAAGGTAAAC | 780 |
| | TCCTTCATGA ATCTATATTG CCAGAAAAAC AAGGAGAATA AGAATCTTTA TAAGCTGCAG | 840 |
| | AAGTTACATA AGCAGATCCT GTGTATTGCA GATACGTCCT ATGAAGTGCC ATATAAGTTT | 900 |
| | GAGTCTGACG AGGAAGTGTA TCAATCCGTA AATGGGTTCC TCGACAACAT CAGCTCTAAG | 960 |
| | CATATAGTTG AACGACTTAG AAAGATAGGC GACAACTATA ATGGCTACAA CCTCGACAAG | 1020 |
| | ATTTATATAG TGTCCAAATT CTACGAGTCC GTATCCCAAA AGACATACAG AGATTGGGAA | 1080 |
| | ACAATCAATA CAGCCCTCGA AATCCACTAC AATAATATCC TACCCGGCAA TGGGAAATCC | 1140 |
| | AAGGCAGATA AGGTAAAGAA GGCAGTCAAG AACGACCTCC AGAAGTCCAT CACCGAGATT | 1200 |
| | AACGAACTGG TGAGCAATTA CAAACTCTGT AGTGACGATA ATATCAAGGC TGAGACGTAC | 1260 |
| | ATCCATGAGA TTTCACACAT ATTGAACAAC TTCGAAGCAC AGGAACTGAA GTACAATCCG | 1320 |
| | GAAATTCATC TCGTAGAATC CGAGCTTAAA GCCAGCGAGC TTAAGAACGT GCTCGATGTG | 1380 |
| | ATTATGAACG CGTTTCACTG GTGTAGTGTC TTCATGACTG AAGAATTAGT TGACAAGGAC | 1440 |
| | AACAATTTCT ATGCCGAACT GGAAGAAATT TACGATGAGA TCTATCCTGT TATCAGTCTG | 1500 |
| | TATAACCTCG TACGAACTA TGTGACCCAG AAGCCCTACT CGACCAAAAA GATCAAACTG | 1560 |
| | AACTTCGGCA TTCCAACCCT GGCCGATGGA TGGAGCAAAT CCAAAGAGTA CTCTAATAAC | 1620 |
| | GCTATCATTC TCATGCGAGA CAATCTCTAC TATCTCGGAA TATTCAATGC AAAGAATAAA | 1680 |
| | CCAGACAAAA AGATTATTGA AGGGAACACA TCCGAGAACA AGGTGATTA TAAGAAAATG | 1740 |
| | ATTTACAACC TGCTTCCAGG GCCCAATAAG ATGATTCCA GGTCTTTCT TTCAAGCAAG | 1800 |
| | ACTGGAGTTG AGACTTACAA GCCGTCCGCA TACATTCTCG AGGGCTATAA GCAGAACAAG | 1860 |
| | CACATTAAGA GCAGTAAAGA CTTTGATATC ACTTTCTGCC ATGATCTCAT TGACTACTTT | 1920 |
| | AAGAATTGTA TCGCTATTCA TCCGGAATGG AAGAACTTTG GATTTGACTT CAGCGATACA | 1980 |
| | AGTACCTACG AGGATATCTC TGGGTTCTAC CGGGAAGTGG AACTTCAGGG ATACAAGATC | 2040 |
| | GACTGGACAT ATATCTCTGA GAAAGACATC GATCTGCTGC AGGAGAAAGG CCAGCTGTAC | 2100 |
| | CTGTTCCAGA TTTATAATAA AGATTTCTCA AAGAAGAGCA CAGGAAACGA TAATCTTCAT | 2160 |
| | ACTATGTATC TGAAGAATCT CTTCTCCGAA GAGAACCTGA AGGATATCGT CCTCAAACTG | 2220 |

TABLE 8-continued

MAD7 Sequences

| Sequence and SEQ ID No. | Sequence | |
|---|---|---|
| | AACGGAGAAG CCGAGATTTT CTTCAGGAAG AGTAGTATTA AGAATCCCAT TATTCATAAG | 2280 |
| | AAAGGCTCCA TCTTGGTTAA CCGCACTTAC GAGGCTGAAG AGAAGGACCA GTTTGGAAAT | 2340 |
| | ATCCAAATCG TGAGGAAGAA TATTCCAGAG AATATCTACC AGGAACTGTA TAAGTACTTT | 2400 |
| | AATGATAAGA GCGATAAAGA ACTGAGCGAC GAGGCAGCGA AGTTGAAGAA TGTGGTGGGC | 2460 |
| | CATCACGAAG CTGCCACAAA CATTGTGAAA GACTATAGGT ACACATATGA TAAATACTTT | 2520 |
| | CTGCATATGC CTATAACCAT AAATTTCAAG GCCAATAAGA CTGGGTTCAT TAATGACCGC | 2580 |
| | ATCCTGCAGT ACATCGCTAA GGAGAAGGAC CTGCACGTCA TAGGGATCGA CCGCGGTGAA | 2640 |
| | CGGAATTTGA TTTATGTGTC CGTTATCGAT ACCTGCGGGA ATATCGTGGA GCAAAAGAGC | 2700 |
| | TTTAATATCG TCAATGGATA CGACTACCAG ATCAAGTTAA AGCAGCAAGA AGGCGCCAGG | 2760 |
| | CAAATCGCCA GGAAAGAGTG GAAAGAGATC GGCAAGATAA AGGAAATTAA GGAAGGCTAC | 2820 |
| | CTTTCCCTGG TCATCCATGA AATTAGTAAG ATGGTCATTA AGTACAATGC CATCATAGCA | 2880 |
| | ATGGAAGACT TAAGTTACGG ATTTAAGAAG GGAAGATTCA AAGTGGAAAG GCAGGTGTAT | 2940 |
| | CAGAAGTTTG AAACGATGCT AATAAACAAA CTTAATTATC TTGTGTTCAA AGACATTAGC | 3000 |
| | ATCACAGAGA ATGGAGGGCT TCTCAAGGGA TACCAACTGA CCTACATCCC AGATAAGCTT | 3060 |
| | AAGAACGTTG GCCACCAATG CGGCTGCATA TTCTACGTCC CGGCTGCTTA CACTTCTAAG | 3120 |
| | ATCGATCCAA CCACCGGCTT TGTGAATATC TTTAAGTTTA AAGACTTGAC CGTGGATGCT | 3180 |
| | AAGCGCGAGT TCATCAAGAA GTTTGACAGC ATCAGGTACG ACTCAGAAAA GAACCTCTTC | 3240 |
| | TGTTTCACAT TCGATTATAA CAACTTTATT ACTCAGAATA CTGTCATGAG TAAGTCATCC | 3300 |
| | TGGTCAGTGT ATACCTACGG AGTGAGGATC AAGCGAAGGT TTGTGAACGG CAGGTTTAGT | 3360 |
| | AATGAGTCTG ACACAATCGA TATTACCAAA GACATGGAGA AAACACTGGA GATGACAGAC | 3420 |
| | ATCAACTGGA GGGATGGACA TGACCTGCGC CAGGATATCA TAGATTACGA GATCGTGCAA | 3480 |
| | CATATATTCG AAATCTTTAG GCTGACAGTG CAGATGCGCA ACTCCCTGAG CGAGCTCGAA | 3540 |
| | GACAGAGATT ATGATAGACT AATCAGTCCG GTTCTGAACG AGAACAATAT CTTCTACGAT | 3600 |
| | AGTGCTAAGG CAGGAGACGC GCTGCCCAAG GACGCAGATG CCAATGGCGC GTATTGCATT | 3660 |
| | GCACTTAAAG GACTGTACGA AATTAAGCAG ATTACCGAGA ACTGGAAGGA GGACGGCAAG | 3720 |
| | TTTAGCAGGG ATAAGCTGAA GATTAGTAAC AAAGATTGGT TGACTTTAT ACAGAATAAG | 3780 |
| | CGTTATCTGT AA | 3792 |

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A coding sequence for a nucleic acid-guided nuclease comprising a nucleic acid sequence of any of SEQ ID Nos. 6, 13 or 18.

2. The coding sequence for the nucleic acid-guided nuclease of claim 1 comprising the nucleic acid sequence SEQ ID No. 6.

3. The coding sequence for the nucleic acid-guided nuclease of claim 2, wherein a compatible guide RNA to the nucleic-acid-guided nuclease has an optimal crRNA variable loop comprising UGUU.

4. The coding sequence for the nucleic acid-guided nuclease of claim 1 comprising the nucleic acid sequence SEQ ID No. 13.

5. The coding sequence for the nucleic acid-guided nuclease of claim 4, wherein a compatible guide RNA to the nucleic-acid-guided nuclease has an optimal crRNA variable loop comprising UCUU or UAUU.

6. The coding sequence for the nucleic acid-guided nuclease of claim 1 comprising the nucleic acid sequence SEQ ID No. 18.

7. The coding sequence for the nucleic acid-guided nuclease of claim 6, wherein a compatible guide RNA to the nucleic-acid-guided nuclease has an optimal crRNA variable loop comprising UAUU.

8. The coding sequence for a nucleic acid-guided nuclease of claim 1 for editing in bacteria.

9. The coding sequence for a nucleic acid-guided nuclease of claim 1 for editing in yeast.

10. The coding sequence for a nucleic acid-guided nuclease of claim 1 for editing in isolated mammalian cells.

* * * * *

SEQUENCE LISTING

<160> NUMBER OF SEQ ID NOS: 52

<210> SEQ ID NO 1
<211> LENGTH: 3792
<212> TYPE: DNA
<213> ORGANISM: Eubacterium rectale

<400> SEQUENCE: 1

| atgaacaacg gcacaaataa ttttcagaac ttcatcggga tctcaagttt gcagaaaacg | 60 |
|---|---|
| ctgcgcaatg ctctgatccc cacggaaacc acgcaacagt tcatcgtcaa gaacggaata | 120 |
| attaaagaag atgagttacg tggcgagaac cgccagattc tgaaagatat catggatgac | 180 |
| tactaccgcg gattcatctc tgagactctg agttctattg atgacataga ttggactagc | 240 |
| ctgttcgaaa aaatggaaat tcagctgaaa aatggtgata ataagatac cttaattaag | 300 |
| gaacagacag agtatcggaa agcaatccat aaaaaatttg cgaacgacga tcggtttaag | 360 |
| aacatgttta gcgccaaact gattagtgac atattacctg aatttgtcat ccacaacaat | 420 |
| aattattcgg catcagagaa agaggaaaaa acccaggtga taaaattgtt ttcgcgcttt | 480 |
| gcgactagct ttaaagatta cttcaagaac cgtgcaaatt gcttttcagc ggacgatatt | 540 |
| tcatcaagca gctgccatcg catcgtcaac gacaatgcag agatattctt ttcaaatgcg | 600 |

```
ctggtctacc gccggatcgt aaaatcgctg agcaatgacg atatcaacaa aatttcgggc      660
gatatgaaag attcattaaa agaaatgagt ctggaagaaa tatattctta cgagaagtat      720
ggggaattta ttacccagga aggcattagc ttctataatg atatctgtgg gaaagtgaat      780
tcttttatga acctgtattg tcagaaaaat aaagaaaaca aaaatttata caaacttcag      840
aaacttcaca aacagattct atgcattgcg acactagct atgaggtccc gtataaattt       900
```

Note: due to space, continuing:

```
gaaagtgacg aggaagtgta ccaatcagtt aacggcttcc ttgataacat tagcagcaaa      960
catatagtcg aaagattacg caaaatcggc gataactata acggctacaa cctggataaa     1020
atttatatcg tgtccaaatt ttacgagagc gttagccaaa aaacctaccg cgactgggaa     1080
acaattaata ccgccctcga aattcattac aataatatct gccgggtaa cggtaaaagt     1140 aaagccgaca aagtaaaaaa agcggttaag aatgatttac agaaatccat caccgaaata     1200
aatgaactag tgtcaaacta aagctgtgc agtgacgaca acatcaaagc ggagacttat      1260
atacatgaga ttagccatat cttgaataac tttgaagcac aggaattgaa atacaatccg     1320
gaaattcacc tagttgaatc cgagctcaaa gcgagtgagc ttaaaaacgt gctggacgtg     1380
atcatgaatg cgtttcattg gtgttcggtt tttatgactg aggaacttgt tgataaagac     1440 aacaatttt atgcggaact ggaggagatt tacgatgaaa tttatccagt aattagtctg     1500
tacaacctgg ttcgtaacta cgttacccag aaaccgtaca gcacgaaaaa gattaaattg     1560
aactttggaa taccgacgtt agcagacggt tggtcaaagt ccaaagagta ttctaataac     1620
gctatcatac tgatgcgcga caatctgtat tatctgggca tctttaatgc gaagaataaa     1680
ccggacaaga agattatcga gggtaatacg tcagaaaata agggtgacta caaaagatg     1740 atttataatt tgctcccggg tcccaacaaa atgatcccga aagttttctt gagcagcaag     1800 acggggtgg aaacgtataa accgagcgcc tatatcctag aggggtataa acagaataaa     1860
catatcaagt cttcaaaaga ctttgatatc actttctgtc atgatctgat cgactacttc     1920
aaaaactgta ttgcaattca tcccgagtgg aaaaacttcg gttttgattt tagcgacacc     1980
agtacttatg aagacatttc cgggttttat cgtgaggtag agttacaagg ttacaagatt     2040
gattggacat acattagcga aaaagacatt gatctgctgc aggaaaaagg tcaactgtat     2100
ctgttccaga tatataacaa agatttttcg aaaaaatcaa ccgggaatga caaccttcac     2160
accatgtacc tgaaaaatct tttctcagaa gaaaatctta aggatatcgt cctgaaactt     2220
aacggcgaag cggaaatctt cttcaggaag agcagcataa agaacccaat cattcataaa     2280
aaaggctcga ttttagtcaa ccgtacctac gaagcagaag aaaaagacca gtttggcaac     2340
attcaaattg tgcgtaaaaa tattccggaa acatttatc aggagctgta caaatacttc      2400
aacgataaaa gcgacaaaga gctgtctgat gaagcagcca aactgaagaa tgtagtggga     2460
caccacgagg cagcgacgaa tatagtcaag gactatcgct acacgtatga taaatacttc     2520
cttcatatgc ctattacgat caatttcaaa gccaataaaa cgggttttat taatgatagg     2580
atcttacagt atatcgctaa agaaaaagac ttacatgtga tcggcattga tcggggcgag     2640
cgtaacctga tctacgtgtc cgtgattgat acttgtggta atatagttga acagaaaagc     2700
tttaacattg taaacggcta cgactatcag ataaaactga acaacagga gggcgctaga     2760 cagattgcgc ggaaagaatg gaaagaaatt ggtaaaatta aagagatcaa agagggctac     2820
ctgagcttag taatccacga gatctctaaa atggtaatca aatacaatgc aattatagcg     2880
atggaggatt tgtcttatgg ttttaaaaaa gggcgcttta aggtcgaacg gcaagtttac     2940
cagaaatttg aaaccatgct catcaataaa ctcaactatc tggtatttaa agatatttcg     3000
```

```
attaccgaga atggcggtct cctgaaaggt tatcagctga catacattcc tgataaactt    3060
aaaaacgtgg gtcatcagtg cggctgcatt ttttatgtgc ctgctgcata cacgagcaaa    3120
attgatccga ccaccggctt tgtgaatatc tttaaattta agacctgac agtggacgca     3180 aaacgtgaat tcattaaaaa atttgactca attcgttatg acagtgaaaa aaatctgttc    3240
tgctttacat ttgactacaa taactttatt acgcaaaaca cggtcatgag caaatcatcg    3300
tggagtgtgt atacatacgg cgtgcgcatc aaacgtcgct tgtgaacgg ccgcttctca     3360 aacgaaagtg ataccattga cataaccaaa gatatggaga aaacgttgga atgacggac    3420 attaactggc gcgatggcca cgatcttcgt caagacatta tagattatga aattgttcag    3480
cacatattcg aaattttccg tttaacagtg caaatgcgta actccttgtc tgaactggag    3540
gaccgtgatt acgatcgtct catttcacct gtactgaacg aaaataacat tttttatgac    3600
agcgcgaaag cggggatgc acttcctaag gatgccgatg caaatggtgc gtattgtatt    3660
gcattaaaag ggttatatga aattaaacaa attaccgaaa attggaaaga agatggtaaa    3720
ttttcgcgcg ataaactcaa aatcagcaat aaagattggt tcgactttat ccagaataag    3780
cgctatctct aa                                                       3792

<210> SEQ ID NO 2
<211> LENGTH: 3792
<212> TYPE: DNA
<213> ORGANISM: Artificial Sequence
<220> FEATURE:
<223> OTHER INFORMATION: Human codon-optimized MAD7

<400> SEQUENCE: 2
atgaataatg gcactaacaa ctttcagaat ttcataggca tcagtagtct ccaaaagacg      60
ttgcgcaacg cacttattcc aaccgagaca actcaacagt tcatcgtgaa gaatgggatt     120 attaagagg acgaactccg aggagagaac cggcaaattc ttaaggacat catggacgat      180
tattacagag ggtttatttc tgagacatta tcaagtattg acgacatcga ctggacctca     240
ctgttcgaga gatggaaaat tcagttgaag aacggagaca caaggacac tctaatcaag      300 gaacaaacag agtaccggaa agctatacat aagaagtttg ccaatgatga ccggtttaag     360
aacatgttct ccgcgaaact catcagcgac attctgccag aattcgtgat ccacaacaat     420
aactattcag cctctgagaa ggaggaaaag acccaggtca tcaagctttt ctctagattc     480
gccactagct tcaaggacta tttcaagaac cgcgccaatt gtttctctgc tgacgatatc     540
tccagcagca gttgccatag gatcgtgaac gacaatgctg aaatcttctt ctctaatgcc     600
cttgtataca gacggatcgt gaagtcactg agcaatgatg acattaacaa gataagcggt     660
gatatgaaag atagtctcaa ggaaatgtca ctcgaagaaa tttatagcta cgagaaatac     720
ggagagttca tcacccagga gggaatcagt ttctacaacg atatttgtgg caaggtaaac    780
tccttcatga atctatattg ccagaaaaac aaggagaata gaatctttta aagctgcag     840 aagttacata agcagatcct gtgtattgca gatacctcct atgaagtgcc atataagttt    900
gagtctgacg aggaagtgta tcaatccgta aatgggttcc tcgacaacat cagctctaag    960
catatagttg aacgacttag aaagataggc gacaactata atggctacaa cctcgacaag   1020
atttatatag tgtccaaatt ctacgagtcc gtatcccaaa agacatacag agattgggaa    1080
acaatcaata cagcccctcga aatccactac aataatatcc tacccggcaa tgggaaatcc    1140
aaggcagata aggtaaagaa ggcagtcaag aacgacctcc agaagtccat caccgagatt    1200
```

```
aacgaactgg tgagcaatta caaactctgt agtgacgata atatcaaggc tgagacgtac    1260
atccatgaga tttcacacat attgaacaac ttcgaagcac aggaactgaa gtacaatccg    1320
gaaattcatc tcgtagaatc cgagcttaaa gccagcgagc ttaagaacgt gctcgatgtg    1380
attatgaacg cgtttcactg gtgtagtgtc ttcatgactg aagaattagt tgacaaggac    1440
aacaatttct atgccgaact ggaagaaatt tacgatgaga tctatcctgt tatcagtctg    1500
tataacctcg tacggaacta tgtgacccag aagccctact cgaccaaaaa gatcaaactg    1560
aacttcggca ttccaaccct ggccgatgga tggagcaaat ccaaagagta ctctaataac    1620
gctatcattc tcatgcgaga caatctctac tatctcggaa tattcaatgc aaagaataaa    1680
ccagacaaaa agattattga agggaacaca tccgagaaca aaggtgatta agaaaatg     1740 atttacaacc tgcttccagg gcccaataag atgattccca aggtcttct ttcaagcaag    1800 actggagttg agacttacaa gccgtccgca tacattctcg agggctataa gcagaacaag   1860
cacattaaga gcagtaaaga cttcgatatc actttctgcc atgatctcat tgactacttt   1920
aagaattgta tcgctattca tccggaatgg aagaactttg gatttgactt cagcgataca   1980
agtacctacg aggatatctc tgggttctac cgggaagtgg aacttcaggg atacaagatc   2040
gactggacat atatctctga gaaagacatc gatctgctgc aggagaaagg ccagctgtac   2100
ctgttccaga tttataataa agatttctca aagaagagca caggaaacga taatcttcat   2160
actatgtatc tgaagaatct cttctccgaa gagaacctga aggatatcgt cctcaaactg   2220
aacggagaag ccgagatttt cttcaggaag agtagtatta agaatcccat tattcataag   2280
aaaggctcca tcttggttaa ccgcacttac gaggctgaag agaaggacca gtttggaaat   2340
atccaaatcg tgaggaagaa tattccagag aatatctacc aggaactgta taagtacttt   2400
aatgataaga gcgataaaga actgagcgac gaggcagcga agttgaagaa tgtggtgggc   2460
catcacgaag ctgccacaaa cattgtgaaa gactataggt acacatatga taaatacttt   2520
ctgcatatgc ctataaccat aaatttcaag gccaataaga ctgggttcat taatgaccgc   2580
atcctgcagt acatcgctaa ggagaaggac ctgcacgtca tagggatcga ccgcggtgaa   2640
cggaatttga tttatgtgtc cgttatcgat acctgcggga atatcgtgga gcaaaagagc   2700
tttaatatcg tcaatggata cgactaccag atcaagttaa agcagcaaga aggcgccagg   2760
caaatcgcca ggaaagagtg gaaagagatc ggcaagataa aggaaattaa ggaaggctac   2820 cttttccctgg tcatccatga aattagtaag atggtcatta agtacaatgc catcatagca   2880
atggaagact taagttacgg atttaagaag ggaagattca aagtggaaag gcaggtgtat   2940
cagaagtttg aaacgatgct aataaacaaa cttaattatc ttgtgttcaa agacattagc   3000
atcacagaga atggagggct tctcaaggga taccaactga cctacatccc agataagctt   3060
aagaacgttg gccaccaatg cggctgcata ttctacgtcc cggctgctta cacttctaag   3120
atcgatccaa ccaccggctt tgtgaatatc tttaagttta aagacttgac cgtggatgct   3180
aagcgcgagt tcatcaagaa gtttgacagc atcaggtacg actcagaaaa gaacctcttc   3240
tgtttcacat tcgattataa caactttatt actcagaata ctgtcatgag taagtcatcc   3300
tggtcagtgt atacctacgg agtgaggatc aagcgaaggt ttgtgaacgg caggtttagt   3360
aatgagtctg acacaatcga tattaccaaa gacatggaga aaacactgga gatgacagac   3420
atcaactgga gggatggaca tgacctgcgc caggatatca tagattacga gatcgtgcaa   3480
catatattcg aaatctttag gctgacagtg cagatgcgca actccctgag cgagctcgaa   3540
gacagagatt atgatagact aatcagtccg gttctgaacg agaacaatat cttctacgat   3600
```

```
agtgctaagg caggagacgc gctgcccaag gacgcagatg ccaatggcgc gtattgcatt    3660
gcacttaaag gactgtacga aattaagcag attaccgaga actggaagga ggacggcaag    3720
tttagcaggg ataagctgaa gattagtaac aaagattggt ttgactttat acagaataag    3780
cgttatctgt aa                                                        3792

<210> SEQ ID NO 3
<211> LENGTH: 3792
<212> TYPE: DNA
<213> ORGANISM: Artificial Sequence
<220> FEATURE:
<223> OTHER INFORMATION: Variant MAD7 nucleic acid sequence

<400> SEQUENCE: 3
atgaacaacg gcacaaataa ttttcagaac ttcatcggga tctcaagttt gcagaaaacg      60
ctgcgcaatg ctctgatccc cacggaaacc acgaacagt tcatcgtcaa gaacggaata     120
attaaagaag atgagttacg tggcaaaaac cgccagattc tgaaagatat catggatgac    180
tactaccgcg gattcatctc tgagactctg agttctattg atgacataga ttggactagc    240
ctgttcgaaa aaatggaaat tcagctgaaa atggtgata taaagatac cttaattaag      300 gaacaggcgg agaaacggaa agcaatctat aaaaaatttg cggatgacga tcggtttaag    360
aacatgttta gcgccaaact gattagtgac atattacctg aatttgtcat ccacaacaat    420
aattattcgg catcagagaa aaaagaaaaa acccaggtga taaaattgtt ttcgcgcttt    480
gcgactagct ttaaagatta cttcaagaac cgtgcaaatt gcttttcagc ggacgatatt    540
tcatcaagca gctgccatcg catcgtcaac gacaatgcag agatattctt ttcaaatgcg    600
ctggtctacc gccggatcgt aaaaaacctg agcaatgacg atatcaacaa aatttcgggc    660
gatatgaaag attcattaaa agaaatgagt ctggaagaaa tatattctta cgagaagtat    720
ggggaattta ttacccagga aggcattagc ttctataatg atatctgtgg aaagtgaat    780 tcttttatga acctgtattg tcagaaaaat aaagaaaaca aaaatttata caaacttcgt    840
aaacttcaca aacagattct atgcattgcg gacactagct atgaggtccc gtataaattt    900
gaaagtgacg aggaagtgta ccaatcagtt aacggcttcc ttgataacat tagcagcaaa    960
catatagtcg aaagattacg caaaatcggc gataactata cgattacaa cctggataaa   1020 atttatatcg tgtccaaatt ttacgagagc gttagccaaa aaacctaccg cgactgggaa    1080
acaattaata ccgccctcga aattcattac aataatatct gccgggtaa cggtaaaagt    1140 aaagccgaca agtaaaaaaa gcggttaag aatgatttac agaaatccat caccgaaata    1200
aatgaactag tgtcaaacta aagctgtgc agtgacgaca catcaaagc ggagacttat     1260 atacatgaga ttagccatat cttgaataac tttgaagcac atgaattgaa atacaatccg    1320
gaaattcacc tagttgaatc cgagctcaaa gcgagtgagc ttaaaaacgt gctggacatt    1380
atcatgaatg cgtttcattg gtgttcggtt tttatgactg aggaacttgt tgataaagac    1440
aacaattttt atgcggaact ggaggagatt tacgatgaaa tttatccagt aattagtctg    1500
tacaacctgg ttcgtaacta cgttacccag aaaccgtaca gcacgaaaaa gattaaattg    1560
aactttggaa taccgacgtt agcagacggt tggtcaaagt ccaaagagta ttctaataac    1620
gctatcatac tgatgcgcga caatctgtat tatctgggca tctttaatgc gaagaataaa    1680
ccggacaaga agattatcga gggtaatacg tcagaaaata agggtgacta caaaagatg     1740 atttataatt tgctcccggg tcccaacaaa atgatcccga agttttctt gagcagcaag    1800
```

```
acggggtgg aaacgtataa accgagcgcc tatatcctag aggggtataa acagaataaa    1860
catctgaagt cttcaaaaga ctttgatatc actttctgtc atgatctgat cgactacttc    1920
aaaaactgta ttgcaattca tcccgagtgg aaaaacttcg gttttgattt tagcgacacc    1980
agtgcgtatg aagacatttc cgggttttat cgtgaggtag agttacaagg ttacaagatt    2040
gattggacat acattagcga aaaagacatt gatctgctgc aggaaaaagg tcaactgtat    2100
ctgttccaga tatataacaa agattttccg aaaaaatcaa ccgggaatga caaccttcac    2160
accatgtacc tgaaaaatct tttctcagaa gaaaatctta aggatatcgt cctgaaactt    2220
aacggcgaag cggaaatctt cttcaggaag agcagcataa agaacccaat cattcataaa    2280
aaaggctcga ttttagtcaa ccgtacctac gaagcagaag aaaaagacca gtttggcaac    2340
attcaaattg tgcgtaaaac cattccgaaa acatttatc aggagctgta caaatacttc    2400
aacgataaaa gcgacaaaga gctgtctgat gaagcagcca actgaagaa tgtagtggga    2460
caccacgagg cagcgacgaa tatagtcaag gactatcgct acacgtatga taaatacttc    2520
cttcatatgc ctattacgat caatttcaaa gccaataaaa cgagctttat taatgatagg    2580
atcttacagt atatcgctaa agaaaaagac ttacatgtga tcggcattga tcggggcgag    2640
cgtaacctga tctacgtgtc cgtgattgat acttgtggta atatagttga acagaaaagc    2700
tttaacattg taaacggcta cgactatcag ataaaactga acaacagga gggcgctaga    2760
cagattgcgc ggaaagaatg gaaagaaatt ggtaaaatta aagagatcaa agagggctac    2820
ctgagcttag taatccacga gatctctaaa atggtaatca aatacaatgc aattatagcg    2880
atggaggatt tgtcttatgg ttttaaaaaa gggcgcttta aggtcgaacg gcaagtttac    2940
cagaaatttg aaaccatgct catcaataaa ctcaactatc tggtatttaa agatatttcg    3000
attaccgaga atggcggtct cctgaaaggt tatcagctga catacattcc tgataaactt    3060
aaaaacgtgg gtcatcagtg cggctgcatt tttatgtgc ctgctgcata cacgagcaaa    3120
attgatccga ccaccggctt tgtgaatatc tttaaattta agacctgac agtggacgca    3180
aaacgtgaat tcattaaaaa atttgactca attcgttatg acagtgaaaa aaatctgttc    3240
tgctttacat ttgactacaa taactttatt acgcaaaaca cggtcatgag caaatcatcg    3300
tggagtgtgt atacatacgg cgtgcgcatc aaacgtcgct ttgtgaacgg ccgcttctca    3360
aacgaaagtg ataccattga cataaccaaa gatatggaga aaacgttgga atgacggac    3420
attaactggc gcgatggcca cgatcttcgt caagacatta tagattatga aattgttcag    3480
cacatattcg aaattttcaa attaacagtg caaatgcgta actccttgtc tgaactggag    3540
gaccgtgatt acgatcgtct catttcacct gtactgaacg aaaataacat ttttttatgac    3600
agcgcgaaag cggggtatgc acttcctaag gatgccgatg caaatggtgc gtattgtatt    3660
gcattaaaag ggttatatga aattaaacaa attaccgaaa attggaaaga agatggtaaa    3720
ttttcgcgcg ataaactcaa aatcagcaat aaagattggt tcgactttat ccagaataag    3780
cgctatctct aa                                                        3792
```

<210> SEQ ID NO 4
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 4

```
atgaacaacg gcacaaataa ttttcagaac ttcatcggga tctcaagttt gcagaaaacg    60
```

```
ctgcgcaatg ctctgacccc cacggaaacc acgcaacagt tcatcgtcaa gaacggaata    120 attaagaag atgagttacg tggcgagaac cgccagattc tgaaagatat catggatgac    180
tactaccgcg gattcatctc tgagactctg agttctattg atgacataga ttggactagc    240
ctgttcgaaa aaatgaaat tcagctgaaa atggtgata taaagatac cttaattaag    300 gaacaggcgg agaaacggaa agcaatctat aaaaaatttg cggatgacga tcggtttaag    360
aacatgttta gcgccaaact gattagtgac atattacctg aatttgtcat ccacaacaat    420
aattattcgg catcagagaa agaggaaaaa acccaggtga taaaattgtt ttcgcgcttt    480
gcgactagct ttaaagatta cttcaagaac cgtgcaaatt gcttttcagc ggacgatatt    540
tcatcaagca gctgccatcg catcgtcaac gacaatgcag agatattctt ttcaaatgcg    600
ctggtctacc gccggatcgt aaaaaacctg agcaatgacg atatcaacaa aatttcgggc    660
gatatgaaag attcattaaa aaaaatgagt ctggaaaaaa tatattctta cgagaagtat    720
ggggaattta tacccagga aggcattagc ttctataatg atatctgtgg aaagtgaat    780 tcttttatga acctgtattg tcagaaaaat aaagaaaaca aaatttata caaacttcgt    840 aaacttcaca aacagattct atgcattgcg gacactagct atgaggtccc gtataaattt    900
gaaagtgacg aggaagtgta ccaatcagtt aacggcttcc ttgataacat tagcagcaaa    960
catatagtcg aaagattacg caaaatcggc gataactata acggctacaa cctggataaa    1020
atttatatcg tgtccaaatt ttacgagagc gttagccaaa aaacctaccg cgactgggaa    1080
acaattaata ccgccctcga aattcattac aataatatct tgccgggtaa cggtaaaagt    1140
aaagccgaca agtaaaaaa agcggttaag aatgatttac agaaatccat caccgaaata    1200
aatgaactag tgtcaaacta taagctgtgc ccggacgaca acatcaaagc ggagacttat    1260
atacatgaga ttagccatat cttgaataac tttgaagcac aggaattgaa atacaatccg    1320
gaaattcacc tagttgaatc cgagctcaaa gcgagtgagc ttaaaaacgt gctggacgtg    1380
atcatgaatg cgtttcattg gtgttcggtt tttatgactg aggaacttgt tgataaagac    1440
aacaattttt atgcggaact ggaggagatt tacgatgaaa tttatccagt aattagtctg    1500
tacaacctgg ttcgtaacta cgttacccag aaaccgtaca gcacgaaaaa gattaaattg    1560
aactttggaa taccgacgtt agcagacggt tggtcaaagt ccaaagagta ttctaataac    1620
gctatcatac tgatgcgcga caatctgtat tatctgggca tctttaatgc gaagaataaa    1680
ccggaaaaga gattatcga gggtaatacg tcagaaaata agggtgacta caaaaagatg    1740
atttataatt tgctcccggg tcccaacaaa atgatcccga agttttctt gagcagcaag    1800 acggggggtgg aaacgtataa accgagcgcc tatatcctag aggggtataa acagaataaa    1860
catctgaagt cttcaaaaga ctttgatatc actttctgtc gtgatctgat cgactacttc    1920
aaaaactgta ttgcaattca tcccgagtgg aaaaacttcg gttttgattt tagcgacacc    1980
agtacttatg aagacatttc cgggtttat cgtgaggtag agttacaagg ttacaagatt    2040
gattggacat acattagcga aaagacatt gatctgctgc aggaaaaagg tcaactgtat    2100
ctgttccaga tatataacaa agattttcg aaaaatcaa ccgggaatga caaccttcac    2160
accatgtacc tgaaaaatct tttctcagaa gaaaatctta aggatgtggt cctgaaactt    2220
aacggcgaag cggaaatctt cttcaggaag agcagcataa agaacccaat cattcataaa    2280
aaaggctcga tttagtcaa ccgtacctac gaagcagaag aaaaagacca gtttggcaac    2340
attcaaattg tgcgtaaaac cattccggaa aacatttatc aggagctgta caaatacttc    2400
```

```
aacgataaaa gcgacaaaga gctgtctgat gaagcagcca aactgaagaa tgcggtggga    2460
caccacgagg cagcgacgaa tatagtcaag gactatcgct acacgtatga taaatacttc    2520
cttcatatgc ctattacgat caatttcaaa gccaataaaa cgagctttat taatgatagg    2580
atcttacagt atatcgctaa agaaaaagac ttacatgtga tcggcattga tcggggcgag    2640
cgtaacctga tctacgtgtc cgtgattgat acttgtggta atatagttga acagaaaagc    2700
tttaacattg taaacggcta cgactatcag ataaaactga acaacagga gggcgctaga    2760 cagattgcgc ggaaagaatg gaaagaaatt ggtaaaatta aagagatcaa agagggctac    2820
ctgagcttag taatccacga gatctctaaa atggtaatca aatacaatgc aattatagcg    2880
atggaggatt tgtcttatgg ttttaaaaaa gggcgcttta aggtcgaacg gcaagtttac    2940
cagaaatttg aaaccatgct catcaataaa ctcaactatc tggtatttaa agatatttcg    3000
attaccgaga atggcggtct cctgaaaggt tatcagctga catacattcc tgaaaaactt    3060
aaaaacgtgg gtcatcagtg cggctgcatt ttttatgtgc ctgctgcata cacgagcaaa    3120
attgatccga ccaccggctt tgtgaatatc tttaaattta aagacctgac agtggacgca    3180
aaacgtgaat tcattaaaaa atttgactca attcgttatg acagtgataa aaatctgttc    3240
tgctttacat ttgactacaa taactttatt acgcaaaaca cggtcatgag caaatcatcg    3300
tggagtgtgt atacatacgg cgtgcgcatc aaacgtcgct ttgtgaacgg ccgcttctca    3360
aacgaaagtg ataccattga cataaccaaa gatatggaga aaacgttgga atgacggac    3420 attaactggc gcgatggcca cgatcttcgt caagacatta tagattatga aattgttcag    3480
cacatattcg aaattttcaa attaacagtg caaatgcgta actccttgtc tgaactggag    3540
gaccgtaact acgatcgtct catttcacct gtactgaacg aaaataacat tttttatgac    3600
agcgcgaaag cggggatgc acttcctaag gatgccgatg caaatggtgc gtattgtatt    3660
gcattaaaag ggttatatga aattaaacaa attaccgaaa attggaaaga agatggtaaa    3720
ttttcgcgcg ataaactcaa aatcagcaat aaagattggt tcgactttat ccagaataag    3780
cgctatctct aa                                                        3792
```

<210> SEQ ID NO 5
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 5

```
atgaacaacg gcacaaataa ttttcagaac ttcatcggga tctcaagttt gcagaaaacg      60
ctgcgcaatg ctctgatccc cacggaaacc acgcaacagt tcatcgtcaa gaacggaata     120 attaagaag atgagttacg tggcgagaac cgccagattc tgaaagatat catggatgac     180
tactaccgcg gattcatctc tgagactctg agttctattg atgacataga ttggactagc     240
ctgttcgaaa aaatggaaat tcagctgaaa aatggtgata taaagataca cttaattaag     300
gaacaggcgg agaaacggaa agcaatctat aaaaaatttg cggatgacga tcggtttaag     360
aacatgttta gcgccaaact gattagtgac atattacctg aatttgtcat ccacaacaat     420
aattattcgg catcagagaa agaggaaaaa acccaggtga taaaattgtt ttcgcgcttt     480
gcgactagct ttaaagatta cttcaagaac cgtgcaaatt gcttttcagc ggacgatatt     540
tcatcaagca gctgccatcg catcgtcaac gacaatgcag agatattctt ttcaaatgcg     600
ctggtctacc gccggatcgt aaaaaaacctg agcaatgacg atatcaacaa aatttcgggc     660
```

```
gatatgaaag attcattaaa agaaatgagt ctggatgaaa tatattctta cgagaagtat      720
ggggaattta ttacccagga aggcattagc ttctataatg atatctgtgg gaaagtgaat      780
tcttttatga acctgtattg tcagaaaaat aaagaaaaca aaatttata caaacttcgt      840 aaacttcaca aacagattct atgcattgcg gacactagct atgaggtccc gtataaattt      900
gaaagtgacg aggaagtgta ccaatcagtt aacggcttcc ttgataacat tagcagcaaa      960
catatagtcg aaagattacg caaaatcggc gataactata acggctacaa cctggataaa     1020
atttatatcg tgtcccgttt ttacgagagc gttagccaaa aaacctaccg cgactgggaa     1080
acaattaata ccgccctcga aattcattac aataatatct tgccgggtaa cggtaaaagt     1140
aaagccgaca agtaaaaaaa agcggttaag aatgatttac agaaatccat caccgaaata     1200
aatgaactag tgtcaaacta taagctgtgc ccggacgaca acatcaaagc ggagacttat     1260
atacatgaga ttagccatat cttgaataac tttgaagcac aggaattgaa atacaatccg     1320
gaaattcacc tagttgaatc cgagctcaaa gcgagtgagc ttaaaaacgt gctggacgtg     1380
atcatgaatg cgtttcattg gtgttcggtt tttatgactg aggaacttgt tgataaagac     1440
aacaattttt atgcggaact ggaggagatt tacgatgaaa tttatccagt aattagtctg     1500
tacaacctgg ttcgtaacta cgttacccag aaaccgtaca gcacgaaaaa gattaaattg     1560
aactttggaa taccgacgtt agcagacggt tggtcaaagt ccaaagagta ttctaataac     1620
gctatcatac tgatgcgcga caatctgtat tatctgggca tctttaatgc gaagaataaa     1680
ccggacaaga agattatcga gggtaatacg tcagaaaata agggtgacta caaaagatg     1740 atttataatt tgctcccggg tcccaacaaa atgatcccga agttttctt gagcagcaag     1800 acggggtgg aaacgtataa accgagcgcc tatatcctag aggggtataa acagaataaa     1860
catctgaagt cttcaaaaga ctttgatatc actttctgtc gtgatctgat cgactacttc     1920
aaaaactgta ttgcaattca tcccgagtgg aaaaacttcg gttttgattt tagcgacacc     1980
agtacttatg aagacatttc cgggttttat cgtgaggtag agttacaagg ttacaagatt     2040
gattggacat acattagcga aaaagacatt gatctgctgc aggaaaaagg tcaactgtat     2100
ctgttccaga tatataacaa agatttttcg aaaaaatcaa ccgggaatga caaccttcac     2160
accatgtacc tgaaaaatct tttctcagaa gaaaatctta aggatatcgt cctgaaactt     2220
aacggcgaag cggaaatctt cttcaggaag agcagcataa agaacccaat cattcataaa     2280
aaaggctcga ttttagtcaa ccgtacctac gaagcagaag aaaaagacca gtttggcaac     2340
attcaaattg tgcgtaaaac cattccggaa acatttatc aggagctgta caaatacttc     2400
aacgataaaa gcgacaaaga gctgtctgat gaagcagcca aactgaagaa tgtagtggga     2460
caccacgagg cagcgacgaa tatagtcaag gactatcgct acacgtatga taaatacttc     2520
cttcatatgc ctattacgat caatttcaaa gccaataaaa cgagctttat taatgatagg     2580
atcttacagt atatcgctaa agaaaacgac ttacatgtga tcggcattga tcggggcgag     2640
cgtaacctga tctacgtgtc cgtgattgat acttgtggta atatagttga acagaaaagc     2700
tttaacattg taaacggcta cgactatcag ataaaactga acaacagga gggcgctaga     2760 cagattgcgc ggaaagaatg gaaagaaatt ggtaaaatta aagagatcaa agagggctac     2820
ctgagcttag taatccacga gatctctaaa atggtaatca aatacaatgc aattatagcg     2880
atggaggatt tgtcttatgg ttttaaaaaa gggcgcttta aggtcgaacg gcaagtttac     2940
cagaaatttg aaaccatgct catcaataaa ctcaactatc tggtatttaa agatatttcg     3000
```

-continued

| | |
|---|---|
| attaccgaga atggcggtct cctgaaaggt tatcagctga catacattcc tgaaaaactt | 3060 |
| aaaaacgtgg gtcatcagtg cggctgcatt ttttatgtgc ctgctgcata cacgagcaaa | 3120 |
| attgatccga ccaccggctt tgcgaatatc tttaaattta agacctgac agtggacgca | 3180 |
| aaacgtgaat tcattaaaaa atttgactca attcgttatg acagtgaaaa aaatctgttc | 3240 |
| tgctttacat ttgactacaa taactttatt acgcaaaaca cggtcatgag caaatcatcg | 3300 |
| tggagtgtgt atacatacgg cgtgcgcatc aaacgtcgct ttgtgaacgg ccgcttctca | 3360 |
| aacgaaagtg ataccattga cataaccaaa gatatggaga aaacgttgga aatgacggac | 3420 |
| attaactggc gcgatggcca cgatcttcgt caagacatta tagattatga aattgttcag | 3480 |
| cacatattcg aaattttcaa attaacagtg caaatgcgta actccttgtc tgaactggag | 3540 |
| gaccgtgatt acgatcgtct catttcacct gtactgaacg aaataacat tttttatgac | 3600 |
| agcgcgaaag cggggatgc acttcctaag gatgccgatg caaatggtgc gtattgtatt | 3660 |
| gcattaaaag ggttatatga aattaaacaa attaccgaaa attggaaaga agatggtaaa | 3720 |
| ttttcgcgcg ataaactcaa aatcagcaat aaagattggt tcgactttat ccagaataag | 3780 |
| cgctatctct aa | 3792 |

<210> SEQ ID NO 6
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 6

| | |
|---|---|
| atgaacaacg gcacaaataa ttttcagaac ttcatcggga tctcaagttt gcagaaaacg | 60 |
| ctgcgcaatg ctctgatccc cacggaaacc acgcaacagt tcatcgtcaa gaacggaata | 120 |
| attaaagaag atgagttacg tggcgagaac cgccagattc tgaaagatat catggatgac | 180 |
| tactaccgcg gattcatctc tgagactctg agttctattg atgacataga ttggactagc | 240 |
| ctgttcgaaa aaatggaaat tcagctgaaa aatggtgata taaagatac cttaattaag | 300 |
| gaacaggcgg agaaacggaa agcaatctat aaaaaatttg cggatgacga tcggtttaag | 360 |
| aacatgtta gcgccaaact gattagtgac atattacctg aatttgtcat ccacaacaat | 420 |
| aattattcgg catcagagaa agaggaaaaa acccaggtga taaaattgtt ttcgcgcttt | 480 |
| gcgactagct ttaaagatta cttcaagaac cgtgcaaatt gcttttcagc ggacgatatt | 540 |
| tcatcaagca gctgccatcg catcgtcaac gacaatgcag agatattctt ttcaaatgcg | 600 |
| ctggtctacc gccggatcgt aaaaaacctg agcaatgacg atatcaacaa atttcgggc | 660 |
| gatatgaaag attcattaaa agaaatgagt ctggaagaaa tatattctta cgagaagtat | 720 |
| ggggaattta ttacccagga aggcattagc ttctataatg atatctgtgg aaagtgaat | 780 |
| tcttttatga acctgtattg tcagaaaaat aagaaaaca aaatttata caaacttcgt | 840 |
| aaacttcaca acagattct atgcattgcg gacactagct atgaggtccc gtataaattt | 900 |
| gaaagtgacg aggaagtgta ccaatcagtt aacggcttcc ttgataacat tagcagcaaa | 960 |
| catatagtcg aaagattacg caaatcggc gataactata acggctacaa cctggataaa | 1020 |
| atttatatcg tgtccaaatt ttacgagagc gttagccaaa aaacctaccg cgactgggaa | 1080 |
| acaattaata ccgccctcga aattcattac aataatatct gccgggtaa cggtaaaagt | 1140 |
| aaagccgaca agtaaaaaa agcggttaag aatgatttac agaaatccat caccgaaata | 1200 |
| aatgaactag tgtcaaacta aagctgtgc agtgacgaca acatcaaagc ggagacttat | 1260 |

```
atacatgaga ttagccatat cttgaataac tttgaagcac aggaattgaa atacaatccg    1320
gaaattcacc tagttgaatc cgagctcaaa gcgagtgagc ttaaaaacgt gctggacgtg    1380
atcatgaatg cgtttcattg gtgttcggtt tttatgactg aggaacttgt tgataaagac    1440
aacaattttt atgcggaact ggaggagatt tacgatgaaa tttatccagt aattagtctg    1500
tacaacctgg ttcgtaacta cgttacccag aaaccgtaca gcacgaaaaa gattaaattg    1560
aactttggaa taccgacgtt agcagacggt tggtcaaagt ccaaagagta ttctaataac    1620
gctatcatac tgatgcgcga caatctgtat tatctgggca tctttaatgc gaagaataaa    1680
ccggacaaga agattatcga gggtaatacg tcagaaaata agggtgacta caaaaagatg    1740
atttataatt tgctcccggg tcccaacaaa atgatcccga agttttctt gagcagcaag     1800 acggggtgg aaacgtataa accgagcgcc tatatcctag aggggtataa acagaataaa     1860
catctgaagt cttcaaaaga ctttgatatc actttctgtc atgatctgat cgactacttc    1920
aaaaactgta ttgcaattca tcccgagtgg aaaaacttcg gttttgattt tagcgacacc    1980
agtacttatg aagacatttc cgggttttat cgtgaggtag agttacaagg ttacaagatt    2040
gattggacat acattagcga aaagacatt gatctgctgc aggaaaaagg tcaactgtat      2100
ctgttccaga tatataacaa agatttttcg aaaaaatcaa ccgggaatga caaccttcac    2160
accatgtacc tgaaaaatct tttctcagaa gaaaatctta aggatatcgt cctgaaactt    2220
aacggcgaag cggaaatctt cttcaggaag agcagcataa agaacccaat cattcataaa    2280
aaaggctcga tttagtcaa ccgtacctac gaagcagaag aaaaagacca gtttggcaac      2340
attcaaattg tgcgtaaaac cattccggaa acatttatc aggagctgta caaatacttc      2400
aacgataaaa gcgacaaaga gctgtctgat gaagcagcca aactgaagaa tgtagtggga    2460
caccacgagg cagcgacgaa tatagtcaag gactatcgct acacgtatga taaatacttc    2520
cttcatatgc ctattacgat caatttcaaa gccaataaaa cgagctttat taatgatagg    2580
atcttacagt atatcgctaa agaaaaagac ttacatgtga tcggcattga tcgggcgag     2640 cgtaacctga tctacgtgtc cgtgattgat acttgtggta atatagttga acagaaaagc    2700
tttaacattg taaacggcta cgactatcag ataaaactga acaacagga gggcgctaga    2760 cagattgcgc ggaaagaatg gaaagaaatt ggtaaaatta agagatcaa agagggctac     2820 ctgagcttag taatccacga gatctctaaa atggtaatca aatacaatgc aattatagcg    2880
atggaggatt tgtcttatgg ttttaaaaaa gggcgcttta aggtcgaacg gcaagtttac    2940
cagaaatttg aaaccatgct catcaataaa ctcaactatc tggtatttaa agatatttcg    3000
attaccgaga atggcggtct cctgaaaggt tatcagctga catacattcc tgataaactt    3060
aaaaacgtgg gtcatcagtg cggctgcatt ttttatgtgc ctgctgcata cacgagcaaa    3120
attgatccga ccaccggctt tgtgaatatc tttaaattta agacctgac agtggacgca     3180 aaacgtgaat tcattaaaaa atttgactca attcgttatg acagtgaaaa aaatctgttc    3240
tgctttacat ttgactacaa taactttatt acgcaaaaca cggtcatgag caaatcatcg    3300
tggagtgtgt atacatacgg cgtgcgcatc aaacgtcgct ttgtgaacgg ccgcttctca    3360
aacgaaagtg ataccattga cataaccaaa gatatggaga aaacgttgga atgacggac     3420 attaactggc gcgatggcca cgatcttcgt caagacatta tagattatga aattgttcag    3480
cacatattcg aaattttcaa attaacagtg caaatgcgta actccttgtc tgaactggag    3540
gaccgtgatt acgatcgtct catttcacct gtactgaacg aaaataacat tttttatgac    3600
```

```
agcgcgaaag cggggatgc acttcctaag gatgccgatg caaatggtgc gtattgtatt    3660
gcattaaaag ggttatatga aattaaacaa attaccgaaa attggaaaga agatggtaaa    3720
ttttcgcgcg ataaactcaa aatcagcaat aaagattggt tcgactttat ccagaataag    3780
cgctatctct aa                                                        3792
```

<210> SEQ ID NO 7
<211> LENGTH: 4005
<212> TYPE: DNA
<213> ORGANISM: Artificial Sequence
<220> FEATURE:
<223> OTHER INFORMATION: Modified MAD7 nucleic acid sequence

<400> SEQUENCE: 7

```
atgtcatcgc tcacgaaatt cactaacaaa tactctaaac agctcaccat taagaatgaa      60
ctcatcccag ttggcaaaac actggagaac atcaaagaga atggtctgat agatggcgac     120
gaacagctga atgagaatta tcagaaggcg aaaattattg tggatgattt tctgcgggac     180
ttcattaata aagcactgaa taatacgcag atcgggaact ggcgcgaact ggcggatgcc     240
cttaataaag aggatgaaga taacatcgag aaattgcagg ataaaattcg gggaatcatt     300
gtatccaaat ttgaaacgtt tgatctgttt agcagctatt ctattaagaa agatgaaaag     360
attattgacg acgacaatga tgttgaagaa gaggaactgg atctgggcaa gaagaccagc     420
tcatttaaat acatatttaa aaaaaacctg tttaagttag tgttgccatc ctacctgaaa     480 accacaaaacc aggacaagct gaagattatt agctcgtttg ataattttc aacgtacttc     540 cgcgggttct tgaaaaccg aaaaacatt tttaccaaga aaccgatctc acaagtatt     600 gcgtatcgca ttgttcatga taacttcccg aaattccttg ataacattcg ttgttttaat     660
gtgtggcaga cggaatgccc gcaactaatc gtgaaagcag ataactatct gaaaagcaaa     720
aatgttatag cgaaagataa aagtttggca aactatttta ccgtgggcgc gtatgactat     780
ttcctgtctc agaatggtat agatttttac aacaatatta taggtggact gccagcgttc     840
gccggccatg agaaaatcca aggtctcaat gaattcatca atcaagagtg ccaaaaagac     900
agcgagctga aaagtaagct gaaaaaaccgt cacgcgttca aatggcggt actgttcaaa     960 cagatactca gcgatcgtga aaaagttttt gtaattgatg agttcgagtc ggatgctcaa    1020
gttattgacg ccgttaaaaa cttttacgcc gaacagtgca agataaacaa tgttattttt    1080
aacttattaa atcttatcaa gaatatcgct ttcttaagtg atgacgaact ggacggcata    1140
ttcattgaag ggaaatacct gtcgagcgtt agtcaaaaac tctatagcga ttggtcaaaa    1200
ttacgtaacg acattgagga tcggctaac tctaaacaag caataaaga gctggccaag    1260 aagatcaaaa ccaacaaggg ggatgtgaa aaagcgatct cgaaatatga gttctcgctg    1320
tcggaactga actcgattgt acatgataac accaagtttt ctgacctcct tagttgtaca    1380
ctgcataagg tggcttctga gaaactggtg aaggtcaatg aaggcgactg gccgaaacat    1440
ctcaagaata atgaagagaa acaaaaaatc aaagagccgc ttgatgctct gctggagatc    1500
tataatacac ttctgatttt taactgcaaa agcttcaata aaacggcaa cttctatgtc    1560 gactatgatc gttgcatcaa tgaactgagt tcggtcgtgt atctgtataa taaaacacgt    1620
aactattgca ctaaaaaacc ctataacacg gacaagttca aactcaatttt taacagtccg    1680 cagctcggtg aaggcttttc caagtcgaaa gaaaatgact gtctgactct ttgtttaaa    1740 aaagacgaca actattatgt aggcattatc cgcaaaggtg caaaaatcaa ttttgatgat    1800
acacaagcaa tcgccgataa caccgacaat tgcatcttta aaatgaatta tttcctactt    1860
```

```
aaagacgcaa aaaaatttat cccgaaatgt agcattcagc tgaaagaagt caaggcccat    1920
tttaagaaat ctgaagatga ttacattttg tctgataaag agaaatttgc tagcccgctg    1980
gtcattaaaa agagcacatt tttgctggca actgcacatg tgaaagggaa aaaaggcaat    2040
atcaagaaat tcagaaaga atattcgaaa gaaaacccca ctgagtatcg caattcttta    2100
aacgaatgga ttgcttttg taaagagttc ttaaaaactt ataaagcggc taccattttt    2160
gatataacca cattgaaaaa ggcagaggaa tatgctgata ttgtagaatt ctacaaggat    2220
gtcgataatc tgtgctacaa actggagttc tgcccgatta aacctcgtt tatagaaaac    2280 ctgatagata acggcgacct gtatctgttt cgcatcaata caaagactt cagcagtaaa    2340 tcgaccggca ccaagaacct tcatacgtta tatttacaag ctatattcga tgaacgtaat    2400
ctgaacaatc cgacaattat gctgaatggg ggagcagaac tgttctatcg taaagaaagt    2460
attgagcaga aaaccgtat cacacacaaa gccggttcaa ttctcgtgaa taaggtgtgt    2520
aaagacggta caagcctgga tgataagata cgtaatgaaa tttatcaata tgagaataaa    2580
tttattgata ccctgtctga tgaagctaaa aaggtgttac cgaatgtcat taaaaaggaa    2640
gctacccatg acattacaaa agataaacgt ttcactagtg acaaattctt ctttcactgc    2700
cccctgacaa ttaattataa ggaaggcgat accaagcagt tcaataacga agtgctgagt    2760
tttctgcgtg gaaatcctga catcaacatt atcggcattg accgcggaga gcgtaattta    2820
atctatgtaa cggttataaa ccagaaaggc gagattctgg attcggtttc attcaatacc    2880
gtgaccaaca agagttcaaa aatcgagcag acagtcgatt atgaagagaa attggcagtc    2940
cgcgagaaag agaggattga agcaaaacgt tcctgggact ctatctcaaa aattgcgaca    3000 ctaaggaag gttatctgag cgcaatagtt cacgagatct gtctgttaat gattaaacac    3060
aacgcgatcg ttgtcttaga gaatcttaat gcaggcttta agcgtattcg tggcggttta    3120
tcagaaaaaa gtgtttatca aaaattcgaa aaaatgttga ttaacaaact gaactatttt    3180
gtcagcaaga aggaatccga ctggaataaa ccgtctggtc tgctgaatgg actgcagctt    3240
tcggatcagt ttgaaagctt cgaaaaactg ggtattcagt ctggttttat tttttacgtg    3300
ccggctgcat atacctcaaa gattgatccg accacgggct tcgccaatgt tctgaatctg    3360
tcgaaggtac gcaatgttga tgcgatcaaa agcttttttt ctaacttcaa cgaaattagt    3420
tatagcaaga agaagcccct tttcaaattc tcattcgatc tggattcact gagtaagaaa    3480
ggctttagta gctttgtgaa atttagtaag agtaaatgga acgtctacac ctttggagaa    3540
cgtatcataa agccaaagaa taagcaaggt tatcggagg acaaaagaat caacttgacc    3600
ttcgagatga agaagttact taacgagtat aaggtttctt ttgatcttga aaataacttg    3660
attccgaatc tcacgagtgc caacctgaag gatacttttt ggaaagagct attctttatc    3720
ttcaagacta cgctgcagct ccgtaacagc gttactaacg gtaaagaaga tgtgctcatc    3780
tctccggtca aaaatgcgaa gggtgaattc ttcgtttcgg gaacgcataa caagactctt    3840
ccgcaagatt gcgatgcgaa cggtgcatac catattgcgt tgaaaggtct gatgatactc    3900
gaacgtaaca accttgtacg tgaggagaaa gatacgaaaa agattatggc gatttcaaac    3960
gtggattggt tcgagtacgt gcagaaacgt agaggcgttc tgtaa              4005
```

<210> SEQ ID NO 8
<211> LENGTH: 3717
<212> TYPE: DNA
<213> ORGANISM: Artificial Sequence
<220> FEATURE:

<223> OTHER INFORMATION: Modified MAD nuclease nucleic acid sequence

<400> SEQUENCE: 8

| | | | | | |
|---|---|---|---|---|---|
| atgaacaact | acgacgaatt | caccaaactg | tacccgatcc | agaaaaccat | ccgtttcgaa | 60 |
| ctgaaaccgc | agggtcgtac | catggaacac | ctggaaacct | tcaacttctt | cgaagaagac | 120 |
| cgtgaccgtg | cggaaaaata | caaaatcctg | aaagaagcga | tcgacgaata | ccacaaaaaa | 180 |
| ttcatcgacg | aacacctgac | caacatgtct | ctggactgga | actctctgaa | acagatctct | 240 |
| gaaaaatact | acaaatctcg | tgaagaaaaa | gacaaaaaag | ttttcctgtc | tgaacagaaa | 300 |
| cgtatgcgtc | aggaaatcgt | ttctgaattc | aaaaaagacg | accgtttcaa | agacctgttc | 360 |
| tctaaaaaac | tgttctctga | actgctgaaa | gagaaatct | acaaaaaagg | taaccaccag | 420 |
| gaaatcgacg | cgctgaaatc | tttcgacaaa | ttctctggtt | acttcatcgg | tctgcacgaa | 480 |
| aaccgtaaaa | acatgtactc | tgacggtgac | gaaatcaccg | cgatctctaa | ccgtatcgtt | 540 |
| aacgaaaact | tcccgaaatt | cctggacaac | ctgcagaaat | accaggaagc | gcgtaaaaaa | 600 |
| tacccggaat | ggatcatcaa | agcggaatct | gcgctggttg | cgcacaacat | caaaatggac | 660 |
| gaagttttct | ctctggaata | cttcaacaaa | gttctgaacc | aggaaggtat | ccagcgttac | 720 |
| aacctggcgc | tgggtggtta | cgttaccaaa | tctggtgaaa | aaatgatggg | tctgaacgac | 780 |
| gcgctgaacc | tggcgcacca | gtctgaaaaa | tcttctaaag | gtcgtatcca | catgaccccg | 840 |
| ctgttcaaac | agatcctgtc | tgaaaaagaa | tcttttctctt | acatcccgga | cgttttcacc | 900 |
| gaagactctc | agctgctgcc | gtctatcggt | ggtttcttcg | cgcagatcga | aaacgacaaa | 960 |
| gacggtaaca | tcttcgaccg | tgcgctggaa | ctgatctctt | cttacgcgga | atacgacacc | 1020 |
| gaacgtatct | acatccgtca | ggcggacatc | aaccgtgttt | ctaacgttat | cttcggtgaa | 1080 |
| tggggtaccc | tgggtggtct | gatgcgtgaa | tacaaagcgg | actctatcaa | cgacatcaac | 1140 |
| ctggaacgta | cctgcaaaaa | agttgacaaa | tggctggact | ctaaagaatt | cgcgctgtct | 1200 |
| gacgttctgg | aagcgatcaa | cgtaccggt | aacaacgacg | cgttcaacga | atacatctct | 1260 |
| aaaatgcgta | ccgcgcgtga | aaaaatcgac | gcggcgcgta | agaaatgaa | attcatctct | 1320 |
| gaaaaaatct | ctggtgacga | agaatctatc | cacatcatca | aaaccctgct | ggactctgtt | 1380 |
| cagcagttcc | tgcacttctt | caacctgttc | aaagcgcgtc | aggacatccc | gctggacggt | 1440 |
| gcgttctacg | cggaattcga | cgaagttcac | tctaaactgt | cgcgatcgt | tccgctgtac | 1500 |
| aacaaagttc | gtaactacct | gaccaaaaac | aacctgaaca | ccaaaaaaat | caaactgaac | 1560 |
| ttcaaaaacc | cgaccctggc | gaacggttgg | gaccagaaca | agtttacga | ctacgcgtct | 1620 |
| ctgatcttcc | tgcgtgacgg | taactactac | ctgggtatca | tcaacccgaa | acgtaaaaaa | 1680 |
| aacatcaaat | cgaacaggg | ttctggtaac | ggtccgttct | accgtaaaat | ggtttacaaa | 1740 |
| cagatcccgg | gtccgaacaa | aaacctgccg | cgtgttttcc | tgacctctac | caaaggtaaa | 1800 |
| aaagaataca | aaccgtctaa | agaaatcatc | gaaggttacg | aagcggacaa | acacatccgt | 1860 |
| ggtgacaaat | tcgacctgga | cttctgccac | aaactgatcg | acttcttcaa | agaatctatc | 1920 |
| gaaaaacaca | aagactggtc | taaattcaac | ttctacttct | ctccgaccga | atcttacggt | 1980 |
| gacatctctg | aattctacct | ggacgttgaa | aaacagggtt | accgtatgca | cttcgaaaac | 2040 |
| atctctgcgg | aaaccatcga | cgaatacgtt | gaaaaggtg | acctgttcct | gttccagatc | 2100 |
| tacaacaaag | acttcgttaa | agcggcgacc | ggtaaaaaag | acatgcacac | catctactgg | 2160 |
| aacgcggcgt | tctctccgga | aaacctgcag | gacgttgttg | ttaaactgaa | cggtgaagcg | 2220 |
| gaactgttct | accgtgacaa | atctgacatc | aaagaaatcg | ttcaccgtga | aggtgaaatc | 2280 |

```
ctggttaacc gtacctacaa cggtcgtacc ccggttccgg acaaaatcca caaaaaactg    2340
accgactacc acaacggtcg taccaaagac ctgggtgaag cgaaagaata cctggacaaa    2400
gttcgttact tcaaagcgca ctacgacatc accaaagacc gtcgttacct gaacgacaaa    2460
atctacttcc acgttccgct gaccctgaac ttcaaagcga acggtaaaaa aaacctgaac    2520
aaaatggtta tcgaaaaatt cctgtctgac gaaaaagcgc acatcatcgg tatcgaccgt    2580
ggtgaacgta acctgctgta ctactctatc atcgaccgtt ctggtaaaat catcgaccag    2640
cagtctctga cgttatcga cggtttcgac taccgtgaaa aactgaacca gcgtgaaatc    2700
gaaatgaaag acgcgcgtca gtcttggaac gcgatcggta aaatcaaaga cctgaaagaa    2760
ggttacctgt ctaaagcggt tcacgaaatc accaaaatgg cgatccagta caacgcgatc    2820
gttgttatgg aagaactgaa ctacggtttc aaacgtggtc gtttcaaagt tgaaaaacag    2880
atctaccaga aattcgaaaa catgctgatc gacaaaatga actacctggt tttcaaagac    2940
gcgccggacg aatctccggg tggtgttctg aacgcgtacc agctgaccaa cccgctggaa    3000
tctttcgcga aactgggtaa acagaccggt atcctgttct acgttccggc ggcgtacacc    3060
tctaaaatcg acccgaccac cggtttcgtt aacctgttca cacctcttc taaaaccaac    3120 gcgcaggaac gtaaagaatt cctgcagaaa ttcgaatcta tctcttactc tgcgaaagac    3180
ggtggtatct tcgcgttcgc gttcgactac cgtaaattcg gtacctctaa accgaccac    3240 aaaaacgttt ggaccgcgta caccaacggt gaacgtatgc gttacatcaa agaaaaaaaa    3300
cgtaacgaac tgttcgaccc gtctaaagaa atcaaagaag cgctgaccte ttctggtatc    3360 aaatacgacg gtggtcagaa catcctgccg gacatcctgc gttctaacaa caacggtctg    3420
atctacacca tgtactcttc tttcatcgcg gcgatccaga tgcgtgttta cgacggtaaa    3480
gaagactaca tcatctctcc gatcaaaaac tctaaaggtg aattcttccg taccgacccg    3540
aaacgtcgtg aactgccgat cgacgcggac gcgaacggtg cgtacaacat cgcgctgcgt    3600
ggtgaactga ccatgcgtgc gatcgcggaa aaattcgacc cggactctga aaaaatggcg    3660
aaactggaac tgaaacacaa agactggttc gaattcatgc agacccgtgg tgactaa     3717
```

<210> SEQ ID NO 9
<211> LENGTH: 3897
<212> TYPE: DNA
<213> ORGANISM: Artificial Sequence
<220> FEATURE:
<223> OTHER INFORMATION: Modified MAD nuclease nucleic acid sequence

<400> SEQUENCE: 9

```
atgactaaaa catttgattc agagtttttt aatttgtact cgctgcaaaa aacggtacgc     60
tttgagttaa aacccgtggg agaaaccgcg tcatttgtgg aagactttaa aaacgagggc    120
ttgaaacgtg ttgtgagcga agatgaaagg cgagccgtcg attaccagaa agttaaggaa    180
ataattgacg attaccatcg ggatttcatt gaagaaagtt taattatttt ccggaacag     240 gtgagtaaag atgctcttga gcaggcgttt catctttatc agaaactgaa ggcagcaaaa    300
gttgaggaaa gggaaaaagc gctgaaagaa tgggaagcgc tgcagaaaaa gctacgtgaa    360
aaagtggtga atgcttctc ggactcgaat aaagcccgct tctcaaggat tgataaaaag    420
gaactgatta aggaagacct gataaattgg ttggtcgccc agaatcgcga ggatgatatc    480
cctacggtcg aaacgtttaa caacttcacc acatatttta ccggcttcca tgagaatcgt    540
aaaaatattt actccaaaga tgatcacgcc accgctatta gctttcgcct tattcatgaa    600
```

-continued

```
aatcttccaa agttttttga caacgtgatt agcttcaata agttgaaaga gggtttccct      660
gaattaaaat ttgataaagt gaaagaggat ttagaagtag attatgatct gaagcatgcg      720
tttgaaatag aatatttcgt taacttcgtg acccaagcgg gcatagatca gtataattat      780
ctgttaggag ggaaaaccct ggaggacggg acgaaaaaac aagggatgaa tgagcaaatt      840
aatctgttca acaacagca acgcgagat aaagcgcgtc agattcccaa actgatcccc       900
ctgttcaaac agattcttag cgaaaggact gaaagccagt cctttattcc taaacaattt      960
gaaagtgatc aggagttgtt cgattcactg cagaagttac ataataactg ccaggataaa     1020
ttcaccgtgc tgcaacaagc cattctcggt ctggcagagg cggatcttaa gaaggtcttc     1080
atcaaaacct ctgatttaaa tgccttatct aacaccattt tcgggaatta cagcgtctttt    1140 tccgatgcac tgaacctgta taagaaagc ctgaaaacga aaaagcgca ggaggctttt       1200 gagaaactac cggcccattc tattcacgac ctcattcaat acttggaaca gttcaattcc     1260
agcctggacg cggaaaaaca acagagcacc gacaccgtcc tgaactactt catcaagacc     1320
gatgaattat attctcgctt cattaaatcc actagcgagg ctttcactca ggtgcagcct     1380
ttgttcgaac tggaagccct gtcatctaag cgccgcccac cggaatcgga agatgaaggg     1440 gcaaagggc aggaaggctt cgagcagatc aagcgtatta agcttacct ggatacgctt       1500 atggaagcgg tacactttgc aaagccgttg tatcttgtta agggtcgtaa aatgatcgaa     1560
gggctcgata aagaccagtc cttttatgaa gcgtttgaaa tggcgtacca agaacttgaa     1620
tcgttaatca ttcctatcta taacaaagcg cggagctatc tgtcgcggaa acctttcaag     1680
gccgataaat tcaagattaa ttttgacaac aacacgctac tgagcggatg ggatgcgaac     1740
aaggaaactg ctaacgcgtc cattctgttt aagaaagacg ggttatatta ccttggaatt     1800
atgccgaaag gtaagacctt tctctttgac tactttgtat cgagcgagga ttcagagaaa     1860
ctgaaacagc gtcgccagaa gaccgccgaa gaagctctgg cgcaggatgg tgaaagttac     1920
ttcgaaaaaa ttcgttataa actgttacca ggggcttcaa agatgttacc gaaagtctttt    1980 tttagcaaca aaaatattgg cttttacaac ccgtcggatg acattttacg cattcgcaac     2040
acagcctctc acaccaaaaa cgggaccct cagaaaggcc actcaaaagt tgagtttaac      2100
ctgaatgatt gtcataagat gattgatttc ttcaaatcat caattcagaa acacccggaa     2160
tgggggtctt ttggctttac gttttctgat accagtgatt ttgaagacat gagtgccttc     2220
taccgggaag tagaaaacca gggttacgta attagctttg acaaaatcaa agagacctat     2280
atacagagcc aggtggaaca gggtaatctc tacttattcc agatttataa caaggatttc     2340
tcgccctaca gcaaaggcaa accaaacctg catactctgt actggaaagc cctgtttgaa     2400
gaagcgaacc tgaataacgt agtggcgaag ttgaacggtg aagcggaaat cttcttccgt     2460
cgtcactcca ttaaggcctc tgataaagtt gtccatccgg caaatcaggc cattgataat     2520
aagaatccac acacggaaaa aacgcagtca acctttgaat atgacctcgt taaagacaaa     2580
cgctacacgc aagataagtt cttttttccac gtcccaatca gcctcaactt taaagcacaa     2640
ggggtttcaa agtttaatga taaagtcaat gggttcctca agggcaaccc ggatgtcaac     2700
attataggta tagacagggg cgaacgccat ctgcttact ttaccgtagt gaatcagaaa       2760
ggtgaaatac tggttcagga atcattaaat accttgatgt cggacaaagg gcacgttaat     2820
gattaccagc agaaactgga taaaaagaa caggaacgtg atgctgcgcg taaatcgtgg     2880
accacggttg agaacattaa agagctgaaa gaggggtatc taagccatgt ggtacacaaa     2940
ctggcgcacc tcatcattaa atataacgca atagtctgcc tagaagactt gaattttggc     3000
```

```
tttaaacgcg gccgcttcaa agtggaaaaa caagtttatc aaaaatttga aaaggcgctt    3060
atagataaac tgaattatct ggttttaaa gaaaaggaac ttggtgaggt agggcactac    3120
ttgacagctt atcaactgac ggccccgttc gaatcattca aaaaactggg caaacagtct    3180
ggcattctgt tttacgtgcc ggcagattat acttcaaaaa tcgatccaac aactggcttt    3240
gtgaacttcc tggacctgag atatcagtct gtagaaaaag ctaaacaact tcttagcgat    3300
tttaatgcca ttcgttttaa cagcgttcag aattactttg aattcgaaat tgactataaa    3360
aaacttactc cgaaacgtaa agtcggaacc caaagtaaat gggtaatttg tacgtatggc    3420
gatgtcaggt atcagaaccg tcggaatcaa aaaggtcatt gggagaccga agaagtgaac    3480
gtgaccgaaa agctgaaggc tctgttcgcc agcgattcaa aaactacaac tgtgatcgat    3540
tacgcaaatg atgataacct gatagatgtg attttagagc aggataaagc cagctttttt    3600
aaagaactgt tgtggctcct gaaacttacg atgaccttac gacattccaa gatcaaatcg    3660
gaagatgatt ttattctgtc accggtcaag aatgagcagg gtgaattcta tgatagtagg    3720
aaagccggcg aagtgtggcc gaaagacgcc gacgccaatg gcgcctatca tatcgcgctc    3780
aaagggcttt ggaatttgca gcagattaac cagtgggaaa aaggtaaaac cctgaatctg    3840
gctatcaaaa accaggattg gtttagcttt atccaagaga aaccgtatca ggaatga       3897
```

<210> SEQ ID NO 10
<211> LENGTH: 3708
<212> TYPE: DNA
<213> ORGANISM: Artificial Sequence
<220> FEATURE:
<223> OTHER INFORMATION: Modified MAD nuclease nucleic acid sequence

<400> SEQUENCE: 10

```
atgcatacag gcggtcttct tagtatggac gcgaaagagt tcacaggtca gtatccgttg      60
tcgaaaacat tacgattcga acttcggccc atcggccgca cgtgggataa cctggaggcc     120
tcaggctact tagcggaaga ccgccatcgt gccgaatgtt atcctcgtgc gaaagagtta     180
ttggatgaca ccatcgtgc cttcctgaat cgtgtgttgc cacaaatcga tatggattgg     240
cacccgattg cggaggcctt tgtaaggta cataaaaacc ctggtaataa agaacttgcc     300
caggattaca accttcagtt gtcaaagcgc cgtaaggaga tcagcgcata tcttcaggat     360
gcagatggct ataaaggcct gttcgcgaag cccgccttag acgaagctat gaaaattgcg     420
aaagaaaacg ggaacgaaag tgatattgag gttctcgaag cgtttaacgg ttttagcgta     480
tacttcaccg ttatcatga gtcacgcgag acatttata gcgatgagga tatggtgagc     540
gtagcctacc gaattactga ggataatttc ccgcgctttg tctcaaacgc tttgatcttt     600
gataaattaa cgaaagcca tccggatatt atctctgaag tatcgggcaa tcttggagtt     660
gatgacattg gtaagtactt tgacgtgtcg aactataaca atttttcttt ccaggccggt     720
atagatgact acaatcacat tattggcggc catacaaccg aagacggact gatacaagcg     780
tttaatgtcg tattgaactt acgtcaccaa aaagaccctg gctttgaaaa aattcagttc     840
aaacagctct acaaacaaat cctgagcgtg cgtaccagca aaagctacat cccgaaacag     900
tttgacaact ctaaggagat ggttgactgc atttgcgatt atgtcagcaa aatagagaaa     960
tccgaaacag tagaacgggc cctgaaacta gtccgtaata tcagttcttt cgacttgcgc    1020
gggatctttg tcaataaaaa gaacttgcgc atactgagca caaaactgat aggagattgg    1080
gacgcgatcg aaaccgcatt gatgcatagt tcttcatcag aaaacgataa gaaaagcgta    1140
```

```
tatgatagcg cggaggcttt tacgttggat gacatctttt caagcgtgaa aaaattttct    1200
gatgcctctg ccgaagatat tggcaacagg gcggaagaca tctgtagagt gataagtgag    1260 acggccccctt ttatcaacga tctgcgagcg gtggacctgg atagcctgaa cgacgatggt    1320
tatgaagcgg ccgtctcaaa aattcggag tcgctggagc cttatatgga tcttttccat    1380
gaactggaaa ttttctcggt tggcgatgag ttcccaaaat gcgcagcatt ttacagcgaa    1440
ctggaggaag tcagcgaaca gctgatcgaa attattccgt tattcaacaa ggcgcgttcg    1500
ttctgcaccc ggaaacgcta tagcaccgat aagattaaag tgaacttaaa attcccgacc    1560
ttggcggacg ggtgggacct gaacaaagag agagacaaca aagccgcgat tctgcggaaa    1620
gacggtaagt attatctggc aattctggat atgaagaaag atctgtcaag cattaggacc    1680
agcgacgaag atgaatccag cttcgaaaag atggagtata aactgttacc gagtccagta    1740
aaaatgctgc caaagatatt cgtaaaatcg aaagccgcta aggaaaaata tggcctgaca    1800
gatcgtatgc ttgaatgcta cgataaaggt atgcataagt cgggtagtgc gtttgatctt    1860
ggcttttgcc atgaactcat tgattattac aagcgttgta tcgcggagta cccaggctgg    1920
gatgtgttcg atttcaagtt tcgcgaaact tccgattatg ggtccatgaa agagttcaat    1980
gaagatgtgc ccggagccgg ttactatatg agtctgagaa aaattccgtg cagcgaagtg    2040
taccgtctgt tagacgagaa atcgatttat ctatttcaaa tttataacaa agattactct    2100
gaaaatgcac atggtaataa gaacatgcat accatgtact gggagggtct cttttccccg    2160
caaaacctgg agtcgcccgt tttcaagttg tcgggtgggg cagaactttt ctttcgaaaa    2220
tcctcaatcc ctaacgatgc caaaacagta caccgaaag gctcagtgct ggttccacgt    2280
aatgatgtta acgtcggcg tattccagat tcaatctacc gcgaactgac acgctatttt    2340
aaccgtggcg attgccgaat cagtgacgaa gccaaaagtt atcttgacaa ggttaagact    2400
aaaaaagcgg accatgacat tgtgaaagat cgccgcttta ccgtggataa aatgatgttc    2460
cacgtcccga ttgcgatgaa ctttaaggcg atcagtaaac cgaacttaaa caaaaaagtc    2520
attgatggca tcattgatga tcaggatctg aaaatcattg gtattgatcg tggcgagcgg    2580
aacttaattt acgtcacgat ggttgacaga aaagggaata tcttatatca ggattctctt    2640
aacatcctca atggctacga ctatcgtaaa gctctggatg tgcgcgaata tgacaacaag    2700
gaagcgcgtc gtaactggac taaagtggag ggcattcgca aaatgaagga aggctatctg    2760
tcattagcgg tctcgaaatt agcggatatg attatcgaaa ataacgccat catcgttatg    2820
gaggacctga ccacggatt caaagcgggc cgctcaaaga ttgaaaaaca agtttatcag    2880
aaatttgaga gtatgctgat taacaaactg gctatatgg tgttaaaaga caagtcaatt    2940
gaccaatcag gtggcgcgct gcatggatac cagctggcga accatgttac caccttagca    3000
tcagttggaa agcagtgtgg ggttatcttt tataccggg cagcgttcac tagtaaaata    3060
gatccgacca ctggtttcgc cgatctcttt gccctgagta acgttaaaaa cgtagcgagc    3120
atgcgtgaat tctttccaa aatgaaatct gtcatttatg ataaagctga aggcaaattc    3180
gcattcacct ttgattactt ggattacaac gtgaagagcg aatgtggtcg tacgctgtgg    3240
accgtttaca ccgttggtga gcgcttcacc tattcccgtg tgaaccgcga atatgtacgt    3300
aaagtcccca ccgatattat ctatgatgcc ctccagaaag caggcattag cgtcgaagga    3360
gacttaaggg acagaattgc cgaaagcgat ggcgatacgc tgaagtctat tttttacgca    3420
ttcaaatacg cgctagatat gcgcgttgag aatcgcgagg aagactacat tcaatcacct    3480
gtgaaaaatg cctctgggga attttttttgt tcaaaaaatg ctggtaaaag cctcccacaa    3540
```

<210> SEQ ID NO 11
<211> LENGTH: 3783
<212> TYPE: DNA
<213> ORGANISM: Artificial Sequence
<220> FEATURE:
<223> OTHER INFORMATION: Modified MAD nuclease nucleic acid sequence

<400> SEQUENCE: 11

```
gatagcgatg caaacggtgc atataacatt gccctgaaag gtattcttca attacgcatg    3600
ctgtctgagc agtacgaccc caacgcggaa tctattagac ttccgctgat aaccaataaa    3660
gcctggctga cattcatgca gtctggcatg aagacctgga aaaattag                 3708
```

```
atggatagtt taaaagattt tacgaatcta tatcccgtaa gcaaaactct tcgttttgaa      60
ctgaaacctg ttggaaaaac gttggagaat atcgagaaag cgggcatcct gaagaagac     120
gagcaccgtg ccgaaagcta caggcgtgtc aaaaagatta tcgatactta tcacaaagtg    180
ttcattgata gcagtctgga gaacatggca aaaatgggca tagaaaatga atcaaaagca    240
atgctgcaga gcttttgcga gctctacaag aaagatcacc gaacggaagg tgaagataaa    300
gcactggaca aaattcgcgc cgttcttcgc ggtctgattg ttggcgcgtt caccggcgtg    360
tgcggccgcc gtgaaaacac cgtgcagaac gaaaagtacg agtcgctgtt caagaaaaaa    420
ctgataaaag aaattttgcc tgactttgtg ctttcgaccg aagcggaatc cctgccattt    480
tctgtcgaag aagcgacccg cagcctgaaa gaatttgact cattcacaag ttactttgca    540
ggcttctacg aaaaccgtaa aacatcctac agcacgaagc cacagagcac ggctattgct    600
tatcgcctga ttcatgagaa cctgccgaag ttcatcgata catccttgt ttttcaaaaa     660
attaagagc cgattgcgaa agagttagaa catattcgag ctgacttttc tgcgggtggg     720
tacattaaaa aagatgagcg gctggaagac atcttcagtc taaactatta tatccacgtt    780
ctgtcgcagg caggcattga aaatataat gcgctgattg gtaagattgt cacagaaggc     840
gatggtgaga tgaaaggtct taatgaacat atcaatctgt ataaccagca gcgtggtcgc    900
gaagaccgtc tttccactgtt ccgcccactg tataaacaga tcctgtctga ccgggaacag    960
ctgtcctacc tgccggaaag ctttgaaag gatgaagagc tacttcgcgc attaaaggag    1020
ttttacgacc atattgcgga agacatttg ggtagaacgc agcaactgat gacgtcaatt    1080
tctgaatacg atctgagtag aatctacgtt aggaatgata gccagctgac cgatattagc    1140
aaaaaaatgc tgggcgactg gaacgctatc tatatggcac gtgaacgtgc atatgatcat    1200
gaacaagcac cgaaacgtat aaccgcgaaa tatgagcgtg atcgcattaa ggcgctaaag    1260
ggagaagaaa gcatctcact cgcaaacctg aactcctgta tcgctttctt agataacgtg    1320
cgcgattgtc gcgtcgacac gtatctgtca cccttgggc agaaagaggg tccacatggt    1380
ctgtctaacc tggtggaaaa tgtctttgcg agttaccatg aagcggaaca actgctgtct    1440
tttccatacc ccgaagaaaa caatctaata caggataaag ataacgtggt gttaatcaaa    1500
aacctgctgg acaacatcag cgatctgcaa cgtttcctga accttgtg gggtatgggt    1560
gacgagccag acaaagacga acgttttat ggtgagtata attatatacg tggcgcccttt    1620
gaccaagtta ttccgctgta taacaaagta cggaactatc tgacccgtaa gccatattct    1680
acccgtaaag tgaaactgaa cttttggcaac tcgcaactgc tgtcgggttg ggatcgtaac    1740
aaagaaaaag ataatagttg tgttatcctg cgtaagggca aaaatttta cctcgcgatt    1800
atgaacaaca gacacaagcg ttcatttgaa aataaggttc tgccggagta taagagggc    1860
```

```
gaaccgtact tcgagaaaat ggattataag ttcttaccag accctaataa gatgttaccg    1920
aaagtctttc tttcgaaaaa aggcatgaaa atctataagc cgtccccgaa attactcgaa    1980
cagtatgggc acgggaccca caagaaaggg gatacttta gcatggacga tctgcacgaa    2040
ctgatcgatt ttttaaaca ctccatcgaa gcccatgaag actggaaaca gtttgggttc    2100
aagttctctg atacagccac atacgagaat gtgtctagtt tttatcggga agtggaggat    2160
cagggctaca aacttagttt tcgtaaagtt tcagagagtt atgtttatag tttaattgat    2220
cagggaaaac tttacctgtt ccagatctac aacaaagatt tctcgccatg tagtaagggt    2280
accccgaatc tgcatacact ctattggaga atgttattcg atgagcgtaa cttagcggat    2340
gtcatttata aattggacgg gaaagcagag atcttttttc gtgaaaaatc actgaagaat    2400
gaccacccga ctcatccggc cgggaaaccg atcaaaaaaa atcccgcca gaaaaaagga    2460 gaagagtctc tgtttgaata tgatctggtg aaagaccgtc attacactat ggataaattt    2520
caatttcatg ttccaattac aatgaacttc aaatgttcgg cgggttccaa agtaaatgat    2580
atggtaaacg cccatattcg cgaagcgaaa gatatgcatg ttattggcat cgatagaggc    2640
gaaagaaacc tgctttatat ttgcgtaatt gacagccgtg gtaccattct ggaccagatc    2700
tctttaaaca ccatcaatga catcgattat cacgacctgt tggagtctcg ggacaaggac    2760
cgccagcagg agcgccgtaa ttggcagaca attgaaggca taaagaatt aaaacagggt    2820 tacctttccc aggccgtaca ccgcatagcg gaactgatgg tggcctacaa agccgtagtt    2880
gccctggaag acttgaatat ggggtttaaa cgtggccgtc aaaagtcga gagcagcgtg    2940 tatcagcaat ttgaaaaaca gttgattgac aagttgaatt atttggttga taaaaagaaa    3000
cgtccagaag atattggtgg cttactgcgt gcataccagt ttacggcacc ttttaagtcc    3060
ttcaaagaaa tgggtaaaca gaacgggttt ctgttttaca tcccggcctg gaatacatcc    3120
aacatcgatc ctaccaccgg gtttgtcaac ctgtttcatg cacaatatga aaacgtggat    3180
aaagcgaaga gttttttcca aaaattcgat agtatttcgt ataacccaaa aaagattgg    3240 tttgagtttg cgttcgatta taaaaatttt actaaaaagg ctgagggatc ccgcagtatg    3300
tggatcctct gcacccatgg cagtcgtatt aaaaattttc gtaattcgca aaagaatggc    3360
cagtgggact cggaagagtt tgccctgacc gaagcgttca atcgctgtt tgtacgctac    3420 gaaattgact acacagcaga tctgaaaaca gccatcgtcg atgaaaaaca gaaagatttt    3480
tttgtagatc tcctaaaact gttcaaactg actgttcaga tgcgcaattc ctggaaagag    3540
aaagacctgg attatctgat tagcccggta gccggtgctg atggacgatt tttcgatact    3600
cgtgaaggta acaaaagtct cccgaaagat gctgatgcca atggtgcata caatattgca    3660
ttaaaggggc tatgggcctt gcgacagatc cgccagacca cgcgaaggcgg caagctgaaa    3720 ttggccatat cgaataagga atggttacaa tttgttcagg aacgtagcta tgaaaaagat    3780
tga                                                                  3783
```

<210> SEQ ID NO 12
<211> LENGTH: 3923
<212> TYPE: DNA
<213> ORGANISM: Artificial Sequence
<220> FEATURE:
<223> OTHER INFORMATION: Modified MAD nuclease nucleic acid sequence

<400> SEQUENCE: 12

```
tgactcagtt tgagggtttt accaatctgt accaagtgtc aaaaaccctg cgttttgagt     60
taatacctca gggtaaaaca ctcaagcaca ttcaggagca aggtttcatc gaagaggaca    120
```

```
aagcgcgcaa tgaccattat aaagaactga aacccatcat tgaccgtatt tataaaacct    180
atgcagatca gtgcctgcag ctggtgcaac ttgattggga gaaccttagc gccgccatcg    240
acagttatcg taaagagaaa acagaagaaa cgcgtaacgc gttaatcgaa gaacaagcga    300
catatcgtaa cgctatccac gattacttta ttggtcgaac tgataatctg actgacgcta    360
tcaataaacg gcatgcggaa atctacaaag gtctattcaa agcggaacta tttaacggta    420
aggtcctgaa acaactgggg accgtaacga ccacagagca tgagaacgcc ctcctgcgct    480
ctttcgataa atttacgacc tattttctg gttttacga aaatcgtaag aacgtcttct    540
cagcggaaga cattagcacc gcgatcccgc atcggattgt tcaggataat tttccgaaat    600
ttaaggaaaa ctgccacatt tttacacgtt tgatcacagc cgtcccgagc ctgcgtgaac    660
acttcgaaaa cgttaaaaag gcgatcggca ttttcgtgtc aacgagcatc gaagaagtct    720
tcagcttccc tttttataac cagcttctga cacagacaca gattgacttg tacaaccaat    780
tgttaggagg catttccagg gaagctggca cagaaaaaat taaagggctg aatgaagtcc    840
ttaatttagc gattcagaaa aatgatgaga cggctcatat tattgcgtct ctgccgcacc    900
gatttatccc attattcaag caaattcttt ccgatcgcaa caccttatca ttcattttgg    960
aggaatttaa aagcgacgaa gaagtcatcc agtctttctg caaatacaaa acactgctgc   1020
gcaacgaaaa cgtgttggag accgccgaag ctctgttcaa cgagctcaac tctattgatc   1080
tgacccatat ctttatcagc cataagaaac tggaaacgat tcatcagcc ctgtgcgatc   1140 actgggatac actgcgtaat gctctttatg agcgtagaat ctcagagctg acgggcaaga   1200
ttacgaaaag tgcaaaagaa aaagtgcagc gctctctgaa gcacgaagat attaacctgc   1260
aggaaatcat cagtgctgca ggcaaggaac tctctgaagc gtttaaacag aagaccagcg   1320
aaattcttag tcatgctcac gctgcattag accagccgct gccgacgaca ctcaagaagc   1380
aagaagaaaa agaaatcctg aagagtcagc tggattctct tctgggattg tatcacttgc   1440
tcgattggtt tgcagttgat gagtccaatg aggtagatcc tgaatttagt gcgcgtctga   1500
ccggcattaa acttgaaatg gaaccgagcc tgagtttcta caataaagcg cgtaattacg   1560
cgaccaaaaa accttatagc gtggagaaat ttaaactgaa tttccagatg ccgaccctag   1620
cgtccgggtg ggacgtaaat aaagaaaaaa acaacggcgc cattctcttc gtgaaaaacg   1680
gtttatacta tcttggaatt atgccgaaac agaaggacg ttacaaggca ctgagcttcg   1740
aaccaacaga gaagacgtcc gaggggtttg ataagatgta ttacgattac tttccagatg   1800
cagccaaaat gatacctaaa tgctcaacac aattaaaagc ggttacagcg cattttcaaa   1860
cacataccac cccaattctt ctgtcgaata atttcattga gccccttgaa attacaaaag   1920
aaatttatga cttaaataat ccggaaaaag aaccgaaaaa gtttcaaacc gcctatgcga   1980
aaaaaaccgg cgaccagaaa ggataccgtg aagcgctgtg caaatggatc gactttaccc   2040
gcgatttcct tagtaaatat acgaaaaacca cgtcaatcga tttgagctca cttcgtcctt   2100
caagtcagta taaagattta ggcgaatact acgcagaatt aaatcccctg ttatatcaca   2160
tctcttttca acgtatcgcg gaaaagaaa tcatggacgc tgttgaaacg ggaaaactgt   2220
atctgtttca gatatacaat aaggattttg cgaaaggcca tcacggtaaa ccgaaccttc   2280
atacacttta ctggacagga ttattcagcc ctgagaattt ggcgaaaact tcgattaaat   2340
taaacggcca agcagaatta tttttatcggc cgaagagccg catgaagagg atggcccatc   2400
gcctgggaga aaaaatgctt aacaaaaaat tgaaagacca gaagacaccc attccggaca   2460
```

| | |
|---|---|
| ccctgtacca ggagctgtat gactatgtaa atcatcgctt gagccatgat ctgtctgacg | 2520 |
| aagcgcgtgc actgctccct aacgtcatca ccaaggaagt ttcacacgag atcatcaaag | 2580 |
| accgccgttt taccagcgat aaattctttt ttcacgtgcc gatcacatta aactaccagg | 2640 |
| cagctaactc tccgtctaaa ttcaaccaac gcgttaacgc gtatcttaaa gaacatccag | 2700 |
| agaccccgat tattggcatc gaccgtgggg agcgtaacct gatttatatt accgtgatag | 2760 |
| acagcacggg aaagatttta gagcagcgaa gccttaacac cattcagcag ttcgactatc | 2820 |
| aaaaaaaatt ggacaaccgt gaaaaggagc gtgttgcggc ccgtcaagct ggagtgtcg | 2880 |
| ttggaaccat taaagacctg aaacagggct atttatccca ggtaattcat gaaatagttg | 2940 |
| atttaatgat tcactatcag gcagtggttg tgctggagaa cctgaacttt ggctttaaat | 3000 |
| cgaagcgcac tggcatagct gaaaaggcgg tgtatcagca gttcgagaag atgctgatcg | 3060 |
| ataagctgaa ttgtctcgtc ctgaaagact acccagcaga aaaggtcggc ggtgtcctga | 3120 |
| acccttatca actgaccgac cagttcacct catttgcgaa gatgggcacc caatccggat | 3180 |
| ttctcttcta tgtgccggcc ccatatacct cgaagattga cccgttaaca ggctttgtgg | 3240 |
| atccgttcgt gtggaaaact atcaaaaacc acgaaagccg gaaacacttc ctggagggat | 3300 |
| tcgattttct gcactacgac gtaaaaaccg gggatttcat tctgcatttc aaaatgaatc | 3360 |
| gtaacctgtc attccagcgc gggcttcctg gctttatgcc ggcatgggat attgtgtttg | 3420 |
| aaaaaaacga aactcagttc gatgctaaag gcactccgtt catagctgga agagaatcg | 3480 |
| tcccagtcat agaaaaccat cgcttcaccg gtcgctatcg ggatttgtat ccggccaacg | 3540 |
| agctcattgc actgctggaa gaaaaaggca tcgtgtttag agatgggagt aacattcttc | 3600 |
| cgaaactcct ggaaaacgat gactcacacg ccattgacac tatggtggcc ctgattcgct | 3660 |
| ccgttttaca gatgcgcaat tccaacgcag cgacgggtga agattatatc aatagccctg | 3720 |
| tccgagactt gaacggcgtt tgctttgata gcaggttcca aaatccagaa tggccgatgg | 3780 |
| atgcggacgc caatggagcg tatcacatcg cgctgaaggg acaattactg ctgaaccacc | 3840 |
| tgaaagagtc aaaagactta aaattgcaga acggtatcag caatcaagat tggctggctt | 3900 |
| acattcaaga attacggaat taa | 3923 |

<210> SEQ ID NO 13
<211> LENGTH: 4212
<212> TYPE: DNA
<213> ORGANISM: Artificial Sequence
<220> FEATURE:
<223> OTHER INFORMATION: Modified MAD nuclease nucleic acid sequence

<400> SEQUENCE: 13

| | |
|---|---|
| atgctatttt ttatgtccac agatattacc aacaaaccga gagagaaagg cgtctttgat | 60 |
| aatttcacaa acttatacga gttcagtaag acgctaacct tcggcctcat tccacttaaa | 120 |
| tgggatgaca caagaaaat gatcgtcgaa gacgaagatt tctcggtcct gcgcaaatat | 180 |
| ggtgttattg aggaagataa acgcatcgcg gagagtatta agattgccaa gttctacctg | 240 |
| aacatcctgc atcgtgaact gattggcaaa gtcctgggta gcctgaaatt tgaaaagaag | 300 |
| aacctggaga attcgaccg tttgctgggc gaaatagaga gaataataa gaatgagaat | 360 |
| atatcggaag acaagaagaa gagataagg aagaacttca gaaggagtt gtctatcgcg | 420 |
| caggatatcc tgttaaagaa ggtgggtgaa gtgttcgaga gcaacggcag cggcattctg | 480 |
| agctccaaga attgtcttga tgagttgacc aaacgattta ctaggcaaga agtagataaa | 540 |
| ctgagaagag agaacaaaga tattggcgtt gaatacccag acgtagcata caggagaag | 600 |

```
gatgggaaag aggaaactaa atctttcttc gcgatggatg tgggttactt ggacgatttc     660
cataagaatc ggaaacagct atactctgtg aaaggaaaga agaatagcct gggcagacga     720
attctggaca acttcgagat cttctgcaag aataagaagt tgtacgagaa atacaagaat     780
ttggacatcg atttcagcga aatcgaacgg aacttcaatc tcacgctgga gaaagtgttc     840
gactttgaca attacaacga acgcctgact caagagggtt tagatgagta tgctaagatc     900
ctcggaggcg agagcaacaa acaggaacgc acggccaaca ttcacggcct aaaccaaatc     960
attaacttat acatccagaa gaaacagagt gaacagaaag ccgaacagaa ggaaactgga    1020
aagaagaaga tcaagtttaa taagaaagat tatccgacct tcacgtgctt acagaagcag    1080
atcctatcac aggtattccg caaggagatc atcattgaat cggaccgcga tttaattcgt    1140
gaactgaagt tctttgttga agagtctaaa gagaaggttg ataaagctag aggaattatc    1200
gaatttctgc tgaatcacga agagaatgat atcgatctgg ccatggtgta tctaccaaag    1260
tctaagatca acagctttgt gtataaagta ttcaaagagc tcaggatttt cttatctgtg    1320
tttcaggatg gcgcttccaa tctagacttc gtttcgttcg acaagatcaa gacccacctg    1380
gagaacaaca aacttactta caagatattc ttcaagaccc tgattaaaga gaaccatgat    1440
ttcgaatcgt tcttgatctt attacagcaa gaaatcgatc tgcttattga cggcggcgaa    1500
actgttactc ttggtgggaa gaaggagtcg attactagtc tggacgagaa gaagaataga    1560
ctgaaggaga agcttggctg gttcgaaggc aaagtccgcg agaatgagaa gatgaaagat    1620
gaagaggagg gcgagttctg cagcacggtt cttgcttatt cacaggcggt cctgaacata    1680
accaagcgtg ccgaaatatt ctggttgaat gagaagcaag acgcgaaagt tggcgaagat    1740
aacaaagata tgatattcta caagaaattt gacgagtttg ccgacgatgg cttcgcaccg    1800
ttcttctact ttgataaatt cggcaactac ctgaaacgcc gctccagaaa tacgaccaaa    1860
gaaatcaagt tacacttcgg caatgatgac ctgcttgaag ctgggatat gaacaaagaa    1920 cccgagtact ggtcattcat tctgagggat cgcaaccagt attatttagg tattgggaag    1980
aaagatggtg agatcttcca caagaagctt ggtaattctg tggaagcggt taaggaggca    2040
tatgagcttg agaatgaagc cgacttctac gaaaagatag actataaaca gttgaatatt    2100
gaccgattcg aaggtattgc ttttccgaag aagactaaga cagaggaagc gttcagacaa    2160
gtctgcaaga agagagcgga cgagttctta ggaggagata catacgagtt taagattctg    2220
ctggcgataa agaagaata tgatgacttc aaagctcgcc gccagaaaga gaaggattgg    2280
gactctaaat ttagcaaaga gaagatgagc aaattaattg aatattacat tacttgcctt    2340
ggcaagcgcg atgattggaa gagatttaac cttaactttc gacagccgaa agaatatgaa    2400
gaccgctccg acttcgtgcg gcacattcaa cgtcaggcat attggattga ccctcgtaaa    2460
gtaagtaaag attacgtgga caagaaagtc gccgaaggtg aaatgttcct cttcaaagtg    2520
cataataaag acttctatga cttcgaaaga aagagcgaag acaagaagaa tcacactgca    2580
aatttgttta cacagtatct gctggagctc ttctcttgcg agaatattaa gaacatcaaa    2640
tcgaaagact tgatcgaatc tatcttcgaa ctggatggta aggcggagat ccgtttcagg    2700
cccaagaccg atgacgtgaa attaaagata taccagaaga agggtaagga tgttacgtac    2760
gctgacaaac gtgatggcaa caaggagaag gaggtgattc agcacaggcg gttcgcgaaa    2820
gacgcattaa ccctccacct caagattagg ttaaactttg ggaagcacgt gaatctgttc    2880
gacttcaaca aactggttaa tacagaactg tttgccaaag tgccagtaaa gatccttggc    2940
```

-continued

```
atggatcgcg gtgagaataa cctgatctac tattgtttcc tggacgaaca tggtgagatt      3000
gagaatggga agtgcggaag tctgaaccgc gtcggagagc aaattattac gctggaagat      3060
gacaagaaag ttaaggagcc ggtcgattac ttccagcttc tggtagatcg tgaaggtcag      3120
cgagattggg aacaaaagaa ttggcagaag atgacccgta tcaaagactt aaagaaagcg      3180
tatttgggta atgttgtcag ctggatctct aaagaaatgc tgagcggtat taagaaggc      3240 gtggttacca tcggtgtact ggaggattta aactcgaact tcaagcggac gcgtttcttt      3300
cgagaacggc aggtctatca gggctttgag aaggcactag ttaataaatt gggttactta      3360
gtggataaga aatacgataa ctaccgtaat gtgtatcagt ttgctccaat cgttgatagc      3420
gttgaggaaa tggagaagaa caaacagatc ggcacccttg tgtatgtccc agcctcttac      3480
acctcaaaga tttgccctca tcctaaatgc ggttggcgcg agcgtctcta tatgaagaac      3540
tcagccagta aagagaagat cgtaggcctg ttaaagagcg acgggataaa gatctcctat      3600
gatcaaaaga tgaccgcttc tactttgaa tatcaatggg aacaggaaca taagagtgat       3660
ggaaagaaaa agaaatactc aggcgtagac aaagtcttct ctaatgtgag tcggatgcgc      3720
tgggatgtgg aacagaagaa atctattgac tttgtagatg gcaccgacgg cagcattacc      3780
aacaaactaa agagcctgtt gaaaggcaaa ggtattgagt tagacaacat caatcaacag      3840
attgttaatc agcagaaaga actgggagtg gagttctttc agagcatcat tttctacttc      3900
aatctgatta tgcagatccg taactacgac aaagagaagt caggctccga agcggactat      3960
atccagtgcc caagttgttt attcgattca cgcaaaccgg aaatgaacgg caaactgtca      4020
gcgatcacga acgagacgc aaacggcgcc tacaatattg cccgtaaagg cttcatgcag       4080
ctgtgtagga ttagagagaa tcctcaggaa cctatgaaac tgattaccaa ccgggagtgg      4140
gatgaagcag tgcgcgaatg ggacatctac tcagctgctc aaaagatccc ggttctttct      4200
gaggagaatt aa                                                          4212
```

<210> SEQ ID NO 14
<211> LENGTH: 3741
<212> TYPE: DNA
<213> ORGANISM: Artificial Sequence
<220> FEATURE:
<223> OTHER INFORMATION: Modified MAD nuclease nucleic acid sequence

<400> SEQUENCE: 14

```
atgttgaaga acgtaggcat cgatcgctta gatgtagaga aggacgtaa gaatatgtct        60 aaactggaga aattcaccaa ttgttattca ctgagcaaga cactgcgatt taaagcgatc      120
ccggtcggca agacccagga gaacatcgat aataaacgcc tgctggtgga agatgagaag      180
cgagctgagg attataaggg tgtaaagaaa ctgctggatc gctactatct cagtttcatt      240
aatgacgtgc tgcacagtat caagctgaag aacttgaaca actatatcag cttatttcga      300
aagaagaccc gtaccgagaa agagaataag gaattggaga atctggagat taatctacgt      360
aaagagatcg ctaaggcgtt caagggaat gagggatata atcgctgtt caagaaagat        420 attattgaaa caatcctgcc ggaattcctt gacgataaag acgagatcgc gctcgttaac      480
tcgttcaacg gctttaccac tgcattcacc ggtttctttg ataatcggga gaatatgttc      540
tcagaggaag ccaagagtac ctctattgcg ttcaggtgca ttaatgagaa tctgaccagg      600
tatatttcta atatggatat ctttgagaaa gtggatgcca tatttgacaa gcacgaagtg      660
caggaaatca aagagaagat actgaattca gattacgatg tggaagattt ctttgaaggc      720
gagttcttca actttgttct aacacaggaa ggaatcgatg tatacaacgc gatcatcggc      780
```

```
ggtttcgtca cggagtcagg agaaaagatt aagggtttga atgaatacat taatttgtac      840
aatcaaaaga ccaaacagaa actgccgaaa tttaaaccac tgtacaaaca ggtgctgtcc      900
gaccgcgaat cattaagttt ctatggcgaa gggtacacct ctgacgaaga agtcctagaa      960
gtatttcgta acacgctcaa caagaattct gaaatattct cgtctatcaa gaagctggag     1020
aaattattca agaactttga tgagtattcc agcgccggaa tcttcgtcaa gaacggccca     1080
gccatctcta caattagcaa agatatattt ggtgaatgga atgtcatccg cgataagtgg     1140
aatgccgagt acgatgatat ccacctcaag aagaaggcag ttgttactga gaaatacgaa     1200
gacgatcgcc gcaagtcctt caagaagatc ggtagcttct cgctggaaca gctgcaggaa     1260
tatgcagacg cggatttatc tgtagttgag aagcttaaag agattattat tcagaaggtc     1320
gatgaaatct ataaagtgta tggtagtagt gagaagctgt ttgatgccga cttcgtcctc     1380
gagaagtcac taaagaagaa cgatgcggtg gtggctatta tgaaagatct gctggattcc     1440
gtgaaatctt tcgagaacta tattaaggcg ttctttggcg aaggcaaaga gaccaatcgt     1500
gacgaaagtt tctatggcga tttcgtactc gcctatgata ttcttcttaa ggttgatcac     1560
atttacgatg cgattcgcaa ctacgtaact cagaaaccgt attctaaaga taagttcaaa     1620
ctgtacttcc agaatccgca gtttatgggc ggctgggata agacaaaga aaccgattac     1680 cgcgccacca tattgcgtta cggttccaaa tattatctgg cgattatgga caagaaatat     1740
gccaagtgcc tgcagaagat tgacaaggat gatgtaaacg gtaactacga aaagattaac     1800
tacaaactcc taccgggacc gaataagatg cttcccaaag tgttcttttc taagaagtgg     1860
atggcatatt ataacccaag tgaagatatt caaaagatct acaagaatgg cacgttcaag     1920
aaaggcgaca tgtttaattt gaatgattgt cacaaactga tagatttctt taaagactca     1980
atcagtcgct atcccaagtg gagtaacgca tacgatttca acttcagcga aaccgagaag     2040
tataaggata ttgcgggttt ctatcgcgag gtcgaagaac aaggctacaa agtttcattc     2100
gaatctgcgt caaagaagga ggtcgataaa ttggtggagg aagggaaact atatatgttt     2160
cagatctata ataaggactt ctctgacaag agccatggta ctccgaatt acacaccatg     2220 tacttcaaac tgctgttcga cgagaataac catggccaga ttcgactgag tggcggtgct     2280
gaattgttca tgcgtcgagc ttctctaaag aaagaagagc tggttgttca tcctgcgaat     2340
agtccgattg ccaacaagaa cccagataac ccgaaaaaga ctacaacttt atcttatgat     2400
gtgtacaagg acaaacgttt cagcgaagat cagtacgaac tgcatattcc aattgccatt     2460
aacaaatgtc ctaagaacat attcaagata aataccgagg tccgtgtact gctgaaacac     2520
gatgacaatc cgtatgtcat tggtattgac cgcggcgaac ggaacctgtt gtatattgtg     2580
gtagtggatg gtaaaggaaa tatcgtcgaa cagtattctc tgaatgaaat cataaataac     2640
ttcaacggca tccgcatcaa gaccgattac cattcactgc tggacaagaa ggagaaagaa     2700
agatttgagg cccgtcagaa ctggaccagc attgagaaca ttaaggaatt gaaagcaggt     2760
tatatctctc aagtggtcca taagatttgc gagttggtgg agaaatacga tgcggtgata     2820
gcgttagaag acctgaatag cggatttaag aactcaagag ttaaagtcga gaaacaagta     2880
tatcagaagt ttgagaaaat gcttatcgac aaattaaact acatggttga taagaaaagc     2940
aatccttgcg ccactggcgg tgcgcttaaa ggataccaga ttaccaataa attcgagtcg     3000
tttaagagta tgagcacgca gaacggcttc attttctaca tcccggcatg gttgacatcg     3060
aagattgatc catcaacggg attcgtgaat cttcttaaga ccaaatacac ttctatagct     3120
```

```
gattcgaaga aattcatctc ttcgttcgat cgtatcatgt acgtgcccga agaagatctg    3180
tttgaatttg ccctggatta taagaacttc tctcgcaccg atgccgatta catcaagaaa    3240
tggaaactgt acagttatgg taaccgcatc cgcatcttca gaaatcccaa gaagaacaat    3300
gtctttgatt gggaagaagt gtgtctgacc agtgcataca agagttatt taataaatac     3360 ggcatcaact atcagcaggg cgatatccgt gctttactgt gcgaacagtc tgacaaagcc    3420
ttctacagtt ccttcatggc gttaatgagc ttaatgcttc agatgcggaa ttcgatcacg    3480
ggacgcaccg acgtggactt cctgatcagc ccagtaaaga atagtgacgg gatcttctac    3540
gatagccgga actacgaagc acaagagaac gcaatcttac cgaagaacgc cgatgcgaac    3600
ggtgcttata atattgcccg gaaagtcctt tgggccattg gccagttcaa gaaagcggag    3660
gacgagaaac ttgacaaagt taagattgcg attagcaata agaatggct ggaatatgcg     3720 cagacgagtg tgaagcacta a                                              3741
```

<210> SEQ ID NO 15
<211> LENGTH: 3918
<212> TYPE: DNA
<213> ORGANISM: Artificial Sequence
<220> FEATURE:
<223> OTHER INFORMATION: Modified MAD nuclease nucleic acid sequence

<400> SEQUENCE: 15

```
atgaataaag cggccgataa ttacacgggc ggcaactatg atgagtttat cgcccttct      60 aaagttcaga agactctacg caatgagctg aaaccaactc cctttactgc cgagcacatc    120
aagcagcgtg gcattataag cgaagatgaa tatcgtgccc agcaatcatt ggagctcaag    180
aagatcgcgg atgaatatta ccgtaattat atcacacata agttaaacga tattaataat    240
ctggatttct acaacttgtt cgacgctatc gaagagaaat acaagaagaa tgacaaggat    300
aatagggaca aactggacct ggtggagaag agcaaacgtg gtgaaatcgc caagatgctg    360
agcgctgacg ataactttaa atccatgttt gaagcgaaac tgattactaa actgcttcct    420
gattatgtgg agcggaacta taccggcgaa gataaagaga aggctctgga acactggcg    480 ctatttaaag ggttcacgac atacttcaaa ggatacttca agactaggaa gaacatgttc    540
tcgggcgagg gtggagcaag ttctatctgc catcgtatag tgaacgtgaa cgcctccatc    600
ttctacgata acctgaagac attcatgcgc atccaagaga aagcgggcga tgaaatcgca    660
ttaatcgaag aggaactgac ggagaagttg gatggctggc gtctggaaca tatttctcg    720 cgtgactatt acaatgaagt ccttgcgcag aaaggaattg actactataa ccagatctgc    780
ggcgacatta taaacacat gaacctgtat tgccagcaga acaaatttaa agcgaatata    840
ttcaagatga tgaaattaca gaagcaaatt atgggtatca gcgagaaggt cttcgagatt    900
ccgccaatgt accagaacga tgaagaggtg tatgcttcgt ttaatgaatt tatttcccgc    960
cttgaggaag tcaaactgac cgatcgcctg cgtaatattc ttcagaacat caacatctac   1020
aacactgcta agatctatat caacgcgcgc tattacacca acgtcagtac ctatgtgtat   1080
ggcggttggg gggtgattga agcgcaatc gaacgctatc tgtgtaacac tattgcaggt   1140
aaaggccaat cgaaggtgaa gaaaatcgag aatgcaaaga aggataacaa attcatgagc   1200
gtcaaggagt tggattcaat tgtggccgaa tatgagccgg attactttaa tgctccttat   1260
attgacgacg atgataacgc agtgaaagtc ttcggtggtc agggtgtgtt aggatacttt   1320
aataagatga gtgagctgct tgctgacgtt agtttgtata ccatcgacta taactcgat    1380 gacagcctga tagagaacaa agaaagcgct ctccgcatta agaaacaatt ggatgacatc   1440
```

```
atgagtttat atcattggct acagacgttc attatcgatg aggttgttga gaaagacaat    1500
gccttctacg ccgaactgga ggatatttgc tgcgaactag agaacgtggt caccttgtat    1560
gataggattc gaaactacgt gacccgtaaa ccgtactcga cccagaaatt taagcttaac    1620
ttcgctagtc cgaccctggc atccggctgg agccgctcta aggaattcga taacaatgct    1680
atcattctgc tgcgtaataa taaatattac atcgcgatat tcaatgttaa caataaacca    1740
gataaacaga tcatcaaggg cagcgaagaa caacgcttgt caacagatta taagaagatg    1800
gtttacaacc tactgcccgg tccaaataag atgttgccga aggtgtttat caaatccgac    1860
acgggcaaac gtgattataa cccgtcgtca tacatcctag aaggttacga aaagaaccgc    1920
cacattaaga gtagcggcaa cttcgatatt aactactgcc acgaccttat tgattattat    1980
aaagcttgca ttaacaaaca tcccgagtgg aagaattatg gatttaagtt taaggaaact    2040
aaccagtaca atgatatagg tcagttctat aaagatgttg agaagcaggg ctattccatc    2100
agctgggcgt atatcagcga gaggatata acaagctgg atgaggaagg gaagatctac    2160
ctgtttgaaa tctacaataa agatttgtca gctcattcaa caggtcgtga taacctgcat    2220
accatgtacc tcaagaatat attttctgaa gacaacctaa agaacatctg tattgaactt    2280
aacggcgaag ccgagttatt ctatcgtaag agttcaatga aatcgaacat aactcacaag    2340
aaagatacca tcctggttaa taagacctat atcaacgaaa ctggcgttcg cgtgtctctt    2400
tctgatgaag actatatgaa agtatataac tattacaaca ataactacgt tatcgacacc    2460
gagaatgata gaaacctgat tgacatcatt gagaagatag ggcacaggaa gtcaaagata    2520
gacatagtga agataaacg ctacacagaa gataaatact tcctttattt accgattacg    2580
attaattatg gcattgagga tgagaatgtc aacagtaaga tcatcgaata tatcgccaaa    2640
caggacaaca tgaacgttat cggtatagat cgtggagaac gcaacttaat ttatatatct    2700
gtgattgaca ataaaggtaa catcatcgaa cagaagtctt tcaatttggt gaacaactac    2760
gactacaaga ataaacttaa gaacatggag aaaacccgcg ataatgctag aaagaactgg    2820
caggaaattg gaaagatcaa agatgttaag agcggctatc ttagtggcgt catatccaag    2880
atcgctcgta tggtaattga ttataacgcc atcattgtta tggaagatct gaataaaggc    2940
tttaagaggg gacggtttaa agtagaacgc caggtatacc agaagttcga gaatatgctg    3000
atcagtaagc tgaactacct ggtatttaaa gaacgtaagg ctgatgagaa tggtggtatc    3060
ctccgtggtt atcaattaac ttacattcct aagagtatta gaacgtcgg taaacaatgc    3120 ggttgcatct tctatgttcc tgctgcatat acttctaaga tcgacccggc aacagggttt    3180
atcaatatct tcgattttaa gaaatattca ggttcaggta tcaacgcgaa ggtgaaagat    3240
aagaaggaat tcctcatgtc aatgaattct atccgctata ttaatgaagg cagcgaagaa    3300
tatgagaaga taggccatag agaactgttt gcctttagct ttgattataa caactttaag    3360
acttataacg tttctagtcc ggttaacgag tggaccgcct acacctacgg cgaacggatc    3420
aagaaactgt acaaggatgg tagatggctg cgtagcgaag tgctgaacct gactgagaat    3480
cttatcaaac tgatggaaca gtataacatc gaatataagg atggccatga tattcgtgaa    3540
gacattagtc atatggatga aacacgcaac gcagacttca tttgcagcct attcgaagag    3600
ctgaaatata ctgttcagtt gcgtaatagt aaatccgagg ctgaagacga gaattatgac    3660
cgactggtta gtcccatact gaatagctcg aacggcttct atgattcgag cgactatatg    3720
gagaatgaga ataacacgac gcatacgatg ccaaaggacg cagatgccaa cggtgcctat    3780
```

| tgtattgcgt | tgaaagggct | ctatgagatt | aataagatta | agcagaattg | gagcgacgac | 3840 |
| aagaagttca | aagagaacga | gctgtacatt | aacgttacgg | aatggttaga | ttacattcag | 3900 |
| aatcgtcgct | tcgaataa | | | | | 3918 |

<210> SEQ ID NO 16
<211> LENGTH: 3819
<212> TYPE: DNA
<213> ORGANISM: Artificial Sequence
<220> FEATURE:
<223> OTHER INFORMATION: Modified MAD nuclease nucleic acid sequence

<400> SEQUENCE: 16

| atggaagata | aacagtttct | cgaacgttac | aaggaattta | ttggtctcaa | ttccctgagt | 60 |
| aagaccctgc | gcaactcgct | gatcccagtc | ggcagcacac | ttaagcacat | tcaagaatat | 120 |
| ggtattctgg | aggaagatag | cttacgcgct | cagaaacgcg | aagagctgaa | aggtattatg | 180 |
| gatgattact | atcggaacta | tattgaaatg | caccttcgtg | atgtccatga | cattgattgg | 240 |
| aacgagctgt | tgaagcgtt | aacggaagta | aagaagaacc | agacagacga | cgcaaagaaa | 300 |
| tgcctagaga | agatacagga | gaagaagagg | aaggagatct | accagtattt | gagcgatgac | 360 |
| gcggtattct | ccgaaatgtt | caaagagaag | atgatttcag | gtattctacc | agactttatt | 420 |
| cgttgtaacg | aagagtatag | cgaagaagag | aaagaagaga | aactaaagac | agttgccctg | 480 |
| tttcaccggt | tcacgagttc | cttcaacgat | ttcttcctga | accgtaagaa | cgtcttcacg | 540 |
| aaagaggcca | ttgctacagc | tattggttat | cgcgtagtgc | atgagaatgc | tgaaatcttt | 600 |
| cttgagaaca | tggttgcctt | tcagaacatt | cagaagtctg | ctgagagtca | aattagcatc | 660 |
| attgaacgaa | agaacgaaca | ctacttcatg | gaatggaaac | tgtcccatat | cttcacagcg | 720 |
| gattactata | tgatgcttat | gacgcagaag | gcgatcgagc | actataacga | gatgtgtggc | 780 |
| gtcgtaaatc | agcacatgaa | agaatactgt | cagaaggaaa | agaagaattg | gaatctttac | 840 |
| cgtatgaaac | gcttgcacaa | acagattctg | tcaaacgcga | gcacctcttt | taagattccc | 900 |
| gagaagtacg | agaatgatgc | ggaggtgtac | gaaagcgtga | actccttctt | acagaatgtg | 960 |
| atggaaaaga | ccgttatgga | acgtatcgct | gtactgaaga | caacaccgaa | caactttgac | 1020 |
| cttttccaaga | tctacataac | cgcgccctac | tacgagaaaa | tttctaacta | tctgtgtggt | 1080 |
| tcgtggaaca | ccatcgccga | ctgtctgact | cactattacg | aacaacagat | cgcgggcaaa | 1140 |
| ggcgctcgca | aagaccagaa | agtgaaagct | gcggtgaagg | cggataagtg | gaagtcgctg | 1200 |
| tcggaaatcg | agcagttact | taagaatac | gcccgggctg | aagaggtcaa | acgtaaacct | 1260 |
| gaagagtaca | tcgcagaaat | agagaacatt | gtctctttga | aggaagtcca | cttgctggaa | 1320 |
| tatcatccgg | aagttaacct | gatcgagaac | gagaagtatg | ctacagaaat | caaagatgta | 1380 |
| ctggacaact | atatggaatt | atttcattgg | atgaaatggt | tctatatcga | agaagctgtg | 1440 |
| gagaaagaag | ttaatttcta | cggtgaattg | gatgatctct | atgaagaaat | tcgtgatatt | 1500 |
| gtcccgttat | ataacaaagt | gcgcaattat | gtgacccaga | accgtatag | tgataccaag | 1560 |
| attaaactaa | actttggtac | gccgacccta | gccaatgggt | ggtccaagtc | gaaagaatac | 1620 |
| gattataacg | cgattctgct | tcagaaagac | ggcaagtact | atatgggtat | cttcaatccg | 1680 |
| gtgcagaaac | cggagaaaga | aatcattgaa | ggacattcgc | atcctttgga | aggcaatgaa | 1740 |
| tacaagaaaa | tggtttatta | ttacttaccg | tccgcgaaca | agatgctgcc | caaggttctt | 1800 |
| ctttctaaga | aagggatgga | aatataccag | ccgagcgagt | acatcattaa | tggttataaa | 1860 |
| gagcgtcgcc | atatcaaatc | ggaggagaaa | tttgatttac | agttctgtca | tgacttgatt | 1920 |

```
gattatttca aatcaggcat tgaacgcaac ccggattgga aagtgtttgg ctttcacttc    1980
tcggacaccg acacgtatca agacatatct ggcttctata gggaagtgga ggatcagggc    2040
tacaagatcg attggactta tatcaaagaa gccgatatag atcgtttaaa cgaagaaggc    2100
aaattatatc tcttccagat ctataacaaa gacttcagtg agaaatcgac aggacgcgag    2160
aaccttcaca caatgtatct taagaatcta ttttccgaag agaacatacg cgaacaagtt    2220
cttaagttaa acggtgaagc ggagatattc tttcggaaga gcagtgtgaa gaaaccaata    2280
atccacaaga aggtacgat gttagtgaac aggacgtaca tggaagagat gcatggcgag    2340
agtgtaaaga agaatatacc ggagaaagag taccaagaaa tttataacta catgaaccat    2400
cggtggaaag gtgagcttag cgctgaagcg aaagagtatc tgaagaaagc agtttgtcac    2460
gaaacgaaga aagatattgt taagattat cgttatagcg tcgataagtt cttcattcac    2520
cttccgatca cgattaacta tcgtgcaagt ggcaaagaag cgttgaattc agtagctcag    2580
cgctatatcg cgcaccagaa tgatatgcat gtgattggta ttgaccgtgg agagagaaat    2640
cttatttatg ttagcgttat caacatgcag ggagaaatca ttgagcagaa atctttcaac    2700
gttgtgaata aatataatta caaagagaag ctgaaagaac gcgaacagaa tcgtgacgag    2760
gctcggaaga attggaaaga gattggccag attaaagatc tcaaggaagg ttatctaagc    2820
ggcgtaatcc atgaaattgc caagatgatg attaaatacc atgcaatcgt ggcgatggaa    2880
gaccttaatt acgggttcaa gaggggggaga ttcaaagttg aacgacaggt atatcagaag    2940
ttcgagaaca tgctgattca gaaattgaat tatctggtat ttaaggatcg tagcgccgat    3000
gaggatggcg tgttctgcg tggataccag ctggcctaca ttcctgatag tgtaaagaaa    3060
ttaggacgcc aatgcggaat gattttctat gtgccggcag cattcacgag caagattgat    3120
ccagctacgg gcttcgtcga tatcttcaac cacaaggcat acacgacaga ccaagcgaag    3180
cgtgagttta tattaagctt tgatgaaata tgttatgatg tggaacgtca actgttccgc    3240
tttacattcg actacgccaa ctttgcgaca cacaacgtga cattagcacg taataattgg    3300
actatctata ccaacggtac gcgtacccag aaggaatttg tgaaccgtcg tgtccgcgac    3360
aagaaagaag tatttgaccc taccgagaag atgttaaagt tgttagaact ggagggtgtt    3420
gagtaccaga gtggcgcgaa tcttcttcca aagttggaga agatcagtga tcctcacctg    3480
tttcatgagc tgcagcgcat tgtacgcttc acggtacagc tgcgcaattc gaagaacgaa    3540
gagaatgatg tggattacga ccatgttata tctcccgtac tgaatgaaga gggcaaattc    3600
tttgactcaa gtaagtacga gaacaaagaa gaaaagaagg agtcattact gcctgtagat    3660
gcggacgcta acggcgccta ttgcatagct ttgaaaggcc tttacattat gcaggcaata    3720
cagaagaatt ggtcgaaga gaaagccctg agtcccgatg tcttacgcct gaataataac    3780
gactggttcg attacattca gaacaaacgc tatcggtaa                          3819
```

<210> SEQ ID NO 17
<211> LENGTH: 3864
<212> TYPE: DNA
<213> ORGANISM: Artificial Sequence
<220> FEATURE:
<223> OTHER INFORMATION: Modified MAD nuclease nucleic acid sequence

<400> SEQUENCE: 17

```
atgaataata acactaataa ttcttttcgaa ccgttcatcg gcggaaattc agttagtaag     60
accttgagaa atgagttacg ggttggaagc gagtatacag gtaaacacat taagaatgc    120
```

| | |
|---|---|
| gcgatcattg cggaggatgc cgtcaaagct gagaatcagt atatcgttaa agaaatgatg | 180 |
| gatgacttct atcgggactt catcaaccgc aaactggatg cgttacaagg tatcaactgg | 240 |
| gagcaattgt ttgacattat gaagaaagcg aaactggata gagcaacaa agtgtctaaa | 300 |
| gaattagata agattcagga atcaacgcgc aaagagattg tcaagatatt tagtagtgat | 360 |
| cccatttata aggacatgct aaaggcagat atgattagta agattctgcc tgaatacatc | 420 |
| gttgataaat acgcgatgc tgcaagccgc attgaagctg tgaaggtctt ttacggattc | 480 |
| tcaggctact tcatcgattt ctgggcttct cgtaagaacg tgtttagcga taagaatatt | 540 |
| gcttctgcga taccgcaccg tattgtcaat gttaatgctc gtatccatct cgacaacatc | 600 |
| acggcgttta atcgtattgc ggagattgcg ggagatgagg tagccggaat tgccgaggac | 660 |
| gcgtgcgcat atttgcagaa tatgagcctg aagacgtgt ttactggtgc atgttatggt | 720 |
| gaattcattt gccagaagga tattgatcgc tataataata tttgcggcgt gattaatcaa | 780 |
| catatgaacc agtattgtca gaataaaaag atcagtcgtt ccaaattcaa gatggagcgt | 840 |
| cttcacaaac agattctgtg tcgcagtgaa tcaggtttcg aaatcccgat tggattccaa | 900 |
| accgacggcg aagttattga tgcaattaat agcttctcaa ctattcttga agagaaggac | 960 |
| attctggatc gcctgcggac tttgagccaa gaagtaactg ggtacgacat ggagcgcatt | 1020 |
| tatgtgtcgt ctaaagcctt cgaatcggtg agcaagtaca ttgatcacaa gtgggatgtt | 1080 |
| atcgcaagca gcatgtacaa ttacttctca ggtgcggttc gcggcaaaga cgataagaaa | 1140 |
| gatgcgaaga tccagactga aattaaaaag atcaagagct gttctctgtt agatttaaag | 1200 |
| aaattagtgg acatgtatta caagatggat gggatgtgtc tggaacacga agccacagag | 1260 |
| tacgtggcgg gtattacgga tcctggtg gacttcaact acaagacctt cgatatggac | 1320 |
| gatagtgtaa agatgatcca gaatgaacat atgataaatg agatcaaaga atatctcgac | 1380 |
| acgtacatgt caatttatca ttgggcgaaa gactttatga tcgacgagct agtcgaccgc | 1440 |
| gatatggagt tctactccga attagatgag atttactacg accttcaga tattgtcccg | 1500 |
| ctgtacaaca aggtacgcaa ttatgttact cagaaaccgt acagccaaga caagatcaaa | 1560 |
| ctgaactttg gctctccgac cctggctaac ggatggagca atccaaaga atttgacaac | 1620 |
| aatgttgtgg tgctgctgcg tgatgaaaag atctacttag cgatactaaa tgtcggtaac | 1680 |
| aagccttcca aagacatcat ggcaggcgag gaccgccgtc gcagtgatac ggattacaag | 1740 |
| aagatgaatt actatttact gcccggtgcg tcaaagaccc tcccacacgt gttcatctcg | 1800 |
| tctaacgcgt ggaagaaaag ccatggcatc ccggatgaga ttatgtacgg atataaccag | 1860 |
| aataagcacc tgaaatcttc tccgaacttt gatctggaat tctgccgaaa gcttattgat | 1920 |
| tattacaagg aatgcataga tagctatcct aactaccaga tcttcaactt taaattcgct | 1980 |
| gccaccgaga cctataatga tatttcagag ttctataaag atgttgaacg ccagggttat | 2040 |
| aagatcgaat ggagttatat atcagaggat gacattaatc agatggaccg cgatggtcag | 2100 |
| atctacctct tccagattta taacaaagac ttcgcgccga actcgaaggg tatgcagaac | 2160 |
| ctccacactc tgtatttgaa gaatatattc agtgaggaga atctgagcga cgtcgttatt | 2220 |
| aagctcaacg gcgaagccga gcttttcttt cgtaaatcat caatccaaca caacgtgggg | 2280 |
| cataagaaag gttccgttct cgttaataag acctacaaga ccacagagaa gacagagaac | 2340 |
| ggtcagggcg aaatcgaagt aattgagagc gtcccggatc agtgctatct tgaactcgtg | 2400 |
| aaatactggt ctgagggtgg cgtgggtcag ctgagcgagg aagcctctaa atacaaggac | 2460 |
| aaagtgtctc actatgcagc gaccatggat attgttaaag atcgccgtta tactgaagac | 2520 |

```
aaattcttta ttcacatgcc gatcaccatt aatttcaaag ccgataaccg caacaacgta    2580
aacgagaagg tgctgaaatt tattgcggag aacgacgacc tccacgtaat tgggattgac    2640
cgtggtgaac gtaatttgtt gtatgtaagc gtcattgact cccgcggacg tattgtagaa    2700
cagaagtcct ttaacatcgt tgagaactac gagagcagca agaacgtcat tcgaaggcat    2760
gattataagg gcaaacttgt caataaagaa cactaccgaa acgaggccag gaagtcctgg    2820
aaagaaatag gcaagataaa ggagatcaaa gaaggctatc tgtcacaggt tatccatgaa    2880
atctcgaaac ttgtgctgaa gtacaacgca atcatcgtca tggaagacct aaactatggg    2940
tttaaacgtg gcaggtttaa agtggaacgt caggtgtatc agaaatttga aaccatgctg    3000
attaataaac tggcgtacct tgtagataaa tcacgcgccg tagatgaacc gggcggacta    3060
ctgaaaggtt atcagctgac ctatgttccg gataacctgg gtgaactggg aagccaatgc    3120
ggcattattt tctatgttcc agcagcttac acctccaaga ttgatccagt gaccgggttc    3180
gtcgatgtat ttgactttaa agcatatagt aatgccgaag cccgattaga cttcattaac    3240
aaattagact gcatccgtta tgatgcctca cgcaataaat ttgagatcgc cttcgattat    3300
ggtaatttcc gcacccatca tactacatta gcaaagacgt cttggacaat ctttattcat    3360
ggcgatcgca tcaagaagga acgtgggtcc tatggctgga aggacgaaat aattgacatt    3420
gaagcccgaa tccgtaaact atttgaagac accgacatcg agtatgccga tggccacaac    3480
ttaattggcg atattaatga actggaatca cccattcaga aaaaattcgt tggagaatta    3540
ttcgacataa tccgcttcac ggtccagcta cgcaactcga agagcgagaa atatgatgga    3600
accgagaagg aatatgataa gattatctcg ccggtgatgg atgaagaggg tgtgttttc    3660 accaccgatt cctatatccg cgcggacggc acagaactac ctaaagatgc agatgcaaat    3720
ggcgcatatt gtatagccct gaaaggtctg tatgacgtct tagccgtgaa gaaatactgg    3780
aaggaaggcg agaaattcga tcggaagctg ctcgcgatca caaattataa ttggtttgac    3840
ttcatacaga accgtcggtt ctaa                                           3864
```

<210> SEQ ID NO 18
<211> LENGTH: 3693
<212> TYPE: DNA
<213> ORGANISM: Artificial Sequence
<220> FEATURE:
<223> OTHER INFORMATION: Modified MAD nuclease nucleic acid sequence

<400> SEQUENCE: 18

```
atgcatgaga caatgggaa gacttattg gtatctaccc ggtatctaag      60
acattgcgct tcgaactgaa acccgttggt aagacacagg aatacatcga gaaacacggc     120
attctggacg aagatctgaa acgtgcaggc gactacaaga gcgtaaaaaa gataattgac     180
gcgtatcata atacttcat agatgaggcg ctgaatggca ttcaactgga cggattaaag     240
aactactatg aattatacga aaagaaaaga gataacaatg aggagaaaga attccagaaa     300
atccagatgt cgctgcggaa acaaatagtt aaacgtttct cagaacatcc gcagtataag     360
tatttattca agaagaact gatcaagaac gtcctcccag aatttactaa ggataatgcg     420
gaagagcaaa cgctggtgaa gagcttccag gaattcacaa cttacttcga aggcttccac     480
cagaatcgta agaacatgta ttcggatgaa gagaagtcga ccgcgattgc gtatcgtgtc     540
gtgcaccaga acctccctaa atatatcgac aacatgcgca tcttctcaat gattctgaac     600
acagacatta gaagcgactt aaccgaatta ttcaataacc taaagactaa gatggatatt     660
```

```
acgatcgttg aagaatactt cgcgattgat gggttcaata aagtggtaaa tcagaaggga    720
atagacgttt acaatacaat tctaggcgcc ttctcaactg atgacaatac gaagattaaa    780
ggcctgaacg agtatatcaa cctgtacaat cagaagaaca aagcgaagct gccgaagctg    840
aaaccgttgt ttaaacagat tctcagcgat cgtgataaga taagcttcat tccggaacag    900
tttgatagtg ataccgaagt gctagaagcg gtagatatgt tctacaatag attactgcag    960
ttcgtgatcg agaacgaagg tcagatcacg attagtaagc tcttgaccaa cttctctgcc   1020
tacgatctta acaagatcta cgtcaagaac gatactacta ttagcgctat cagcaatgac   1080
ttattcgatg actggagcta cattagcaaa gccgtacgtg agaactacga tagcgagaac   1140
gttgacaaga acaagcgcgc ggcagcgtat gaggagaaga aagagaaagc tctgagcaag   1200
atcaagatgt attcaattga agaactgaat ttctttgtca agaagtatag ttgtaacgaa   1260
tgtcacatag aaggctattt cgaacgcagg atcttggaaa tcctcgataa gatgcgctac   1320
gcgtacgaat cctgcaagat cttgcatgat aaaggcctga ttaacaacat tagtctgtgc   1380
caggaccgtc aagccatttc ggagcttaag gacttcctcg atagtatcaa agaggtccaa   1440
tggttactga aacctctgat gattggccag gaacaggcag ataaggaaga agccttctat   1500
acggaactct tacggatctg gaagaattaa gaaccgatta cgctgctgta taataaagta   1560
cgtaattacg taacaaagaa accgtacacc ctcgagaagg tcaagttaaa cttctataag   1620
agcactctgc ttgacggttg ggataagaat aaagagaaag acaacctggg cattattctg   1680
ctgaaagatg ggcagtatta tttgggaatt atgaatcgtc gtaacaacaa gattgccgat   1740
gatgcgccat tagctaagac agataatgta tataggaaga tggaatataa attacttacg   1800
aaagtgtctg caaacctgcc tcgcatattt cttaaagata aatataatcc gtcggaggaa   1860
atgctggaga gtacgagaa agggacccat ctcaagggtg agaatttctg catagatgat   1920
tgtcgcgaac tgatcgactt cttcaagaaa gggattaaac agtatgaaga ttggggccag   1980
tttgacttca aatttagcga tacagaaagc tatgatgata tttcagcctt ctataaagaa   2040
gtggagcatc aaggctacaa gatcaccttt agagacatag atgaaacgta catcgatagt   2100
ctggtcaacg aaggcaaact ttatttattt caaatctaca acaaggattt ctcaccgtac   2160
tctaaaggaa cgaagaacct ccataccctta tactgggaaa tgctctttag tcaacagaat   2220
ctgcagaata tcgtgtacaa actgaatgga acgcggaaa tattctaccg taaagcaagc   2280
attaatcaga aagacgttgt cgtacacaag gcggacctcc caataaagaa taaagaccct   2340
cagaacagca agaaggagag tatgtttgat tatgatatca ttaaggacaa gcgattcacg   2400
tgcgataaat atcaatttca tgttcctatt accatgaact tcaaagccct tggtgagaat   2460
cactttaatc gcaaggtgaa ccgcttaatc cacgatgccg agaatatgca cattattggg   2520
attgatcgtg gagaacgtaa tcttatctat ctgtgtatga ttgatatgaa aggtaacatt   2580
gtaaagcaga ttagtcttaa cgagatcatc agctacgata agaataaatt agaacacaag   2640
cgtaactatc accagctgct caagacacgg gaagacgaga ataaatctgc ccgccagtca   2700
tggcagacca ttcataccat taaagaatta aaggagggct acttatcgca ggttattcat   2760
gtcatcacgg atcaatggt agaatataat gctattgttg ttctggaaga tcttaacttc   2820
ggcttcaaac agggtcgcca gaagtttgaa cgccaggtgt accagaagtt tgagaagatg   2880
ctgattgata aactgaatta ccttgtggac aagagcaaag ggatggatga agacggaggt   2940
cttctacacg cttatcagct cacgatgaa tttaagagct ttaagcagtt aggcaaacaa   3000
agcggcttcc tttactatat tcccgcatgg aatacttcta aattagatcc cactactggt   3060
```

```
ttcgtaaatt tattctatac gaaatacgaa tcggtggaga agagtaagga atttatcaat    3120
aacttcacca gcattctcta taaccaggag cgggaatact tcgaatttct ctttgattac    3180
tcggccttca caagcaaagc tgaaggaagc cgtctgaaat ggacagtgtg ttctaaaggc    3240
gagcgtgttg agacctatcg caatccgaaa aagaacaacg agtgggacac gcaaaagatt    3300
gatcttacct ttgagctaaa gaaattattt aatgactatt caattagcct gttggacggt    3360
gatttaagag aacagatggg taagatcgat aaagcagact tctacaagaa atttatgaaa    3420
ttattcgccc tgattgtcca gatgcgaaat tccgatgagc gtgaagacaa actgatttca    3480
ccggttctga ataaatatgg tgctttcttt gaaactggaa agaacgagcg gatgccgctg    3540
gacgcggacg cgaacggagc gtacaatatt gcgcgtaaag gcctttggat tattgagaag    3600
attaagaata ccgatgttga acagcttgat aaggtgaaac tcaccattag taacaaagag    3660
tggcttcagt atgcgcagga gcatatctta taa                                 3693
```

<210> SEQ ID NO 19
<211> LENGTH: 3708
<212> TYPE: DNA
<213> ORGANISM: Artificial Sequence
<220> FEATURE:
<223> OTHER INFORMATION: Modified MAD nuclease nucleic acid sequence

<400> SEQUENCE: 19

```
atggttgcct ttatcgatga attcgtaggt cagtacccag tttcaaagac ccttcgcttc      60
gaagcacgtc cggttccaga gacgaagaaa tggttggaat cggatcaatg ttccgtcctc     120
tttaacgacc agaagcgcaa cgaatactac ggtgtactta aggaactgct ggacgattac     180
tatcgcgcgt atattgaaga tgccctgacc tccttcacgc tagataaagc cttgctcgag     240
aacgcgtatg atctgtattg taaccgtgat acgaacgcct tctcttcatg ctgcgagaag     300
ctacgtaaag acctggtcaa ggcatttgga aacttgaagg actacctgtt aggctcggat     360
cagttgaagg atctggttaa gctgaaagca aaggttgatg cacctgcggg caagggaaaa     420
aagaaaattg aagtggactc tcgtttaatt aattggttaa acaataacgc gaaatactct     480
gcagaagacc gtgagaagta cattaaggcg attgaatctt cgaaggcttc cgttacctat     540
ctgactaatt ataaacaggc tcgcagaaat atgtttagca gtgaagacaa gagcaccgcg     600
atcgcgttta gagtgattga ccagaacatg gtgacctatt cggcaatatc agaatatat      660 gagaagatca aggcgaagta tcccgaatta tatagcgcgc tgaagggctt cgagaagttt     720
ttctcaccca ccgcgtatag tgaaatcctc tcccaaagta agattgatga atataactac     780
caatgtattg gccgcccgat tgacgatgcc gactttaagg gcgtgaacag ccttataaat     840
gaatatcgcc agaagaacgg catcaaagca cgcgaactgc cggttatgtc tatgctttat     900
aaacagatcc tatcagacag agataactcg tttatgtccg aggtcataaa tcgtaacgag     960
gaggcgattg agtgcgctaa gaatggatac aaggtatcat acgcgctgtt taacgagctg    1020
ctgcagctgt ataagaaaat attcacagaa gacaactacg gcaatatcta tgttaagact    1080
caacctctta ccgaacttag tcaggcgctc ttcggcgatt ggagcatcct gcgcaatgcc    1140
ttggacaacg gtaaatatga caaagacatc attaatttag cggagttgga gaaatacttc    1200
agcgaatact gcaaggttct ggacgcagat gacgcagcga agattcagga caagttcaac    1260
cttaaagatt atttcatcca gaaaaacgcc ctggatgcga cactcccgga tctggataag    1320
attacgcagt acaagccgca tttagacgcc atgctacagg cgatccgcaa atacaagcta    1380
```

```
ttctcgatgt acaacggcag gaagaaaatg gacgttccgg agaacggtat cgatttcagt    1440
aacgaattta acgccatata tgataagctt tctgaattct caatcttgta tgaccgtatc    1500
cgcaatttcg cgaccaagaa accttactcc gatgagaaga tgaaactgtc ctttaatatg    1560
cctaccatgc tggcaggctg ggattacaac aatgagaccg caaatgggtg ctttctcttc    1620
atcaaggacg gcaaatactt cttaggtgtt gcggacagta aaagtaagaa tatcttcgac    1680
tttaagaaga atccgcatct attagacaaa tattcctcta aggatattta ctacaaagtg    1740
aagtataaac aggtatctgg gtccgccaag atgctgccga agtcgtctt tgctggttcg     1800 aacgagaaga tctttggtca tttgattagc aaacgcattc tggaaatccg tgagaaaaaa    1860
ctatacactg ccgctgccgg tgatcgcaag gccgttgcag agtggattga cttcatgaaa    1920
tctgcgattg ctattcaccc ggagtggaac gaatacttca agttcaagtt taagaacacc    1980
gcagaatatg ataacgcgaa taaattctat gaagacattg ataaacaaac ctatagtcta    2040
gagaaagtcg aaatacctac ggaatatatc gacgaaatgg tgtcccaaca taagctctac    2100
ctgtttcagc tttatacgaa agatttctcg gacaagaaaa agaagaaggg tacagacaat    2160
cttcatacaa tgtactggca cggtgtcttt agcgatgaga tctgaaagc cgtgactgaa     2220 ggtacgcaac ccatcattaa actgaatgga gaggccgaga tgttcatgcg caacccgagc    2280
atcgaatttc aggttacaca tgagcacaac aaacccatag cgaacaagaa cccgttaaac    2340
acgaagaagg aatcggtatt taattacgat ttaatcaaag ataaacgcta cactgaacgt    2400
aagttctact tcattgtcc tatcactctg aacttccgcg ccgataaacc cattaaatac     2460
aatgagaaga tcaatcggtt cgtggagaac aacccggacg tctgcattat aggtatcgat    2520
cgtggagagc gtcacctgct gtattataca gtgatcaatc agaccggcga tattcttgag    2580
caaggaagtt tgaacaagat cagcggcagc tatacgaacg ataaaggtga aaggtgaac     2640 aaagaaaccg attaccatga cctgctggat cggaaggaga aggaaagca tgttgcgcag    2700 caggcatggg aaacaattga gaacatcaaa gaactcaagg cgggttattt aagccaggta    2760
gtgtataaac tgacccagtt aatgttgcag tacaacgcgg tgattgttct ggagaatctc    2820
aatgttggat tcaaacgtgg ccgtacgaaa gtcgagaagc aggtctatca gaaattcgag    2880
aaggcgatga tcgacaagtt aaattacttg gtctttaaag atcgtggtta tgagatgaac    2940
ggtagctacg ctaagggtct gcagctaact gataaatttg aatcgtttga caagattggt    3000
aagcagacgg gatgtatta ttatgttata ccgtcttata cgagccatat tgaccctaag     3060
acgggattcg tgaacctgct aaatgcgaaa ctacgctatg agaatataac gaaagcacaa    3120
gataccattc gtaaatttga ttcgattagc tacaacgcta agcggattaa tttcgagttt    3180
gcattcgatt accgttcatt tggcgtcgat atggcccgta tgaatgggt ggtatgcacg      3240 tgcggtgact tacgctggga atattccgcc aagacacgtg aaaccaaagc gtattcggtg    3300
accgaccgtc ttaaagaact cttcaaggcg cacggtattg attacgtcgg aggcgagaat    3360
ttagtatcgc acattaccga ggtcgcagat aaacatttcc tgtcgactct gctgttctat    3420
ttacggttgg ttcttaagat gcgttatacc gtcagcggca ccgagaacga gaatgacttt    3480
atactctcgc cggttgagta cgcaccaggg aagttctttg actcacgcga ggccactagc    3540
accgaaccga tgaatgcaga cgcaaatggt gcttatcata ttgcgcttaa gggattgatg    3600
acaattcgtg gaattgaaga cggcaagtta cacaactatg gtaaaggagg cgagaacgct    3660
gcctggttca aatttatgca gaaccaagaa tacaagaata atggttaa                 3708
```

<210> SEQ ID NO 20
<211> LENGTH: 3780
<212> TYPE: DNA
<213> ORGANISM: Artificial Sequence
<220> FEATURE:
<223> OTHER INFORMATION: Modified MAD nuclease nucleic acid sequence

<400> SEQUENCE: 20

| | | | | | |
|---|---|---|---|---|---|
| atgaattata | agaccggcct | ggaagatttc | atcggcaaag | aatctttaag | taagacgctg | 60 |
| cgcaatgcgt | tgattccaac | agaaagtacg | aagattcaca | tggaagaaat | gggcgtgatt | 120 |
| cgtgacgatg | aactgagagc | ggagaaacag | caggaactga | aggaaatcat | ggacgattat | 180 |
| tatcgcgcgt | ttatagaaga | gaagctcggt | cagatacaag | gaattcagtg | gaacagccta | 240 |
| tttcaaaaga | tggaggagac | catggaggat | attagtgtga | ggaaagatct | ggataagatt | 300 |
| cagaacgaga | aacgcaaaga | gatttgttgc | tacttcacta | gcgataagcg | attcaaagac | 360 |
| ctgtttaatg | cgaaattaat | caccgatatc | ctgccaaact | tcattaaaga | taacaaagaa | 420 |
| tatacggaag | aagagaaggc | agagaaagaa | caaactcgcg | tattgttcca | gcgctttgct | 480 |
| accgcattca | ctaactactt | taaccagcga | cgtaataact | ttagtgaaga | caatatttcg | 540 |
| accgcaatct | catttcgcat | cgtgaatgag | aattctgaga | ttcatctgca | gaatatgcgt | 600 |
| gccttccagc | gcattgagca | gcagtacccg | gaagaagtct | gtggcatgga | ggaagaatat | 660 |
| aaagatatgc | ttcaagaatg | gcaaatgaag | catatttact | ctgtggattt | ctatgatcgc | 720 |
| gaacttactc | agccaggaat | agagtactat | aacggcattt | gcggaaagat | taatgagcac | 780 |
| atgaatcaat | tctgtcagaa | aaaccgcatt | aataagaatg | acttcagaat | gaagaaattg | 840 |
| cacaaacaaa | tattatgcaa | gaaatctagt | tactatgaaa | taccattccg | ctttgaatcc | 900 |
| gaccaagaag | tatatgacgc | attgaatgag | tttataaaga | caatgaagaa | gaaagaaatt | 960 |
| attcgccgtt | gtgttcactt | gggtcaggaa | tgcgacgact | acgacttagg | aaagatctac | 1020 |
| attagcagca | ataaatatga | gcagataagc | aatgctttgt | atggatcttg | ggacaccatt | 1080 |
| cgtaaatgca | tcaagaagaa | atacatggat | gcgttaccgg | gcaaaggcga | agaaggaa | 1140 |
| gagaaggcag | aagctgccgc | caagaaggag | gaatatcgca | gtatagctga | tattgacaag | 1200 |
| attattagcc | tctacggaag | tgagatggac | cggaccataa | gcgccaagaa | atgcattaca | 1260 |
| gagatctgcg | atatggcggg | ccaaattagc | atcgacccgc | ttgtgtgtaa | ctccgacatt | 1320 |
| aaactgctgc | agaataagga | gaagaccacg | gagattaaga | cgattctgga | ctcgtttctg | 1380 |
| catgttatc | aatggggcca | gacatttatc | gtaagcgata | ttattgagaa | ggacagctat | 1440 |
| ttctacagtg | aacttgaaga | tgttctagaa | gactttgaag | gtattactac | cctgtataac | 1500 |
| cacgtgcgta | gctatgtgac | ccagaagccg | tatagtaccg | tcaaattcaa | actccacttt | 1560 |
| gggtcgccga | cgctggcaaa | cggttggagt | cagtccaagg | aatatgataa | taatgccatc | 1620 |
| ctgctgatgc | gcgaccagaa | attctacctg | ggcatattca | acgttcgtaa | taaccagac | 1680 |
| aaacaaataa | ttaaaggaca | cgagaaagaa | gagaagggcg | actacaaaaa | gatgatctat | 1740 |
| aacctgctgc | ctggtccgtc | gaagatgctg | cctaaggtgt | tcataaccag | ccgctccggc | 1800 |
| caggagacct | ataagcctag | caaacatatc | ttggatgggt | ataatgagaa | acgtcacatc | 1860 |
| aaatcatctc | ccaagtttga | tctgggctat | tgttgggatt | tgatagatta | ttataaggaa | 1920 |
| tgcattcaca | agcacccgga | ttggaagaat | tatgactttc | acttctccga | caccaaagat | 1980 |
| tacgaggata | ttagcggatt | ctatagagaa | gtagaaatgc | agggctacca | gattaagtgg | 2040 |
| acgtatatct | cagcagatga | aatccagaag | cttgacgaga | aaggccaaat | attcctgttt | 2100 |

-continued

```
cagatctata acaaagactt ctcggtacat tcaactggca aggacaacct ccataccatg    2160
tatttgaaga acctgttctc agaagagaac cttaaggata tagtactcaa attaaatggc    2220
gaggccgaac tgttctttcg taaagcgtct atcaagactc caattgttca caagaaaggg    2280
tcggttctgg tcaaccgttc gtatactcaa accgtgggta acaaagagat aagagttagc    2340
attcctgaag aatactatac agaaatttat aactacctga atcacattgg caaaggcaaa    2400
ttatctagcg aagcccagcg ttacctggac gaaggaaaga taaagagttt cacggcgacc    2460
aaagacattg ttaagaacta tcgttattgc tgcgatcatt atttcttaca cttaccgatt    2520
actattaact ttaaagctaa gagcgacatc gcggttaacg aacgtacact ggcgtatatc    2580
gcgaagaagg aagatatcca tatcataggc atagaccgag gtgagagaaa cctgctctat    2640
ataagcgtaa tcgatgtgca cggcaacatt cgtgaacagc gcagcttcaa tattgtaaat    2700
ggttacgact accagcagaa acttaaagac cgggagaaga gtcgcgacgc agcacgaaag    2760
aactgggaag aaatcgagaa gatcaaagaa ctcaaggagg gctacttatc tatggttatc    2820
cactatatcg cgcgcttggt tgtcaagtac aatgcagtgg tggcgatgga ggacctgaac    2880
tatgggttta agaccggacg gtttaaagtg gaacgtcagg tttatcagaa atttgaaacg    2940
atgctgattg agaagttgca ttaccttgta tttaaagacc gtgaagtgtg tgaggaaggt    3000
ggagtactgc gcgggtatca actgacttat atcccagaat cactcaagaa ggtaggcaaa    3060
cagtgcgggt tcatcttcta cgttccggca ggctatacta gtaagatcga cccaactact    3120
ggctttgtta atctgttcag ctttaagaac ttgaccaacc gggaatcacg tcaggacttc    3180
gttggtgagt tcgatgaaat ccgttatgat cgtgacaaga acatgtttga attctccttc    3240
gactataata attatataaa gaagggcacc atgctggcta gcacgaaatg gaaggtttac    3300
accaacggta cacgttttaa agagaatagt tgttaatggca aatataccag tcagtccatg    3360
gaagtagaac taactgatgc catggagaag atgttacaac gtgctggtat cgaataccac    3420
gacggcaaag acctgaaagg gcaaatcgtt gagaagggca tcgaagccga gattattgat    3480
atcttccgtc taaccgtcca gatgaggaac tcgcgttcgg aatctgagga tcgtgaatat    3540
gatagactaa tttctcccgt gcttaatgat aaaggtgagt tctttgatac agccactgcc    3600
gacaagacgt taccgcaaga tgccgacgca aatggtgcgt actgtattgc gctgaaaggt    3660
ctgtatgaag tgaagcagat caaagagaac tggaaagaga acgaacaatt cccgcgaaat    3720
aagcttgtgc aggacaacaa gacgtggttt gacttcatgc aaaagaagcg atatctgtaa    3780
```

<210> SEQ ID NO 21
<211> LENGTH: 3903
<212> TYPE: DNA
<213> ORGANISM: Artificial Sequence
<220> FEATURE:
<223> OTHER INFORMATION: Modified MAD nuclease nucleic acid sequence

<400> SEQUENCE: 21

```
atgagcattt accaggaatt tgtgaacaag tatagtctgt ccaagacact gcggttcgaa      60
ctaatcccac agggtaagac cctggagaat atcaaagccc gcggcctat  tctggatgac     120 gagaagcgcg cgaaggacta caagaaagcg aaacagatca tcgataaata ccaccaattc     180
ttcattgagg agatcctgtc atcggtatgt atttcagaag atttattaca gaattatagt     240
gacgtttatt tcaaactcaa aaagagtgac gatgataatc tgcagaaaga ctttaagagt     300
gcgaaagaca ccataaagaa acagatttct gaatacatca aggatagtga aaatttaag     360 aacctgttca atcagaatct gatcgatgcg aagaaagggc aagaatcaga tttaatcctg     420
```

```
tggctcaagc agtcgaaaga taatggtatt gaattattta aagccaattc tgacatcacg    480
gatattgatg aagcgctgga aatcataaag agcttcaagg gttggacaac gtacttcaag    540
ggcttccatg agaatcgcaa gaatgtatat agttctaacg acatcccaac ctccatcatt    600
tatcgtatcg tagatgataa ccttcccaag tttctggaga ataaagcgaa atacgagtct    660
ttgaaagata aagcgccaga ggccattaac tacgaacaga ttaagaagga tctggcagaa    720
gaattgacat tcgatattga ttacaagaca tccgaagtga accaaggggt gttcagctta    780
gatgaagtct ttgaaattgc taatttcaat aattatttaa atcaatccgg cattaccaaa    840
tttaacacca taataggtgg caaattcgtg aatggcgaga acactaagcg caaaggtatt    900
aacgagtaca tcaatctgta ttcacagcag attaacgaca gaccctgaa gaagtataag     960 atgtcagtct tgtttaaaca gatcctcagt gatacagaga gcaaatcgtt cgtaatagat   1020
aaactggaag atgactctga cgtcgtaacc actatgcagt cgttctatga gcagatcgcg   1080
gcctttaaga ccgttgaaga gaagagcatt aaggaaacgt tatcactcct gtttgacgac   1140
cttaaagcac agaaactgga cctttcgaag atttacttta agaatgataa atctctgact   1200
gatctgtctc aacaggtatt tgatgattac tcggtgattg gcactgctgt gttagaatat   1260
attacccagc aaattgcacc taagaatttg gataatccct ccaagaagga acaggagctc   1320
atagctaaga gacggagaa agctaagtac ctgtcactgg aaacaattaa gctggcctta   1380 gaagagtta acaaacatcg cgatatcgat aagcagtgtc ggtttgaaga aatcttagct   1440
aacttcgccg ctatacctat gatcttcgat gaaattgccc agaacaagga taatctggct   1500
caaattagca tcaaatatca gaatcaaggg aagaaagact tgttacaggc tagcgcggag   1560
gatgatgtta aagcgattaa ggacttactg gaccagacga ataacttatt acataaactt   1620
aagatctttc acatctcaca gtctgaagat aaggccaaca tcctggataa agatgaacat   1680
ttctatcttg tgttgaaga atgctatttc gagttagcta atatagtacc tttatacaac   1740
aagattcgta attacatcac acagaaacca tacagcgacg agaagtttaa gttgaacttt   1800
gagaactcca cccttgctaa tggctgggac aagaataaag aaccagataa taccgcaatc   1860
ctctttatca aagatgacaa atactacctg ggtgttatga caagaagaa taacaagatc   1920 tttgacgata aggccattaa agagaacaaa ggagaaggtt acaagaagat cgtttataaa   1980
ttgttgcccg gcgcgaacaa gatgctccct aaggtcttct ttagtgctaa gagcattaag   2040
ttctataacc cgtcagaaga tattctgcgc atccgaaatc acagcaccca cacgaagaac   2100
ggatctccac agaaaggcta tgagaaattc gagtttaaca tagaggattg tcgcaagttt   2160
attgacttct ataagcagag catttcaaag catcctgaat ggaaagattt cggattccgc   2220
ttcagtgata cccagcgcta taatagcatt gatgaattct accgagaagt cgagaaccaa   2280
ggctacaaac tgacgtttga gaacatctct gaatcctata ttgattcggt ggttaatcag   2340
ggcaagctgt acttatttca aatttataat aaggatttct ccgcctacag taaaggtcga   2400
cctaacctgc acaccctgta ttggaaagcg ttatttgatg agcgtaatct ccaagacgtt   2460
gtgtacaaac tcaacggtga agccgaatta ttctatcgca acagtcgat tcccaagaaa   2520 atcacccatc cggcgaagga ggctattgcg aacaagaaca aagataatcc taagaaggaa   2580
tctgtgttcg aatacgatct aattaaagac aagagattca cggaggacaa gttcttcttc   2640
cactgcccga tcaccattaa cttcaaatcc agcggcgcca ataagtttaa cgacgaaatc   2700
aacctgttgc tcaaagagaa ggctaacgac gtgcacatac tgagtataga tcgaggcgaa   2760
```

```
cggcacttag cgtattatac cttagtggat ggcaagggta atattatcaa gcaagacaca    2820
tttaatatta tcggtaatga ccgcatgaag acaaattacc acgacaagct ggccgccatc    2880
gagaaggatc gtgatagtgc tcgtaaagat tggaagaaga ttaacaatat caaagagatg    2940
aaagaaggtt atttgagcca ggtagttcat gaaatcgcca aattagttat tgaatataat    3000
gcaatcgttg tatttgaaga cctgaacttc ggctttaaac gcggtcgatt caaagttgag    3060
aagcaggtgt atcagaagct ggaaaagatg ctgattgaga aattgaacta ccttgtgttt    3120
aaagacaatg agttcgacaa gacgggcggc gtgctgaggg cctatcagct aaccgcgccg    3180
tttgagacat ttaagaaaat gggtaaacaa acaggcatca tttactacgt tccagcgggc    3240
ttcaccagca agatatgtcc tgtcacaggc ttcgtgaatc agctgtaccc aaagtacgaa    3300
agtgttagta aatctcagga attttttctct aaatttgata agatttgcta caatttggat    3360
aaaggctatt tcgaatttag ctttgattac aagaacttcg gtgacaaggc tgcgaaaggc    3420
aaatggacaa ttgcatcgtt cgggagccgt ctgattaact ttcgtaatag tgacaagaat    3480
cataactggg ataccaggga agtgtatcca accaaagaac tggagaaact tctcaaagac    3540
tattccatcg aatacggcca tggtgaatgt attaaagcgg cgatctgcgg agagagtgac    3600
aagaaattct tcgccaaact gacctcagtg ttaaacacca ttctgcagat gcgaaacagt    3660
aagactggta cagagctgga ctatttaatt tcaccggttg cagatgtaaa tggcaacttc    3720
tttgatagcc gtcaggcacc gaagaatatg ccacaggatg cagatgcaaa cggtgcatac    3780
catattggtt tgaaaggtct gatgctcctg ggtcgcataa agaacaacca agagggcaag    3840
aagctgaacc tggttataaa gaacgaagaa tacttcgaat tcgttcagaa tcgtaacaac    3900
taa                                                                 3903

<210> SEQ ID NO 22
<211> LENGTH: 3624
<212> TYPE: DNA
<213> ORGANISM: Artificial Sequence
<220> FEATURE:
<223> OTHER INFORMATION: Modified MAD nuclease nucleic acid sequence

<400> SEQUENCE: 22
atgtattatc agaatttaac caagatgtat ccgattagta agacccttcg taacgaacta      60
attccggtag gaaagactct ggagaacata cggaagaatg gtatcttgga agcagatatc     120
caacgtaaag ccgactatga acatgtcaag aaattgatgg acaattacca caaacaacta     180
atcaacgaag cgctgcaggg agtgcatctg tcggatctga cgacgcttta tgacctgtac     240
tttaatcttt ctaaagagaa gaactcagta gatgccttct ccaaatgcca ggataaactt     300
cggaaagaga tcgtgtcttt cctgaagaat acgagaatt ttccgaagat cggaaataaa     360
gaaattatca aactgatcca gagcctgaat gacaacgacg cagacaataa cgcgctcgat     420
tccttctcga atttctatac ctacttcagc agctataacg aggttagaaa gaatctctac     480
agcgatgagg agaagagtag cacagtagca tataggttaa taaacgagaa cttgccgaaa     540
tcgttagata atattaaagc gtacgccatc gctaagaaag ccggtgtccg tgcggaaggc     600
ctctcggaag aggaacagga ttgtttattc attattgaaa cctttgaacg tacccctgaca    660 caggacggca tcgataatta caatgctgat atcggcaagc ttaacaccgc aatcaatctg     720
tacaatcaac agaacaagaa gcaggaaggt ttccgcaaag taccgcagat gaaatgcctg     780
tacaaacaga ttctgagcga ccgggaagag gcattcatcg atgaatttag tgatgacgag     840
gacctgataa ccaacattga agcttcgct gagaatatga atgtattcct aaactccgaa      900
```

```
ataatcaccg actttaagaa tgcgctcgta gaatctgacg gctccctggt ctatataaag      960
aatgatgtgt ccaagacctt attctcaaat attgtattcg gaagctggaa cgcaattgat     1020
gagaagttat cggatgaata cgatctggcg aattcaaaga agaaaaaaga cgagaagtat     1080
tatgagaagc gtcagaagga actaaagaag aataagagct atgatctgga aactattatt     1140
gggctgtttg atgactctat cgacgtcatc ggtaaataca tagagaagct cgagtcagac     1200
attaccgcca ttgctgaagc caagaacgac ttcgatgaga tcgtccttcg taagcatgat     1260
aagaacaaat cacttcgtaa gaacacaaac gcggttgaag ccataaagag ttacctggac     1320
accgttaaag atttcgaacg ggatattaaa ctgattaacg ggtctggcca ggaggtggag     1380
aagaatctgg ttgtatatgc agagcaggag aacatactcg cagagatcaa gaacgtggac     1440
agtctctata acatgtcacg taactatctg acacagaaac cattctcgac ggagaaattt     1500
aaactgaact ttgagaatcc cacgttacta aatggttggg accgtaacaa agagaaagac     1560
tatctaggaa tactgttcga gaaagagggt atgtattatc ttggcatcat caataacaat     1620
caccgtaaga tcttcgagaa cgagaaactg tgcaccggta agaaagttg cttcaataag      1680 atcgtgtata aacagatctc gaatgcggcc aaatacctgt ctagcaaaca gattaacccg     1740
cagaacccgc ctaaggaaat tgcagagatc ctgctgaaac gcaaagcaga tagcagttcc     1800
ttaagtcgta aagaaacgga actgttcatc gattatttga agacgatttt cttagtaaat     1860
tatccaatga tcatcaacag tgacggcgag aatttctttta actttcactt taaacaggct     1920
aaggactacg gctcgttaca ggagttcttc aaggaagtgg aacatcaagc gtattccttg     1980
aagacacgtc cgattgacga ttcttacatt tatcggatga ttgacgaagg taagctgtac     2040
ctgtttcaga ttcataataa agacttcagc ccgtactcga aaggaaatct caacctgcat     2100
actatatatc tccagatgtt attcgatcag cgtaatctga ataacgttgt atataaactg     2160
aacggcgaag cagaagtgtt ttatcgccca gcgtccatta acgatgagga agttattatc     2220
cacaaagcag gtgaagaaat taagaacaag aatagcaaac gggccgttga caaacctacg     2280
agcaaattcg gctatgatat tattaaagac cgccggtatt cgaaagataa gtttatgctt     2340
catatccctg tgaccatgaa cttcggcgtt gacgagaccc gccgcttcaa tgatgtcgta     2400
aatgatgcct tacgcaatga tgagaaggtt cgcgtgattg gcattgatag aggtgaacgc     2460
aacctgttat acgtcgtagt ggtcgatacg gatggaacta tccttgaaca gattagtctc     2520
aacagtatta ttaataacga gtatagcatt gaaactgatt atcacaagct gctggacgag     2580
aaagagggtg atcgcgaccg cgccagaaag aactggacca caattgagaa tattaaggaa     2640
ctgaaagagg gctatctgtc acaagttgta aatgttatcg cgaagttggt gttaaagtac     2700
aatgcgatta tttgcctgga agatttaaat ttcggtttca aacgtgggcg ccagaaggtc     2760
gagaagcagg tgtatcagaa gtttgaaaag atgctgatcg ataaactgaa ttatttagta     2820
attgataaat cgcgtaaaca ggagaagccg gaagaattcg tggtgctttt gaacgcattg     2880
cagttaacaa gcaaatttac ttcttcaaaa gatatgggta aacagacagg aattatttat     2940
tatgtccctg cgtatcttac ctctaagatt gacccaacca cgggctttgc gaacctgttc     3000
tatgtgaaat atgagaatgt cgagaaagcc aaggaattct tttctagatt cgactctatc     3060
agctataaca acgagagcgg atactttgaa tttgcctttg attataagaa attcactgat     3120
cgcgcctgtg gcgctcggag ccagtggaca gtttgcacct atggcgagcg aattattaag     3180
taccgtaacg cggacaagaa taacagcttt gatgacaaga ccatcgtact gtcggaagaa     3240
```

```
ttcaaagagt tgtttagcat ctatggtatc agctacgaag atggcgcgga attaaagaac    3300
aagatcatga gcgtagatga ggcggatttc tttcgttgtc tgaccggctt attacagaag    3360
acattacaaa tgcgtaacag cagtaatgat ggcacacggg attacattat aagcccaatt    3420
atgaacgata gaggcgagtt cttcaattct gaggcgtgtg atgcttcgaa accgaaagat    3480
gccgatgcca acggcgcctt caacattgcg cgcaaaggcc tgtgggtgtt agagcagatt    3540
cgcaatactc ccagcggcga taaattgaat ctggcgatga gcaacgctga atggctggag    3600
tacgcacaga ggaatcagat ctaa                                           3624
```

<210> SEQ ID NO 23
<211> LENGTH: 3621
<212> TYPE: DNA
<213> ORGANISM: Artificial Sequence
<220> FEATURE:
<223> OTHER INFORMATION: Modified MAD nuclease nucleic acid sequence

<400> SEQUENCE: 23

```
atgtattacc agaatttaac gaagaaatac ccggtgagca agactatacg gaatgaactg      60
attcctattg gtaagactct ggagaacatt cgtaagaata atatcctcga atccgatgtc     120
aagcgcaagc aagattatga acatgtgaaa gggattatgg acgaatatca taaacaactg     180
attaacgaag cgctggataa ctacatgctg ccgagtctga atcaagccgc agagatctat     240
ctaaagaaac atgttgacgt cgaggacaga gaggaattta gaagacccca ggatctgttg     300
cgcagagagg ttacgggtcg cttgaaggaa cacgagaatt atacgaagat cggaaagaaa     360
gatatccttg atcttctgga agctgccgt tctatttcgg aagaagatta taatgccctg     420
gagagcttcc gcaatttcta cacatacttc acctcttata caaggtgcg tgagaacctg     480 tattcggatg aagagaagtc aagcacagtg gcctacagat taatcaacga gaaccttccg     540
aaatttcttg ataatattaa gagttacgcg tttgtcaaag ccgcaggcgt cctggcagat     600
tgcattgaag aagaagagca agatgcactg tttatggttg agaccttcaa tatgactctg     660
actcaagaag gcatcgatat gtataattat caaatcggga aggtgaactc cgcgattaat     720
ctgtataatc agaagaatca aaagttgaa gaatttaaga gatcccgaa gatgaaagtt     780 ctatacaaac agatcctgag tgatagggag gaggtattca taggagagtt caaagacgat     840
gaaacgttgc tcagctcaat cggcgcgtat ggcaatgtct taatgacata tcttaaatcc     900
gagaagatta acatcttctt cgatgcactc cgggaatctg aagggaagaa cgtgtacgta     960
aagaacgacc tttcaaagac caccatgtcg aatatcgtct tcggaagctg gagcgcattc    1020
gatgaattgt tgaaccagga gtatgatctt gccaacgaga acaagaagaa ggacgacaaa    1080
tactttgaga gcgccagaa ggagctaaag aagaataaga gttatacgct ggagcaaatg    1140
tctaatctga gtaaggaaga cattagccct attgagaatt acatcgaacg gatttcagaa    1200
gacatcgaga agatatgcat atataatggc gaattcgaga agattgtggt gaacgaacat    1260
gacagctctc gtaaactgag taagaacatc aaagcggtta agtcatcaa ggattacttg    1320 gattcgatca agaactgga acacgacatt aaattgatca acggtagtgg ccaggaattg    1380
gagaagaact tggttgtcta tgtgggtcaa gaagaagccc tggagcagct ccgtccagtg    1440
gatagtttat acaaccttac tcgaaactat ttaacaaaga agcccttctc aactgagaaa    1500
gtgaaactta acttcaacaa gagtacgctg ttaaatggtt gggacaagaa caaagaaacg    1560
gataatctcg gtatcttgtt cttcaaagac gggaagtatt atcttggcat catgaataca    1620
actgctaaca agcctttgt gaatccgccc gccgccaaga ccgagaatgt ctttaagaaa    1680
```

```
gttgattata agttactgcc gggcagtaat aagatgctgc caaaggtctt tttcgctaag      1740
agcaacattg gatactataa cccatctacg gaactgtact ctaattataa gaaaggcacc      1800
cacaagaaag gcccgtcatt ctctatcgat gattgtcata acttaattga tttcttcaaa      1860
gaaagcatta agaaacatga ggactggtcg aaatttggtt tcgaattctc tgacaccgca      1920
gactaccgcg atatttcaga gttctaccgc gaagtagaga acagggcta taaacttacg      1980 tttacggaca tagacgaaag ctatattaac gatctgattg aaaagaatga actgtattta      2040
ttccaaattt ataacaaaga tttcagtgaa tatagcaaag gtaaactcaa cctgcatacc      2100
ctgtacttca tgatgttgtt cgatcagcgc aacttggaca atgtggtcta caaactgaac      2160
ggtgaggcag aagttttcta ccgcccggca tcgatcgccg agaatgaact ggttattcat      2220
aaagcaggtg agggtataaa gaacaagaat ccgaaccgtg caaaggtcaa agaaactagc      2280
acgttctctt acgatattgt gaaagataaa cgatatagca aatacaaatt taccctgcat      2340
attcctatta ccatgaactt cggagtcgac gaagtgcggc gtttcaatga cgtgatcaac      2400
aacgccctgc gtacggacga taatgtcaat gttattggca tcgatcgtgg tgaacgcaat      2460
ctgctttacg tcgttgtaat aaacagtgaa ggaaagattc tcgaacagat ttctttaaat      2520
tctatcatca acaaagaata tgatatcgaa accaactacc atgctctgtt ggatgaacgt      2580
gaggacgatc ggaacaaagc gcgtaaagat tggaatacga tcgagaatat taagaattg      2640 aagaccggct atctttcaca ggttgtcaat gttgttgcta aattagtgct gaaatataac      2700
gcgatcattt gcctggaaga tttaaacttt gggttcaaac gaggccgtca gaaagtggag      2760
aagcaagttt accagaagtt cgagaagatg cttattgaga aactaaacta cctcgtgatt      2820
gacaagagcc gcgaacaggt gtcaccggag aaaatgggtg gcgcgttgaa tgcattgcag      2880
ttaacttcta aatttaagtc gttcgctgaa ctaggcaagc aaagcggtat tatctattac      2940
gtaccggcct acttaactag taagattgat cccacgaccg gctttgtaaa cctcttctat      3000
attaaatacg agaacatcga gaaagccaag cagttcttcg atggatttga cttcattcgt      3060
ttcaacaaga aagacgacat gttgagttc tcgtttgatt ataagtcatt cacccagaaa      3120
gcttgtggaa tccgtagcaa atggattgtg tacacgaatg gagaacgtat tattaaatat      3180
ccgaacccgg agaagaataa tttgtttgat gagaaagtga ttaacgtgac cgacgagatt      3240 aagggttttgt tcaaacaata ccgcatcccg tacgagaacg gtgaagacat taaggaaatt      3300
ataatcagca aagcagaggc tgacttctat aaacgcctat ccgcctgtt gcatcagact      3360 ttgcagatgc gcaactccac cagcgatggc actcgtgact acataatttc tccggtgaag      3420
aacgatagag gtgagttttt ctgttccgaa ttctcagaag ggaccatgcc gaaagatgcg      3480
gatgccaatg gagcgtacaa tatcgcgcgc aagggtctgt gggtactgga acagataaga      3540
cagaaggatg aaggagagaa ggtaaactta tcgatgacaa atgcagaatg gctgaagtat      3600
gcccaactgc acctgctgta a                                                3621
```

<210> SEQ ID NO 24
<211> LENGTH: 3756
<212> TYPE: DNA
<213> ORGANISM: Artificial Sequence
<220> FEATURE:
<223> OTHER INFORMATION: Modified MAD nuclease nucleic acid sequence

<400> SEQUENCE: 24

```
atgaatcaca tgaaacagtt cactaatcaa ttctcgttat cgaagacact tagattcgaa       60
```

```
ctcatcccac agggaaagac gaaagaattt attgaaataa atggcctgat cgagaaggat       120
aacgaacgtg ccgtgagcta caagaaagtc aagaagatca tcgatgaata tcacaagtac       180
tttattgaaa tggttctgtg cgactttaaa ctgcacggtc tggagaccta tgaaacgatc       240
ttcaataaga aggagaaaga tgacaccgac aagaaggagt tgacaacat tcgtaattct        300 ctgcgcaagc aaatcgcgga cgccttcgca aagaatccga acgatgaaat caagaacgt        360 tttaagaatc tgttcgctaa ggaactgatt aaacaggacc ttcttaactt cgtggatgac       420
gagcagaagg agctggtgaa cgaatttaag gacttcacta cttactttac cggcttccat       480
cagaatcgtc gtaacatgta cgttgcagat gagaaggcaa ccgcgatcgc ataccgtctc       540
gttaacgaga acctgcccaa gttcatcgat aatcttaaga tctatgagaa gatcaagaag       600
gacgctccgg aactgatctc cgatcttaac aagacactgg ttgagatgga agaaatcgtg       660
cagggcaaga cactggatga aatatttagc ttaagcttct tcaaccagac cttaacgcaa       720
actggcattg aactgtataa tattgttatt ggtgggcgca ccgcggacga agggaagaca       780
aagattaaag gactgaatga atatatcaac acagactaca accagaaaca aacggacaag      840
aagaagaaac aagccaagtt taaacagctc tataaacaaa ttctgagtga ccgtcattct       900
gtgagcttcg ttgcggagac cttttgagacc gatgcacaat tactggagaa tattgaacag     960
ttctactcat ccgtgctgtg taactatgaa gatgatggtc acaccacaaa tatattcgaa      1020
gcgataaaga atctgataat aggtctcaag acgttcgacc tatcaaagat ctatctccga       1080
aacgatacgt ccttaaccga tattagtcag aaactgtttg cgactggag catcatcagc       1140 agcgcactca cgactatta tgagaagcag aacccgatct cgtctaagga gaagcaggag       1200
aagtatgatg agaggaaagc gaaatggttg aaacaggact ttaatatcga aactattcaa       1260
acggcgctca atgaatgcga ctcagaaatc attaaagaga aaaacaacaa gaatattgtt       1320
agcgagtatt tcgcgaaatt aggcttagat aaagacaaca agattgaccct cttgcaaaag     1380 atccaccata attacgttgt aattaaggac ttgctgaatg agccgtatcc agagaatatc      1440
aaactgggaa atcagaagga acaagtgtct cagattaagg actttctgga tagcatccta       1500
aaccttatac acttcttgaa accgctcagt ctgaaagata agataaaga gaaggatgag       1560 ttatttttatt ctttgttcac cgcgctgttc gagcacctgt cgcagaccat atcgatctat     1620
aacaaggttc gcaactactt gacgcagaag gcttacagta ccgaaaagat caagttgaac       1680
tttgagaata gtacattgct gaacggatgg gacgtgaaca aagagccggt gaatactagc       1740
gtcatattcc gtaagaatgg tttgttctac ctgggaatca tgtctaaatc caataaccgc      1800
atctttgaac gtaatgtacc ggtgtgtaag aatgaagaaa ccgcctttga gaaatgaat       1860 tataaattac tgccgggcgc taacaagatg ctcccgaagg tattcctgag cgctaagggg      1920
atagaaagct ttcagccgtc agcagaaatc cagagcaaat atcagaagga gacccataag      1980
aaaggtgatg cgttcgtgcg caaagatatg gagaacctta tcgacttctt taaacaaagt      2040
attgccaaac ataccgattg gaagcacttc aaccaccagt tctcgaagac ggaaacttac      2100
aacgatttaa gtgaattcta taggaggtt gagaagcaag atataaaatt aacctttacc       2160
aagttggacg agacttatat taaccaactg gtggatgagg taaactgta tctgttccaa       2220 atctataaca aggacttcag tccccttcagt aagggcaagc cgaacatgca taccctgtat     2280
tggaagatgt tatttgacga acagaatctg cagaatgttg tatataaact gaatggtgaa       2340
gccgaagtct tcttccggca gagttccatc aaacagaccg accgtatcat tcacaaagca      2400
aaccaagcca ttgacaacaa gaatccactg aacaataaga agcagtcgtc tttcaattac      2460
```

```
gacttaatta aggacaaacg gtttaccctg gataaatttc agttccacgt tccgattacg    2520
ctgaacttca aagccgaagg gaatgaatac ctgaacacta aagtgaacga ataccttaag    2580
agcaacagtg atgtgaagat cattggcttg gacagaggtg agcgacattt gatctatctg    2640
actttaatca atcagaaggg tgaactactc aaacagcaaa gtcttaacgt cattgctact    2700
agccaagaac atgagactga ctataagaac ttactggtta acaaggagaa cgaaagagca    2760
aatgccaggc aagattggaa gaccatcgag actattaaag aattgaaaga aggttactta    2820
tcgcaggtcg tacatcaaat agcaaccatg atggtggacg agaacgcgat cgtggttatg    2880
gaagatctga atgccggatt catgcgtggc agacagaagg ttgaacggca ggtgtatcag    2940
aagctggaga aaatgcttat tgagaagtta aactacctgg tgttcaagaa taatgatgtg    3000
aatgaaaccg ccggtgtatt aaatgcgtta cagctcacga ataaatttga aagtttcgag    3060
aagatgggca agcagagtgg ctttctgttc tatgtgcccg cgtggaacac gagtaagatc    3120
gacccggcca caggatttgt cgactttctt aaacccaaat acgaaagcgt cgagaaagct    3180
aagctcttct ttgagaagtt tgaatccatt aaatttaacg cggacaagaa ttacttcgaa    3240
tttgaatttg attacaagaa gttcaccgag aaggcggaag gcagtcaaac caaatggacg    3300
gtctgcacgc atagtgacgt ccgctaccgc tataatccgc agaccaaagc tagcgatgaa    3360
gtcaatgtaa ctaacgaact taaactgata tttgacaaat ttaagattga atacaagaat    3420
gggaagaact taaagaccga attgcttctc caagatgata agcagctgtt ctccaaactc    3480
ctccattatc tggcgctgac ccttatgctc agacaaagta agagtggcac ggatatcgat    3540
ttcattctta gcccggtcgc caagaacggt gtgttctatg actcgaggaa tgccatgcca    3600
aacttaccta aggatgccga tgcgaacgga gccttccaca ttgctctgaa aggcctgtgg    3660
tgtgtgcagc aaataaagaa ggcggatgac ctgaagaaaa ttaagctggc aatttcgaat    3720
aaagaatggc tctcatttgt ccagaatctg aaataa                              3756
```

```
<210> SEQ ID NO 25
<211> LENGTH: 30
<212> TYPE: DNA
<213> ORGANISM: Artificial Sequence
<220> FEATURE:
<223> OTHER INFORMATION: Primer sequence

<400> SEQUENCE: 25
atggcaccca agaagaagag gaaggtgtta                                       30

<210> SEQ ID NO 26
<211> LENGTH: 10
<212> TYPE: PRT
<213> ORGANISM: Artificial Sequence
<220> FEATURE:
<223> OTHER INFORMATION: Artificial peptide

<400> SEQUENCE: 26

Met Ala Pro Lys Lys Lys Arg Lys Val Leu
1               5                   10

<210> SEQ ID NO 27
<211> LENGTH: 20
<212> TYPE: DNA
<213> ORGANISM: Artificial Sequence
<220> FEATURE:
<223> OTHER INFORMATION: Primer sequence

<400> SEQUENCE: 27
```

```
ttgggtaacg ccagggtttt                                                20
```

<210> SEQ ID NO 28
<211> LENGTH: 20
<212> TYPE: DNA
<213> ORGANISM: Artificial Sequence
<220> FEATURE:
<223> OTHER INFORMATION: Primer sequence

<400> SEQUENCE: 28

```
tgtgtggaat tgtgagcgga                                                20
```

<210> SEQ ID NO 29
<211> LENGTH: 199
<212> TYPE: DNA
<213> ORGANISM: Artificial Sequence
<220> FEATURE:
<223> OTHER INFORMATION: Yeast editing cassette

<400> SEQUENCE: 29

```
ggccccaaat tctaatttct actgttgtag atacgacgtt gaagcttcac aattttacg     60
ccgacataga ggagaagcat atgtacaatg agccggtcac aaccctcgag acacgacgtt  120
gaagcttaac aaacacacca cagacgtggg tcaataccat tgaaagatga gaaaagtaac  180
aatatacgcg ctcctgccc                                                199
```

<210> SEQ ID NO 30
<211> LENGTH: 199
<212> TYPE: DNA
<213> ORGANISM: Artificial Sequence
<220> FEATURE:
<223> OTHER INFORMATION: Yeast editing cassette sequence

<400> SEQUENCE: 30

```
ggccccaaat tctaatttct actcttgtag atacgacgtt gaagcttcac aattttacg     60
ccgacataga ggagaagcat atgtacaatg agccggtcac aaccctcgag acacgacgtt  120
gaagcttaac aaacacacca cagacgtggg tcaataccat tgaaagatga gaaaagtaac  180
aatatacgcg ctcctgccc                                                199
```

<210> SEQ ID NO 31
<211> LENGTH: 199
<212> TYPE: DNA
<213> ORGANISM: Artificial Sequence
<220> FEATURE:
<223> OTHER INFORMATION: Yeast editing cassette sequence

<400> SEQUENCE: 31

```
ggccccaaat tctaatttct actattgtag atacgacgtt gaagcttcac aattttacg     60
ccgacataga ggagaagcat atgtacaatg agccggtcac aaccctcgag acacgacgtt  120
gaagcttaac aaacacacca cagacgtggg tcaataccat tgaaagatga gaaaagtaac  180
aatatacgcg ctcctgccc                                                199
```

<210> SEQ ID NO 32
<211> LENGTH: 200
<212> TYPE: DNA
<213> ORGANISM: Artificial Sequence
<220> FEATURE:
<223> OTHER INFORMATION: Yeast editing cassette sequence

<400> SEQUENCE: 32

-continued ggccccaaat tctaatttct actgtgtgta gatacgacgt tgaagcttca caatttttac        60
gccgacatag aggagaagca tatgtacaat gagccggtca caaccctcga gacacgacgt      120
tgaagcttaa caaacacacc acagacgtgg gtcaatacca ttgaaagatg agaaaagtaa      180
caatatacgc gctcctgccc                                                  200

<210> SEQ ID NO 33
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 33
ggccccaaat tctaatttct actgttgtag atcttttctc atctttcaat ggttttttgta      60 tcctcgccat ttactctcgt cgggaaagag cgcaatggat acaattcccc acttttctca      120
tcttacaatg gtattgaccc acgtctgtgg tgtgtttgtg aagcttcaac gtcgtcaata      180
tacgcgctcc tgccc                                                      195

<210> SEQ ID NO 34
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 34
ggccccaaat tctaatttct actcttgtag atcttttctc atctttcaat ggttttttgta      60 tcctcgccat ttactctcgt cgggaaagag cgcaatggat acaattcccc acttttctca      120
tcttacaatg gtattgaccc acgtctgtgg tgtgtttgtg aagcttcaac gtcgtcaata      180
tacgcgctcc tgccc                                                      195

<210> SEQ ID NO 35
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 35
ggccccaaat tctaatttct actattgtag atcttttctc atctttcaat ggttttttgta      60 tcctcgccat ttactctcgt cgggaaagag cgcaatggat acaattcccc acttttctca      120
tcttacaatg gtattgaccc acgtctgtgg tgtgtttgtg aagcttcaac gtcgtcaata      180
tacgcgctcc tgccc                                                      195

<210> SEQ ID NO 36
<211> LENGTH: 196
<212> TYPE: DNA
<213> ORGANISM: Artificial Sequence
<220> FEATURE:
<223> OTHER INFORMATION: Yeast editing cassette sequence

<400> SEQUENCE: 36
ggccccaaat tctaatttct actgtgtgta gatcttttct catctttcaa tggttttttgt      60 atcctcgcca tttactctcg tcgggaaaga gcgcaatgga tacaattccc cacttttctc      120
atcttacaat ggtattgacc cacgtctgtg gtgtgtttgt gaagcttcaa cgtcgtcaat      180
atacgcgctc ctgccc                                                     196

<210> SEQ ID NO 37
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 37

```
ggccccaaat tctaatttct actgttgtag atccgacgag agtaaatggc gattttttca      60
ataccattga aagatgagaa aagtaaagaa ttgtatccat tgcgctcgtt cccgacgaga     120
gtataaggcg aggatacgtt ctctatggag gatggcatag gtgatgaaga tgaaggagaa    180
gcaatatacg cgctcctgcc c                                               201
```

<210> SEQ ID NO 38
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 38

```
ggccccaaat tctaatttct actcttgtag atccgacgag agtaaatggc gattttttca      60
ataccattga aagatgagaa aagtaaagaa ttgtatccat tgcgctcgtt cccgacgaga     120
gtataaggcg aggatacgtt ctctatggag gatggcatag gtgatgaaga tgaaggagaa    180
gcaatatacg cgctcctgcc c                                               201
```

<210> SEQ ID NO 39
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 39

```
ggccccaaat tctaatttct actattgtag atccgacgag agtaaatggc gattttttca      60
ataccattga aagatgagaa aagtaaagaa ttgtatccat tgcgctcgtt cccgacgaga     120
gtataaggcg aggatacgtt ctctatggag gatggcatag gtgatgaaga tgaaggagaa    180
gcaatatacg cgctcctgcc c                                               201
```

<210> SEQ ID NO 40
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 40

```
ggccccaaat tctaatttct actgtgtgta gatccgacga gagtaaatgg cgattttttc      60
aataccattg aaagatgaga aaagtaaaga attgtatcca ttgcgctcgt tcccgacgag     120
agtataaggc gaggatacgt tctctatgga ggatggcata ggtgatgaag atgaaggaga    180
agcaatatac gcgctcctgc cc                                              202
```

<210> SEQ ID NO 41
<211> LENGTH: 201
<212> TYPE: DNA
<213> ORGANISM: Artificial Sequence
<220> FEATURE:

<223> OTHER INFORMATION: Yeast editing cassette sequence

<400> SEQUENCE: 41

```
ggccccaaat tctaatttct actgttgtag attccacacc tctgaccaac gctttttatt      60
ggtatgattg cccttggtgg tactattggt acaggtcttt tcattggatt atccacacct    120
ctgtaaaacg ccggcccagt gggcgctctt atatcatatt tatttatggg ttctttggca    180
tcaatatacg cgctcctgcc c                                              201
```

<210> SEQ ID NO 42
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 42

```
ggccccaaat tctaatttct actcttgtag attccacacc tctgaccaac gctttttatt      60
ggtatgattg cccttggtgg tactattggt acaggtcttt tcattggatt atccacacct    120
ctgtaaaacg ccggcccagt gggcgctctt atatcatatt tatttatggg ttctttggca    180
tcaatatacg cgctcctgcc c                                              201
```

<210> SEQ ID NO 43
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 43

```
ggccccaaat tctaatttct actattgtag attccacacc tctgaccaac gctttttatt      60
ggtatgattg cccttggtgg tactattggt acaggtcttt tcattggatt atccacacct    120
ctgtaaaacg ccggcccagt gggcgctctt atatcatatt tatttatggg ttctttggca    180
tcaatatacg cgctcctgcc c                                              201
```

<210> SEQ ID NO 44
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 44

```
ggccccaaat tctaatttct actgtgtgta gattccacac ctctgaccaa cgctttttat      60
tggtatgatt gcccttggtg gtactattgg tacaggtctt tcattggat tatccacacc    120
tctgtaaaac gccggcccag tgggcgctct tatatcatat ttatttatgg gttctttggc    180
atcaatatac gcgctcctgc cc                                             202
```

<210> SEQ ID NO 45
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 45

```
ggccccaaat tctaatttct actgttgtag atacagtttt ctcacaaaga ttttttttct      60
gtcacgcagt ccttgggtga aatggctaca ttcatccctg ttacatcctc gttcacagtt    120
```
ttctcataaa gattcctttc tccagcattt ggtgcggcca atggttacat gtattggttt    180
tcaatatacg cgctcctgcc c    201

<210> SEQ ID NO 46
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 46
ggccccaaat tctaatttct actcttgtag atacagtttt ctcacaaaga ttttttttct    60
gtcacgcagt ccttgggtga aatggctaca ttcatccctg ttacatcctc gttcacagtt    120
ttctcataaa gattcctttc tccagcattt ggtgcggcca atggttacat gtattggttt    180
tcaatatacg cgctcctgcc c    201

<210> SEQ ID NO 47
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 47
ggccccaaat tctaatttct actattgtag atacagtttt ctcacaaaga ttttttttct    60
gtcacgcagt ccttgggtga aatggctaca ttcatccctg ttacatcctc gttcacagtt    120
ttctcataaa gattcctttc tccagcattt ggtgcggcca atggttacat gtattggttt    180
tcaatatacg cgctcctgcc c    201

<210> SEQ ID NO 48
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 48
ggccccaaat tctaatttct actgtgtgta gatacagttt tctcacaaag attttttttc    60
tgtcacgcag tccttgggtg aaatggctac attcatccct gttacatcct cgttcacagt    120
tttctcataa agattccttt ctccagcatt tggtgcggcc aatggttaca tgtattggtt    180
ttcaatatac gcgctcctgc cc    202

<210> SEQ ID NO 49
<211> LENGTH: 197
<212> TYPE: DNA
<213> ORGANISM: Artificial Sequence
<220> FEATURE:
<223> OTHER INFORMATION: Yeast editing cassette sequence

<400> SEQUENCE: 49
ggccccaaat tctaatttct actgttgtag atggtaatta tcacaataat gatttttcat    60
tcaattttgg acgtacaaag ttccactggc ggcatggatt agtatttgga aggtaattat    120
cacataaatg aacttgttcc ctgtcaaata ttacggtgaa ttcgagttct gggtcgccaa    180
tatacgcgct cctgccc    197

<210> SEQ ID NO 50

```
<211> LENGTH: 197
<212> TYPE: DNA
<213> ORGANISM: Artificial Sequence
<220> FEATURE:
<223> OTHER INFORMATION: Yeast editing cassette sequence

<400> SEQUENCE: 50
ggccccaaat tctaatttct actcttgtag atggtaatta tcacaataat gatttttcat      60
tcaattttgg acgtacaaag ttccactggc ggcatggatt agtatttgga aggtaattat     120
cacataaatg aacttgttcc ctgtcaaata ttacggtgaa ttcgagttct gggtcgccaa     180
tatacgcgct cctgccc                                                    197

<210> SEQ ID NO 51
<211> LENGTH: 197
<212> TYPE: DNA
<213> ORGANISM: Artificial Sequence
<220> FEATURE:
<223> OTHER INFORMATION: Yeast editing cassette sequence

<400> SEQUENCE: 51
ggccccaaat tctaatttct actattgtag atggtaatta tcacaataat gatttttcat      60
tcaattttgg acgtacaaag ttccactggc ggcatggatt agtatttgga aggtaattat     120
cacataaatg aacttgttcc ctgtcaaata ttacggtgaa ttcgagttct gggtcgccaa     180
tatacgcgct cctgccc                                                    197

<210> SEQ ID NO 52
<211> LENGTH: 198
<212> TYPE: DNA
<213> ORGANISM: Artificial Sequence
<220> FEATURE:
<223> OTHER INFORMATION: Yeast editing cassette sequence

<400> SEQUENCE: 52
ggccccaaat tctaatttct actgtgtgta gatggtaatt atcacaataa tgattttca       60 ttcaattttg gacgtacaaa gttccactgg cggcatggat tagtatttgg aaggtaatta    120
tcacataaat gaacttgttc cctgtcaaat attacggtga attcgagttc tgggtcgcca    180
atatacgcgc tcctgccc                                                   198
```